United States Patent
Stoughton et al.

(10) Patent No.: US 11,378,498 B2
(45) Date of Patent: *Jul. 5, 2022

(54) DIAGNOSIS OF FETAL ABNORMALITIES USING POLYMORPHISMS INCLUDING SHORT TANDEM REPEATS

(71) Applicants: Verinata Health, Inc., Redwood City, CA (US); The General Hospital Corporation, Boston, MA (US); GPB Scientific, LLC, Richmond, VA (US)

(72) Inventors: Roland Stoughton, The Sea Ranch, CA (US); Ravi Kapur, Sharon, MA (US); Barb Ariel Cohen, Watertown, MA (US); Daniel Shoemaker, San Diego, CA (US); Ronald W. Davis, Palo Alto, CA (US); Mehmet Toner, Charlestown, MA (US)

(73) Assignees: Verinata Health, Inc., Redwood City, CA (US); The General Hospital Corporation, Boston, MA (US); GPR Scientific, LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/819,992

(22) Filed: Mar. 16, 2020

(65) Prior Publication Data

US 2021/0010913 A1  Jan. 14, 2021

Related U.S. Application Data

(63) Continuation of application No. 13/830,871, filed on Mar. 14, 2013, now Pat. No. 10,591,391, which is a continuation of application No. 13/738,268, filed on Jan. 10, 2013, now abandoned, which is a continuation of application No. 13/433,232, filed on Mar. 28, 2012, now abandoned, which is a continuation of application No. 12/725,240, filed on Mar. 16, 2010, now abandoned, which is a continuation of application No. 11/763,426, filed on Jun. 14, 2007, now abandoned.

(60) Provisional application No. 60/820,778, filed on Jul. 28, 2006, provisional application No. 60/804,815, filed on Jun. 14, 2006.

(51) Int. Cl.
| | |
|---|---|
| *G01N 1/30* | (2006.01) |
| *G16B 20/10* | (2019.01) |
| *G16B 20/20* | (2019.01) |
| *C12Q 1/6883* | (2018.01) |
| *G16B 20/00* | (2019.01) |

(52) U.S. Cl.
CPC .............. *G01N 1/30* (2013.01); *C12Q 1/6883* (2013.01); *G16B 20/10* (2019.02); *G16B 20/20* (2019.02); *C12Q 2600/156* (2013.01); *C12Q 2600/158* (2013.01); *C12Q 2600/16* (2013.01); *G16B 20/00* (2019.02)

(58) Field of Classification Search
None
See application file for complete search history.

(56) References Cited

U.S. PATENT DOCUMENTS

| | | |
|---|---|---|
| 3,560,754 A | 2/1971 | Kamentsky |
| 4,886,761 A | 12/1989 | Gustafson et al. |
| 4,936,465 A | 6/1990 | Zoeld |
| 5,310,674 A | 5/1994 | Weinreb et al. |
| 5,489,506 A | 2/1996 | Crane |
| 5,506,141 A | 4/1996 | Weinreb |
| 5,508,169 A | 4/1996 | Deugau et al. |
| 5,541,072 A | 7/1996 | Wang et al. |
| 5,587,070 A | 12/1996 | Pall et al. |
| 5,622,831 A | 4/1997 | Liberti et al. |
| 5,635,358 A | 6/1997 | Wilding et al. |
| 5,637,469 A | 6/1997 | Wilding et al. |
| 5,695,934 A | 12/1997 | Brenner |
| 5,843,767 A | 12/1998 | Beattie |
| 5,846,708 A | 12/1998 | Hollis et al. |
| 5,861,253 A | 1/1999 | Asgari et al. |
| 5,863,502 A | 1/1999 | Southgate et al. |
| 5,879,624 A | 3/1999 | Boehringer et al. |
| 5,906,724 A | 5/1999 | Sammons et al. |

(Continued)

FOREIGN PATENT DOCUMENTS

| | | |
|---|---|---|
| CN | 1308726 A | 8/2001 |
| CN | 1539992 A | 10/2004 |

(Continued)

OTHER PUBLICATIONS

Zhao, X.X. et al., Enrichment of fetal cells from maternal blood by magnetic activated cell sorting (MACS) with fetal cell specific antibodies: One-step versus two-step MACS, Congen. Anomal., vol. 42, pp. 120-124 (Year: 2002).*
U.S. Appl. No. 14/705,239 filed May 6, Kapur et al.
U.S. Appl. No. 60/951,438, filed Jul. 23, 2007, Lo et al.

(Continued)

*Primary Examiner* — Teresa E Strzelecka

(74) *Attorney, Agent, or Firm* — Fish & Richardson P.C.

(57) ABSTRACT

The present invention provides systems, apparatuses, and methods to detect the presence of fetal cells when mixed with a population of maternal cells in a sample and to test fetal abnormalities, i.e. aneuploidy. In addition, the present invention provides methods to determine when there are insufficient fetal cells for a determination and report a non-informative case. The present invention involves quantifying regions of genomic DNA from a mixed sample. More particularly the invention involves quantifying DNA polymorphisms from the mixed sample.

20 Claims, 28 Drawing Sheets

(56) References Cited

U.S. PATENT DOCUMENTS

| | | |
|---|---|---|
| 5,944,971 A | 8/1999 | Foote |
| 6,008,010 A | 12/1999 | Greenberger et al. |
| 6,030,581 A | 2/2000 | Virtanen |
| 6,036,857 A | 3/2000 | Chen et al. |
| 6,071,394 A | 6/2000 | Cheng et al. |
| 6,124,120 A | 9/2000 | Lizardi |
| 6,129,848 A | 10/2000 | Chen et al. |
| 6,132,607 A | 10/2000 | Chen et al. |
| 6,150,119 A | 11/2000 | Kopf-sill et al. |
| 6,184,029 B1 | 2/2001 | Wilding et al. |
| 6,210,574 B1 | 4/2001 | Sammons et al. |
| 6,210,910 B1 | 4/2001 | Walt et al. |
| 6,242,209 B1 | 6/2001 | Ransom et al. |
| 6,274,337 B1 | 8/2001 | Parce et al. |
| 6,277,489 B1 | 8/2001 | Abbott et al. |
| 6,280,967 B1 | 8/2001 | Ransom et al. |
| 6,372,432 B1 | 4/2002 | Tocque et al. |
| 6,377,721 B1 | 4/2002 | Walt et al. |
| 6,488,895 B1 | 12/2002 | Kennedy |
| 6,551,841 B1 | 4/2003 | Wilding et al. |
| 6,573,082 B1 | 6/2003 | Choi et al. |
| 6,605,454 B2 | 9/2003 | Barenburg et al. |
| 6,641,997 B1 | 11/2003 | Mackinnon |
| 6,783,647 B2 | 8/2004 | Culbertson et al. |
| 6,815,664 B2 | 11/2004 | Wang et al. |
| 6,947,583 B2 | 9/2005 | Ellis et al. |
| 6,958,245 B2 | 10/2005 | Seul et al. |
| 7,208,295 B2 | 4/2007 | Faham et al. |
| 7,224,839 B2 | 5/2007 | Zeineh |
| 7,407,757 B2 | 8/2008 | Brenner |
| 7,428,325 B2 | 9/2008 | Douglass et al. |
| 7,709,194 B2 | 5/2010 | Lo et al. |
| 7,718,367 B2 | 5/2010 | Lo et al. |
| 7,754,428 B2 | 7/2010 | Lo et al. |
| 7,783,098 B2 | 8/2010 | Douglass et al. |
| RE42,315 E | 5/2011 | Lopez et al. |
| 8,024,128 B2 | 9/2011 | Rabinowitz et al. |
| 8,515,679 B2 | 8/2013 | Rabinowitz et al. |
| 8,532,930 B2 | 9/2013 | Rabinowitz et al. |
| 8,682,592 B2 | 3/2014 | Rabinowitz et al. |
| 9,017,942 B2 | 4/2015 | Shoemaker et al. |
| 9,347,100 B2 | 5/2016 | Shoemaker et al. |
| 9,441,273 B2 | 9/2016 | Quake et al. |
| 2002/0005354 A1 | 1/2002 | Spence et al. |
| 2002/0012933 A1 | 1/2002 | Rothberg |
| 2002/0090741 A1 | 7/2002 | Jurgensen et al. |
| 2002/0098535 A1 | 7/2002 | Wang et al. |
| 2002/0106661 A1 | 8/2002 | Virtanen |
| 2002/0108859 A1 | 8/2002 | Wang et al. |
| 2002/0115163 A1 | 8/2002 | Wang et al. |
| 2002/0115164 A1 | 8/2002 | Wang et al. |
| 2002/0115201 A1 | 8/2002 | Barenburg et al. |
| 2002/0123112 A1 | 9/2002 | Wang et al. |
| 2002/0127575 A1 | 9/2002 | Hoke et al. |
| 2002/0132315 A1 | 9/2002 | Wang et al. |
| 2002/0132316 A1 | 9/2002 | Wang et al. |
| 2002/0160363 A1 | 10/2002 | McDevitt et al. |
| 2002/0164825 A1 | 11/2002 | Chen |
| 2003/0044832 A1 | 3/2003 | Blankenstein |
| 2003/0096268 A1 | 5/2003 | Weiner |
| 2003/0152981 A1 | 8/2003 | Hulten |
| 2003/0178641 A1 | 9/2003 | Blair et al. |
| 2003/0219765 A1 | 11/2003 | Costa |
| 2004/0018611 A1 | 1/2004 | Ward et al. |
| 2004/0023222 A1 | 2/2004 | Russell et al. |
| 2004/0063162 A1 | 4/2004 | Dunlay et al. |
| 2004/0077105 A1 | 4/2004 | Wu et al. |
| 2004/0121343 A1 | 6/2004 | Buechler et al. |
| 2004/0146883 A1 | 7/2004 | Kennedy |
| 2004/0197839 A1 | 10/2004 | Daniely et al. |
| 2004/0245317 A1 | 12/2004 | Larionov et al. |
| 2005/0003351 A1 | 1/2005 | Fejgin et al. |
| 2005/0095606 A1 | 5/2005 | Hoke et al. |
| 2005/0142663 A1 | 6/2005 | Parthasarathy et al. |
| 2005/0153329 A1 | 7/2005 | Hakansson et al. |
| 2005/0170373 A1 | 8/2005 | Monforte |
| 2005/0175505 A1 | 8/2005 | Cantor et al. |
| 2005/0175981 A1 | 8/2005 | Voldman et al. |
| 2005/0250147 A1 | 11/2005 | Macevicz |
| 2005/0282220 A1 | 12/2005 | Prober et al. |
| 2006/0003312 A1 | 1/2006 | Blau et al. |
| 2006/0019235 A1 | 1/2006 | Soen et al. |
| 2006/0052945 A1 | 3/2006 | Rabinowitz et al. |
| 2006/0252087 A1 | 11/2006 | Tang et al. |
| 2007/0015171 A1 | 1/2007 | Bianchi et al. |
| 2007/0027636 A1 | 2/2007 | Rabinowitz |
| 2007/0178478 A1 | 8/2007 | Dhallan et al. |
| 2007/0178501 A1 | 8/2007 | Rabinowitz et al. |
| 2008/0113350 A1 | 5/2008 | Terstappen |
| 2008/0113358 A1 | 5/2008 | Kapur et al. |
| 2008/0318235 A1 | 12/2008 | Handyside |
| 2009/0215633 A1 | 8/2009 | Van Eijk et al. |
| 2009/0317836 A1 | 12/2009 | Kuhn et al. |
| 2010/0169990 A1 | 7/2010 | Clarke et al. |
| 2010/0248358 A1 | 9/2010 | Yoshioka |
| 2011/0015096 A1 | 1/2011 | Chiu et al. |
| 2013/0253369 A1 | 9/2013 | Rabinowitz et al. |
| 2014/0032128 A1 | 1/2014 | Rabinowitz et al. |
| 2014/0087385 A1 | 3/2014 | Rabinowitz et al. |
| 2014/0106975 A1 | 4/2014 | Stoughton et al. |
| 2015/0232936 A1 | 8/2015 | Shoemaker et al. |
| 2015/0344956 A1 | 12/2015 | Kapur et al. |
| 2016/0002737 A1 | 1/2016 | Fuchs et al. |

FOREIGN PATENT DOCUMENTS

| | | |
|---|---|---|
| CN | 1590563 A | 3/2005 |
| CN | 1650032 A | 8/2005 |
| EP | 0057907 | 8/1982 |
| EP | 0994963 | 4/2000 |
| EP | 1221342 | 7/2002 |
| EP | 1328803 | 9/2005 |
| EP | 1597353 | 11/2010 |
| JP | 2004351309 | 12/2004 |
| WO | WO 1993/022055 | 11/1993 |
| WO | WO 1997/32999 | 9/1997 |
| WO | WO 1998/00231 | 1/1998 |
| WO | WO 1998/31839 | 7/1998 |
| WO | WO 1998/39474 | 9/1998 |
| WO | WO 1998/57159 | 12/1998 |
| WO | WO 1999/38612 | 8/1999 |
| WO | WO 1999/58972 | 11/1999 |
| WO | WO 2000/37163 | 6/2000 |
| WO | WO 2001/37958 | 5/2001 |
| WO | WO 2002/061143 | 8/2002 |
| WO | WO 2002/073204 | 9/2002 |
| WO | WO 2003/003057 | 1/2003 |
| WO | WO 2003/040064 | 5/2003 |
| WO | WO 2003/074740 | 9/2003 |
| WO | WO 2003/078972 | 9/2003 |
| WO | WO 2003/085379 | 10/2003 |
| WO | WO 2005/068503 | 7/2005 |
| WO | WO 2005/108963 | 11/2005 |
| WO | WO 2006/020936 | 2/2006 |
| WO | WO 2006/104474 | 10/2006 |
| WO | WO 2006/104530 | 10/2006 |
| WO | WO 2006/108087 | 10/2006 |
| WO | WO 2006/108101 | 10/2006 |
| WO | WO 2007/035498 | 3/2007 |
| WO | WO 2007/035585 | 3/2007 |
| WO | WO 2007/035586 | 3/2007 |
| WO | WO 2007/053245 | 5/2007 |
| WO | WO 2007/103910 | 9/2007 |
| WO | WO 2009/009769 | 1/2009 |

OTHER PUBLICATIONS

Advisory action dated Mar. 4, 2015 for U.S. Appl. No. 12/689,548.
Amendment to the Claims dated Jun. 16, 2014 for U.S. Appl. No. 13/863,992.
Amendment to the Claims dated Dec. 5, 2013 for U.S. Appl. No. 12/751,940.
Amendments to the Claims. Filed Oct. 14, 2014 with U.S. Patent Office for U.S. Appl. No. 13/831,342.

(56) References Cited

OTHER PUBLICATIONS

Bailey et al., "Recent Segmental Duplications in the Human Genome," Science, Aug. 2002, 297: 1003-1007.
Bianchi, et al. Large amounts of cell-free fetal DNA are present in amniotic fluid. Clinical chemistry 47.10 (2001): 1867-1869.
Bischoff, et al. Cell-free fetal DNA and intact fetal cells in maternal blood circulation: implications for first and second trimester non-invasive prenatal diagnosis. Human reproduction update 8.6 (2002): 493-500.
Bischoff et al., "Intact fetal cell isolation from maternal blood: improved isolation using a simple whole blood progenitor cell enrichment approach (RosetteSep™)," Clin. Genet., vol. 63, pp. 483-489 (2003).
Breman et al., "Evidence for feasibility of fetal trophoblastic cell-based noninvasive prenatal testing," Prenatal Diagnosis, vol. 36, pp. 1009-1019 (2016).
Brown et al., "Aneuploidy detection in mixed DNA samples by methylation-sensitive amplification and microarray analysis," Clinical chemistry 56.5 (2010): 805-813.
Brown et al., "Validation of QF-PCR for prenatal aneuploidy screening in the United States," Prenatal diagnosis 26 .11 (2006): 1068-1074.
Chang et al., "Assessment of Plasma DNA Levels, Allelic Imbalance, and CA 125 as Diagnostic Tests for Cancer," Nov. 20, 2002, J, Nat'l Cancer Inst. 94(22): 1697-1703.
Chim et al., "Detection of the placental epigenetic signature of the maspin gene in maternal plasma," Proceedings of the National Academy of Sciences of the United States of America 102.41(2005): 14753-14758.
Chiu et al. Noninvasive prenatal diagnosis by analysis of fetal DNA in maternal plasma. Clinical Applications of PCR (2006): 101-109.
Christensen et al., "Sensitivity and specificity of the identification of fetal cells in maternal blood by combined staining with antibodies against beta-, gamma-and epsilon-globin chains," Fetal Diagn. Ther., vol. 18, pp. 479-484 (2003).
Coble et al. "Characterization of New MiniSTR Loci to Aid Analysis of Degraded DNA," Jan. 2005. J. Forensic Sci. 50(1):43-53.
Dahl et al., "Multigene Amplification and Massively Parallel Sequencing for Cancer Mutation Discoveiy," May 29, 2007, PNAS USA 104(22):9387-9392.
Declaration of Atul J. Butte, M.D. Ph.D. in Support of Patent Owner's Response to Inter Partes Review of U.S. Pat. No. 8,316,430. US Patent Office. dated Jan. 16, 2014.
Deposition of Dr. Cynthia Casson Morton. US Patent Office. dated Dec. 10, 2013.
Deposition of Dr. Robert Nussbaum. US Patent Office. dated Dec. 11, 2013.
Deutsch et al., "Detection of aneuploidies by paralogous sequence quantification," J Med Genet. Dec. 2004;41(12):908-15.
EP Office Action in European Appln. No. 18170287, dated Apr. 6, 2020, 8 pages.
European office action dated May 22, 2015 for EP Application No. 07798579.4.
European office action dated Aug. 22, 2013 for EP Application No. 07798579.4.
Evans et al., "Digital PCR for noninvasive detection of aneuploidy: power analysis equations for feasibility," Fetal diagnosis and therapy 31.4 (2012): 244-247.
Extended European Search Report in Application No. 18170287.9, dated Sep. 19, 2018, 10 pages.
Fan et al., "Highly Parallel Genomic Assays," Aug. 2006. Nat. Rev. Genet. 7(8):632-44.
Fiddler, "Fetal cell based prenatal diagnosis: perspectives on the present and future," J. Clin Med., vol. 3, pp. 972-985 (2014).
Geifman-Holtzman et al., "The clinical utility of fetal cell sorting to determine prenatally fetal E/e or e/e Rh genotype from peripheral maternal blood," Am. J. Obstet. Gynecol., vol. 183, pp. 462-468 (2000).
Grundevik et al., "Molecular Diagnostics of Aneuploidies. Chalmers University of Technology," May 17, 2005.
Hall, "Advanced Sequencing Technologies and their Wider Impact in Microbiology," 2007. J. Exp. Biol. 209:1518-1525.
Hatt et al., "A New Marker Set That Identifies Fetal Cells in Maternal Circulation With High Specificity," Prenatal Diagn., vol. 34, pp. 1-7 (2014).
Hua et al., "Detection of aneuploidy from single fetal nucleated red blood cells using whole genome sequencing," Prenatal Diagnosis, vol. 34, pp. 1-8 (2014).
International Preliminary Report on Patentability dated Dec. 16, 2008 for PCT Application No. US2007/071248.
Jama et al., "Quantification of cell-free DNA levels in maternal plasma by STR analysis," Mar. 24-28, 2010. ACMG Annual Clinical Genetics Meeting Poster 398. Available at http://acmg.omnibooksonline.com/2010/data/papers/398.pdf. Accessed Apr. 5, 2013.
Jauniaux et al., "Very early prenatal diagnosis on coelomic cells using quantitative fluorescent polymerase chain reaction," Reproductive BioMedicine Online, Jan. 2003, 6: 494-498.
Kaiser, "An earlier look at baby's genes," Science, 309.5740 (2005): 1476.
Karow, "Following Improvements in Noninvasive Fetal Cell Isolation, First Prenatal Tests Expected in 2016", published on Genomeweb (www.genomeweb.com/archive/following-improvements-noninvasive-fetal-cell-isolation-first-prenatal-testsexpected-2016; pp. 1-4; (Nov. 2015).
Khattabi et al., "Could Digital PCR Be an Alternative as a Non-Invasive Prenatal Test for Trisomy," 21: A Proof of Concept Study. PloS one 11.5 (2016): e0155009.
Koide et al., "Fragmentation of Cell-Free Fetal DNA in Plasma and Urine of Pregnant Women," Jul. 2005, Prenat. Diagn, 25(7):604-7.
Leary et al., "Digital karyotyping," Nature Protocols, 2007, 2: 1973-1986.
Leon et al., "Free DNA in the serum of cancer patients and the effect of therapy," Cancer Res. Mar. 1977;37(3):646-50.
Liu et al., "Feasibility Study of Using Fetal DNA in Maternal Plasma for Non-invasive Prenatal Diagnosis," Acta Obstet. Gynecol. Scand. May 2007; 86(5):535-41.
Illumina Technical Note: Reproductive Health, pp. 1-5 (2014).
Lo et al., "Increased Fetal DNA Concentrations in the Plasma of Pregnant Women Carrying Fetuses with Trisomy," Oct. 21, 1999, Clin. Chem. 45(10): 1747-51.
Lo et al., "Rapid Clearance of Fetal DNA from Maternal Plasma," Jan. 1999. Am. J. Hum. Genet. 64(1):218-24.
Iontorrent Application Note, pp. 1-6 (2016).
Mann et al., "Strategies for the rapid prenatal diagnosis of chromosome aneuploidy," European Journal of Human Genetics 12.11 (2004): 907-915.
Notice of allowance dated Jan. 22, 2016 for U.S. Appl. No. 13/837,974.
Notice of allowance dated Jan. 26, 2015 for U.S. Appl. No. 13/835,926.
Notice of allowance dated Jul. 27, 2016 for U.S. Appl. No. 12/816,043.
Notice of allowance dated Oct. 27, 2015 for U.S. Appl. No. 13/829,971.
Office action dated Jan. 26, 2015 for CA Application No. 2655272.
Office action dated Jan. 28, 2014 for U.S. Appl. No. 13/835,926.
Office action dated Jan. 30, 2014 for U.S. Appl. No. 13/837,974.
Office action dated Feb. 5, 2014 for U.S. Appl. No. 12/689,517.
Office action dated Feb. 23, 2015 for U.S. Appl. No. 12/689,517.
Office action dated Mar. 11, 2015 for U.S. Appl. No. 13/737,730.
Office action dated Mar. 14, 2016 for U.S. Appl. No. 12/816,043.
Office action dated Mar. 15, 2016 for U.S. Appl. No. 12/751,940.
Office action dated Mar. 20, 2014 for U.S. Appl. No. 12/816,043.
Office action dated Mar. 21, 2014 for U.S. Appl. No. 12/815,674.
Office action dated Mar. 31, 2016for U.S. Appl. No. 13/863,992.
Office action dated Apr. 7, 2015 for U.S. Appl. No. 13/829,971.
Office action dated Apr. 28, 2014 for U.S. Appl. No. 12/689,548.
Office action dated Apr. 29, 2015 for U.S. Appl. No. 13/794,503.
Office action dated May 8, 2015 for U.S. Appl. No. 12/816,043.
Office action dated May 11, 2015 for U.S. Appl. No. 13/863,992.
Office action dated Jul. 16, 2015 for U.S. Appl. No. 13/837,974.

(56) References Cited

OTHER PUBLICATIONS

Office action dated Jul. 21, 2015 for U.S. Appl. No. 12/689,548.
Office action dated Jul. 29, 2014 for U.S. Appl. No. 13/835,926.
Office action dated Aug. 1, 2014 for U.S. Appl. No. 12/816,043.
Office action dated Aug. 16, 2016 for U.S. Appl. No. 13/863,992.
Office action dated Aug. 19, 2015 for U.S. Appl. No. 12/689,517.
Office action dated Aug. 29, 2014 for U.S. Appl. No. 13/837,974.
Office action dated Sep. 16, 2016 for U.S. Appl. No. 12/689,517.
Office action dated Sep. 17, 2014 for U.S. Appl. No. 13/863,992.
Office action dated Sep. 18, 2015 for U.S. Appl. No. 12/816,043.
Office action dated Nov. 7, 2014 for U.S. Appl. No. 13/831,342.
Office action dated Nov. 24, 2014 for U.S. Appl. No. 12/689,548.
Office action dated Dec. 1, 2016 for U.S. Appl. No. 13/794,503.
Office action dated Dec. 10, 2014 for U.S. Appl. No. 12/751,940.
Office action dated Dec. 12, 2014 for U.S. Appl. No. 13/738,268.
Office action dated Dec. 22, 2015 for U.S. Appl. No. 13/794,503.
Office action dated Dec. 27, 2016 for U.S. Appl. No. 13/863,992.
Opposition dated Apr. 10, 2014 by Olswang against EP Application No. EP07763674.4.
Opposition dated Jun. 12, 2015 by Premaitha Health PLC against EP Application No. EP07763674.4.
Pathak et al., "Circulating Cell-Free DNA in Plasma/Serum of Lung Cancer Patients as a Potential Screening and Prognostic Tool," Oct. 2006, Clin. Chem. 52(10): 1833-42.
Pertl et al., "Detection of Male and Female DNA in Maternal Plasma by Multiplex Fluorescent Polymerase Chain Reaction Amplification of Short Tandem Repeats," Jan. 2000. Hum. Genet. 106(1):45-9.
Poon et al., "Differential DNA methylation between fetus and mother as a strategy for detecting fetal DNA in maternal plasma," Clinical chemistry 48.1 (2002): 35-41.
REPLI-g® Mini and Midi Kits pamphlet from Qiagen (Oct. 2005).
Sekiza et al., "Recent advances in non-invasive prenatal DNA diagnosis through analysis of maternal blood," Journal of Obstetrics and Gynaecology Research, 33.6 (2007): 747-764.
Su et al., "Human Urine Contains Small, 150 to 250 Nucleotide-Sized, Soluble DNA Derived from the Circulation and may be Useful in the Detection of Colo rectal Cancer," May 2005, J. Mol. Diagn. 6(2):101-7.
Swarup et al., "Circulating (cell free) nucleic acids—A promising, non-invasive tool for early detection of several human diseases," 2007 FEBS Letters 581 :795-799.
Thomas et al., "Sensitive Mutation Detection in Heterogeneous Cancer Specimens by Massively Parallel Picoliter Reactor Sequencing," Jul. 2006. Nature Medicine. 12(7):852-855.
Tong et al., "Noninvasive prenatal detection of fetal trisomy 18 by epigenetic allelic ratio analysis in maternal plasma: theoretical and empirical considerations," Clinical Chemistry 52.12 (2006): 2194-2202.
Vogelstein et al., "Allelotype of colorectal carcinomas," Science 244 (4): 207-211. 1989.
Vona et al., "Enrichment, immunomorphological, and genetic characterization of fetal cells circulating in maternal blood," Am. J. Pathol., vol. 160, pp. 51-58 (2002).
Wang et al., "Digital karyotyping," PNAS, Dec. 2002, 99: 16156-16161.
Wang et al., "Advances and applications of single-cell sequencing technologies," Mol. Cell, vol. 58, pp. 598-609 (2015).
Wong et al., "Circulating placental RNA in maternal plasma is associated with a preponderance of 5' mRNA fragments: implications for noninvasive prenatal diagnosis and monitoring," Clinical chemistry 51.10 (2005): 1786-1795.
Wright et al., "The use of cell-free fetal nucleic acids in maternal blood for noninvasive prenatal diagnosis," Hum. Reprod. Update. Jan.-Feb. 2009;15(1):139-51.
Yu et al., "Size-based molecular diagnostics using plasma DNA for noninvasive prenatal testing," Proceedings of the National Academy of Sciences 111.23 (2014): 8583-8588.
Zhang et al., "Whole genome amplification from a single cell: implications for genetic analysis," Proc Natl Acad Sci US A Jul. 1, 1992;89(13):5847-51.
Zhou et al., "Counting alleles reveals a connection between chromosome 18q loss and vascular invasion," Nature biotechnology 19 .1 (2001 ): 78-81.
Zhou et al., "Counting alleles to predict recurrence of early-stage colorectal cancers," The Lancet 359.9302 (2002): 219-225.
Zimmerman, et al., "Digital PCR: a powerful new tool for noninvasive prenatal diagnosis?," 2008 Prenat Diagn 28, 1087-1093.
[No. Author Listed] "REPLI-g® Mini and Midi Kits: For highly uniform whole genome amplification from small or precious samples," Qiagen, Oct. 2005, 4 pages.
Aggarwal et al., "A combinatorial approach to the selective capture of circulating malignant epithelial cells by peptide ligands," Biomaterials, 2005, 26(30):6077-86.
Andre et al., "Lectin-Mediated Drug Targeting: Selection of Valency, Sugar Type (Gal/Lac), and Spacer Length for Cluster Glycosides as Parameters to Distinguish Ligand Binding to C-Type Asialoglycoprotein Receptors and Galectins," Pharmaceutical Research, 2000, 17(8):985-990.
Archer et al., "Cell Reactions to Dielectrophoretic Manipulation," Biochemical and Biophysical Research Communications, 1999, 257:687-698.
AU Notice of Acceptance in Australian Application No. 2013204127, dated Jul. 7, 2015, 3 pages.
Benincasa et al., "Cell Sorting by One Gravity SPLITT Fractionation," Analytical Chemistry, 2005, 77(16):5294-5301.
Birner et al., "Evaluation of the United States Food and Drug Administration-approved scoring and test system of HER-2 protein expression in breast cancer," Clin Cancer Res., 2001 7(6): 1669-1675.
Chiu et al., "Noninvasive prenatal diagnosis by analysis of fetal DNA in maternal plasma," Methods Mol Biol., 2006, 336:101-109.
CN Office Action in Chinese Appln. No. 201711191019.9, dated Oct. 22, 2020, 13 pages (with English translation).
Dhallan et al., "A non-invasive test for prenatal diagnosis based on fetal DNA present in maternal blood: apreliminaiy study," Lancet, 2007, 369(9560):474-481.
EP Extended European Search Report in Application No. 18171950.1, dated Oct. 15, 2018, 8 pages.
EP Extended European Search Report in European Appln. No. 12175907.0, dated Jan. 2, 2013, 11 pages.
EP Office Action in European Appln No. 07784444.7, dated Aug. 2, 2010, 6 pages.
EP Office Action in European Appln. No. 07763674.4, dated Mar. 3, 2009, 3 pages.
EP Office Action in European Appln. No. 07784444.7, dated Apr. 4, 2012, 7 pages.
EP Office Action in European U.S. Appl. No. 18170287, dated Feb. 22, 2021, 7 pages.
EP Office Action in European Appln. No. 18171950.1, dated Apr. 7, 2020, 6 pages.
Pending Claims filed with the USPTO in U.S. Appl. No. 11/701,686, filed Jun. 24, 2010, 6 pages.
Notice of Allowance in U.S. Appl. No. 12/393,803, dated Jul. 12, 2011, with allowed claims, 11 pages.
Office Action in U.S. Appl. No. 11/067,102, dated Aug. 1, 2008, 24 pages.
Office Action in U.S. Appl. No. 11/067,102, dated Apr. 13, 2009, 22 pages.
Office Action in U.S. Appl. No. 11/067,102, dated Feb. 4, 2010, 21 pages.
Office Action in U.S. Appl. No. 11/067,102, dated Jun. 15, 2007, 18 pages.
Office Action in U.S. Appl. No. 11/067,102, dated Sep. 17, 2010, 31 pages.
Office Action in U.S. Appl. No. 11/763,426, dated Jun. 14, 2010, 14 pages.
FDA.gov [online], "Premarket Approval Decisions for Sep. 1998," available on or before Oct. 16, 1998, via Internet Archive: Wayback

(56) References Cited

OTHER PUBLICATIONS

Machine URL <http://web.archive.org/web/19990507012424/http://www.fda.gov/cdrh/pma/pmasep98.html>, retrieved on May 28, 2021, URL http://www.fda.gov/cdrh/pma/pmasep98.html>, 12 pages.

Hatch et al., "A rapid diffusion immunoassay in a T-sensor," Nature Biotechnology, 2001, 19:461-465.

Jayasena, "Aptamers: an emerging class of molecules that rival antibodies in diagnostics," Clin Chem., 1999, 45(9): 1628-1650.

Kim et al., "rSW-seq: algorithm for detection of copy number alterations in deep sequencing data," BMC Bioinformatics, 2010, 11:432, 13 pages.

Meng et al., "HER-2 gene amplification can be acquired as breast cancer progresses," PNAS, 2004, 101:9393-9398.

Scoazec, "Tissue and cell imaging in situ: potential for applications in pathology and endoscopy," Gut, 2003, 52(Suppl 4):iv1-iv6.

Solexa, "Protocol for whole genome digital expression profiling using Solexa Technology," Biotechniques, Protocol Guide, 2007, 1 page.

Voldman et al., "Holding Forces of Single-Particle Dielectrophoretic Traps," Biophysical Journal, 2001,80:531-541.

Vona et al., "Isolation by size of epithelial tumor cells," American Journal of Pathology, 2000, 156:57-63.

Xu et al., "Dielectrophoresis of human red cells in microchips," Electrophoresis, 1999, 20:1829-1831.

Yang et al., "Prenatal diagnosis of trisomy 21 with fetal cells i maternal blood using comparative genomic hybridization," Fetal Diagn Ther., 2006, 21:125-133.

Zborowski et al., "Red Blood Cell Magnetophoresis," Biophys. J., 2003, 84:2638-2645.

Zhang et al., "Whole genome amplification from a single cell: Implications for genetic analysis," PNAS, 1992, 89:5847-5851.

EP Intention to Grant in European Appln. No. 18171950.1, dated Dec. 23, 2021, 5 pages.

EP Summons to attend oral proceedings pursuant to Rule 115(1) EPC in European Appln. No. 18171950.1, dated Mar. 3, 2021, 9 pages.

\* cited by examiner

Microposts and cells

Antibody coated posts

FIG. 9A
FIG. 9B
FIG. 9C
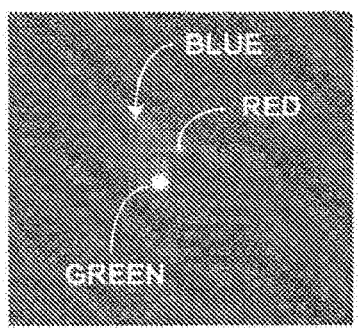
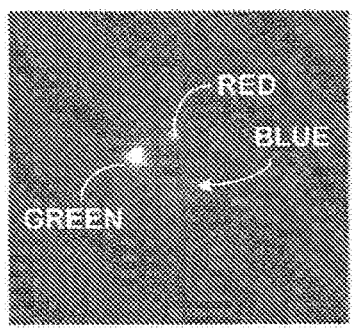
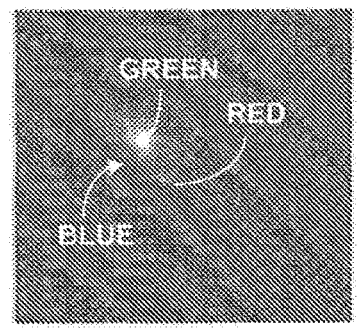
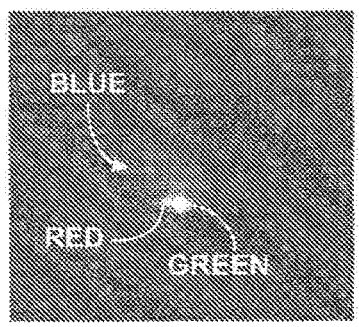
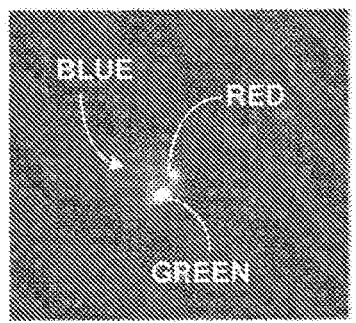
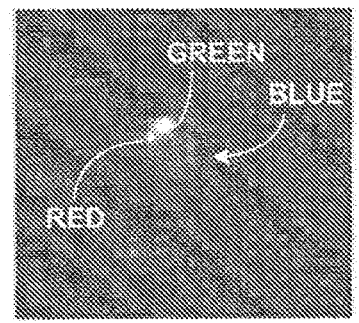
FIG. 9D
FIG. 9E
FIG. 9F
(Blue= nucleus, Red = X chromosome, Green = Y chromosome)

| Locus | Chromosomal Position |
|---|---|
| F13B | 1 q31-q32.1 |
| TPOX | 2 p23-2pter |
| FIBRA (FGA) | 4 q28 |
| CSF1PO | 5 q33.3-q34 |
| F13A | 6 p24-p25 |
| TH01 | 11 p15-15.5 |
| VWA | 12 p12-pter |
| CD4 | 12 p12-pter |
| D14S1434 | 14 q32.13 |
| CYAR04 (P450) | 15 q21.1 |
| D21S11 | 21 q11-q21 |
| D22S1045 | 22 q12.3 |

STR loci used for fetal cell detection

FIG. 12

| Oligo Name | Sequence (5'-3') | bp | Eppendorf Annealing Temp |
|---|---|---|---|
| 14S1434_F03 (SEQ ID NO. 111) | TTC TAA TAT GCA AAT GCA CAC AGA TTT CTG CT | 32 | 68 C |
| 14S1434_R03 (SEQ ID NO. 112) | TTC AGA TTC AGA CTG AAT GAC ACC ATC AGT TT | 32 | 68 C |
| CD4F_01 (SEQ ID NO. 113) | TTG GAG TCG CAA GCT GAA CTA GCG | 24 | 68 C |
| CD4R_01 (SEQ ID NO. 114) | CCA GGA AGT TGA GGG TGC AGT GAA | 24 | 68 C |
| CSF1PO_F02 (SEQ ID NO. 115) | TAA AGT GAG AAA GAA TAA CTG CAT CTT AAC CT | 32 | 68 C |
| CSF1PO_R02 (SEQ ID NO. 116) | TCT CCT TTC TCT TCC TCA TCC CTG CAT | 27 | 68 C |
| CYAR04_F02 (SEQ ID NO. 117) | GCT CTG GAA AAC TGG ACC CTT CTT | 27 | 68 C |
| CYAR04_R02 (SEQ ID NO. 118) | GTG GGA GAA TCG CCT GAG TCC T | 22 | 68 C |
| D21S11_F02 (SEQ ID NO. 119) | GTC TGT TAT GGG ACT TTT CTC AGT CTC CAT | 30 | 68 C |
| D21S11_R02 (SEQ ID NO. 120) | ACA CTG AGA AGG GAG AAA CAC TGT AAG GTT TTA TAT | 36 | 68 C |
| D22S1045F_01 (SEQ ID NO. 121) | GCT AGA TTT TCC CCG ATG AT | 20 | 68 C |
| D22S1045R_01 (SEQ ID NO. 122) | ATG TAA AGT GCT CTC AAG AGT GC | 23 | 68 C |
| F13A_F02 (SEQ ID NO. 123) | GCA TGC ACC TGT AGT TCC AGC TAC T | 25 | 68 C |
| F13A_R02 (SEQ ID NO. 124) | GAG AGC AAC GTG TCC CTC CTG T | 22 | 68 C |
| F13B_F02 (SEQ ID NO. 125) | CAG AAG AGA CTG CCC TTC AGA CTT TCT AAA T | 31 | 68 C |
| F13B_R02 (SEQ ID NO. 126) | GTA CAC GCC TGT AAT CCC AGC TAC T | 25 | 68 C |
| FIBRA_F02 (SEQ ID NO. 127) | TAC ACC TTT AAA ATT CCA AAG AAA GTT CTT CT | 32 | 68 C |
| FIBRA_R02 (SEQ ID NO. 128) | CAA TTC TGC TTC TCA GAT CCT CTG ACA CT | 29 | 68 C |
| THO1_F02 (SEQ ID NO. 129) | CCA AGG CCC TTC CCA GGC T | 19 | 68 C |
| THO1_R02 (SEQ ID NO. 130) | TGA CAG TGC TAC AAC TCA CAC CAC ATT T | 28 | 68 C |
| TPOX_F02 (SEQ ID NO. 131) | AAG CCA TGT TCC TAC CAG TGG CCT | 21 | 68 C |
| TPOX_R02 (SEQ ID NO. 132) | CAA ACG TGA GGT TGA CTG CTG TAC TGT CCT | 27 | 68 C |
| VWA_F02 (SEQ ID NO. 133) | AGA CTG ATC CTA TAA GGT AGA GTT CCC ACC T | 31 | 68 C |
| VWA_R02 (SEQ ID NO. 134) | TAG AGA CAG GAT AGA TGA TAA ATA GAT ACA TAG GTT | 36 | 68 C |

EXTERNAL PRIMERS FOR STR LOCI

FIG. 13

| Oligo Name | Sequence (5'-3') | bp | Product lengths | Eppendorf Annealing Temp |
|---|---|---|---|---|
| CD4F_02 (SEQ ID NO. 135) | TTG GAG TCG CAA GCT GAA CTA GC | 23 | 86-141 | 63C |
| CD4R_02 (SEQ ID NO. 136) | GCC TGA GTG ACA GAG TGA GAA CC | 23 | 86-141 | 63C |
| D14S1434F_02 (SEQ ID NO. 137) | TGT AAT AAC TCT ACG ACT GTC TGT CTG | 27 | 70-102 | 63C |
| D14S1434R_02 (SEQ ID NO. 138) | GAA TAG GAG GTG GAT GGA TGG | 21 | 70-102 | 63C |
| D21S11_F01 (SEQ ID NO. 139) | GTG AGT CAA TTC GCC AAG | 18 | 202-265 | 63C |
| D21S11_R01 (SEQ ID NO. 140) | GTT GTA TTA GTC AAT GTT CTC C | 22 | 202-265 | 63C |
| D22S1045F_02 (SEQ ID NO. 141) | ATT TTC CCC GAT GAT GAT AGT AGT CT | 23 | 76-109 | 63C |
| D22S1045R_02 (SEQ ID NO. 142) | GCG AAT GTA TGA TTG GCA ATA TTT TT | 26 | 76-109 | 63C |
| F13B_F01 (SEQ ID NO. 143) | TGA GGT GGT GTA CTA CCA TA | 20 | 169-193 | 63C |
| F13B_R01 (SEQ ID NO. 144) | GAT CAT GCC ATT GCA CTC TA | 20 | 169-193 | 63C |
| VWA_F01 (SEQ ID NO. 145) | CCC TAG TGG ATG AGA ATA AGA ATA ATC | 24 | 122-182 | 63C |
| VWA_R01 (SEQ ID NO. 146) | GGA CAG ATG ATA ATA ACA TAG GAT GGA TGG | 30 | 122-182 | 63C |
| CSF1PO_F01 (SEQ ID NO. 147) | TTC CAC ACA CCA CTG GCC ATC TTC | 24 | 295-327 | 68C |
| CSF1PO_R01 (SEQ ID NO. 148) | AAC CTG AGT CTG CCA AGG ACT AGC | 24 | 295-327 | 68C |
| CYAR04_F01 (SEQ ID NO. 149) | GGT AAG CAG GTA CTT AGT TAG CTA C | 25 | 172-205 | 68C |
| CYAR04_R01 (SEQ ID NO. 150) | GTT ACA GTG AGC CAA GGT CGT GAG | 24 | 172-205 | 68C |
| F13A1_F01 (SEQ ID NO. 151) | GAG GTT GCA CTC GAG CCT TTG CAA | 24 | 279-335 | 68 - 63C |
| F13A1_R01 (SEQ ID NO. 152) | TTC CTG AAT CAT CCC AGA GCC ACA | 24 | 279-335 | 68 - 63C |
| FIBRA_F01 (SEQ ID NO. 153) | ATT ATC CAA AAG TCA AAT GCC CCA TAG G | 28 | 158-286 | 68C |
| FIBRA_R01 (SEQ ID NO. 154) | ATC GAA AAT ATG GTT ATT GAA GTA GCT G | 28 | 158-286 | 68C |
| TH01_F01 (SEQ ID NO. 155) | GTG GGC TGA AAA GCT CCC GAT TAT | 24 | 171-215 | 68C |
| TH01_R01 (SEQ ID NO. 156) | ATT CAA AGG GTA TCT GGG CTC TGG | 24 | 171-215 | 68C |
| TPOX_F01 (SEQ ID NO. 157) | ACT GGC ACA GAA CAG GCA CTT AGG | 24 | 220-256 | 68C |
| TPOX_R01 (SEQ ID NO. 158) | GGA GGA ACT GGG AAC CAC ACA GGT | 24 | 220-256 | 68C |

INTERNAL PRIMERS FOR STRs LOCI

FIG. 14

DIAGNOSIS OF FETAL ABNORMALITIES USING POLYMORPHISMS INCLUDING SHORT TANDEM REPEATS

CROSS-REFERENCE

This application is a Continuation of U.S. application Ser. No. 13/830,871, filed on Mar. 14, 2013; which is a Continuation of U.S. application Ser. No. 13/738,268 filed Jan. 10, 2013; which is a Continuation of U.S. application Ser. No. 13/433,232 filed on Mar. 28, 2012; which is a Continuation of U.S. application Ser. No. 12/725,240 filed on Mar. 16, 2010; which is a Continuation of U.S. application Ser. No. 11/763,426 filed on Jun. 14, 2007; which claims the benefit of U.S. Provisional Application Ser. No. 60/820,778 filed on Jul. 28, 2006 and U.S. Provisional Application No. 60/804,815, filed Jun. 14, 2006, which application is incorporated herein by reference.

BACKGROUND OF THE INVENTION

Analysis of specific cells can give insight into a variety of diseases. These analyses can provide non-invasive tests for detection, diagnosis and prognosis of diseases, thereby eliminating the risk of invasive diagnosis. For instance, social developments have resulted in an increased number of prenatal tests. However, the available methods today, amniocentesis and chorionic villus sampling (CVS) are potentially harmful to the mother and to the fetus. The rate of miscarriage for pregnant women undergoing amniocentesis is increased by 0.5-1%, and that figure is slightly higher for CVS. Because of the inherent risks posed by amniocentesis and CVS, these procedures are offered primarily to older women, i.e., those over 35 years of age, who have a statistically greater probability of bearing children with congenital defects. As a result, a pregnant woman at the age of 35 has to balance an average risk of 0.5-1% to induce an abortion by amniocentesis against an age related probability for trisomy 21 of less than 0.3%.

To eliminate the risks associated with invasive prenatal screening procedures, non-invasive tests for detection, diagnosis and prognosis of diseases, have been utilized. For example, maternal serum alpha-fetoprotein, and levels of unconjugated estriol and human chorionic gonadotropin are used to identify a proportion of fetuses with Down's syndrome, however, these tests are not one hundred percent accurate. Similarly, ultrasonography is used to determine congenital defects involving neural tube defects and limb abnormalities, but is useful only after fifteen weeks' gestation.

The methods of the present invention allow for the detection of fetal cells and fetal abnormalities when fetal cells are present in a mixed population of cells, even when maternal cells dominate the mixture.

SUMMARY OF THE INVENTION

The presence of fetal cells in maternal circulation offers the opportunity to develop a prenatal diagnostic that obviates the risk associated with today's invasive diagnostics procedures. However, fetal cells are rare as compared to the presence of maternal cells in the blood. Therefore, any proposed analysis of fetal cells to diagnose fetal abnormalities requires enrichment of fetal cells. Enriching fetal cells from maternal peripheral blood is challenging, time intensive and any analysis derived therefrom is prone to error. The present invention addresses these challenges.

The present invention relates to methods for determining the presence of fetal cells and fetal abnormalities when fetal cells are present in a mixed sample (e.g. maternal blood sample). In some embodiments, determining the presence of fetal cells or of a fetal abnormality includes comparing the level of genomic DNA from a mixed sample to the level of genomic DNA in a control sample. The control or reference sample can be a mixed sample that has been sufficiently diluted to be free of fetal cells. The mixed sample can contain at least one fetal cell and one non-fetal cell. In other embodiments, the sample comprises up to 50% fetal cells.

In some embodiments, determining the presence of fetal cells and/or abnormalities involves quantifying one or more regions of genomic DNA regions from the mixed sample and determining from the quantification the presence of a fetal abnormality. Preferably, such regions are polymorphic e.g. short tandem repeat (STR) regions.

Examples of fetal abnormalities that can be determined by quantifying regions on one or more chromosomes include trisomy 13, trisomy 18, trisomy 21 (Down Syndrome), Klinefelter Syndrome (XXY) and other irregular number of sex or autosomal chromosomes. Other examples of abnormal fetal genotypes that can be determined by quantifying regions on one or more chromosomes include, but are not limited to, aneuploidy such as, monosomy of one or more chromosomes (X chromosome monosomy, also known as Turner's syndrome), trisomy of one or more chromosomes (such as 13, 18, 21, and X), tetrasomy and pentasomy of one or more chromosomes (which in humans is most commonly observed in the sex chromosomes, e.g. XXXX, XXYY, XXXY, XYYY, XXXXX, XXXXY, XXXYY, XYYYY and XXYYY), triploidy (three of every chromosome, e.g. 69 chromosomes in humans), tetraploidy (four of every chromosome, e.g. 92 chromosomes in humans) and multiploidy. In some embodiments, an abnormal fetal genotype is a segmental aneuploidy. Examples of segmental aneuploidy include, but are not limited to, 1p36 duplication, dup(17)(p11.2p11.2) syndrome, Down syndrome, Pelizaeus-Merzbacher disease, dup(22)(q11.2q11.2) syndrome, and cat-eye syndrome. In some cases, an abnormal fetal genotype is due to one or more deletions of sex or autosomal chromosomes, which may result in a condition such as Cri-du-chat syndrome, Wolf-Hirschhorn, Williams-Beuren syndrome, Charcot-Marie-Tooth disease, Hereditary neuropathy with liability to pressure palsies, Smith-Magenis syndrome, Neurofibromatosis, Alagille syndrome, Velocardiofacial syndrome, DiGeorge syndrome, Steroid sulfatase deficiency, Kallmann syndrome, Microphthalmia with linear skin defects, Adrenal hypoplasia, Glycerol kinase deficiency, Pelizaeus-Merzbacher disease, Testis-determining factor on Y, Azospermia (factor a), Azospermia (factor b), Azospermia (factor c), or 1p36 deletion. In some embodiments, a decrease in chromosomal number results in an XO syndrome.

Furthermore, the methods herein can distinguish maternal trisomy from paternal trisomy, and total aneuploidy from segmental aneuploidy. Segmental aneuploidies can be caused by an intra-chromosomal event such as a deletion, duplication or translocation event. Additionally, the methods herein can be used to identify monoploidy, triploidy, tetraploidy, pentaploidy and other higher multiples of the normal haploid state. In some embodiments, the maternal or paternal origin of the fetal abnormality can be determined.

The genomic DNA region(s) can be quantified by amplifying the regions using, for example, PCR, or preferably quantitative PCR. Alternatively, quantification of the regions can be achieved using capillary gel electrophoresis (CGE).

In some embodiments, total genomic DNA is pre-amplified prior to the quantitative amplification step to increase the overall abundance of DNA. Such pre-amplification step can involve the use of multiple displacement amplification.

In some embodiments the genomic DNA regions quantified can be in one chromosome or in 2 or more chromosomes. The polymorphic regions can be quantified on either or both sex chromosomes X and Y, and on autosomal chromosomes including chromosomes 13, 18 and 21.

Prior to analysis a mixed sample suspected of having fetal cells (e.g. a maternal blood sample) can be enriched for fetal cells. Fetal cell enrichment can be accomplished using any method known in the art including size-based separation, affinity (e.g. magnetic) separation, FACS, laser microdisection, and magnetic bead separation. A mixed sample containing as few as 10 fetal cells can be enriched. In some embodiments, the fetal cells in the enriched sample constitute less than 50% of the total number of cells.

In some embodiments, the size-based separation method includes applying a mixed sample into a system that separates a first component of the mixed sample (e.g. fetal cells), which comprises cells that are larger than a critical size, in a first direction, and a second component of the mixed sample (e.g. enucleated maternal red blood cells), which comprises cells that are smaller than a critical size, towards a second exit port. The separation system can be a device that includes one or more arrays of obstacles that form a network of gaps.

In some embodiments, enrichment that is achieved by size-based separation is followed by one or more additional enrichment procedures including magnetic separation, fluorescence activated cell sorting (FACS), laser microdisection, and magnetic bead separation. In some embodiments, a sample enriched by size-based separation is subjected to affinity/magnetic separation and is further enriched for rare cells using fluorescence activated cell sorting (FACS) or selective lysis of a subset of the cells (e.g. fetal cells).

In some embodiments there are provided kits for detecting the fetal abnormalities wherein the kits include separation devices and the reagents needed to perform the genetic analysis. For example, the kit may include arrays for size based enrichment, a device for magnetic enrichment and reagents for performing PCR.

The methods can further comprise inputting the data from the quantification step into data model(s) for the association of DNA quantity with maternal and non-maternal alleles. The invention provides for a computer program product, which includes a computer executable logic recorded on a computer readable medium that can be used for diagnosing a fetal abnormality. The computer program is designed to receive data from one of more quantified DNA genomic regions from a mixed sample containing at least one fetal cell, determine the presence or absence of a fetal abnormality from the data, and generate an output that comprises the evaluation of the fetal abnormality. Methods for using the computer program product are also disclosed.

SUMMARY OF THE DRAWINGS

The novel features of the invention are set forth with particularity in the appended claims A better understanding of the features and advantages of the present invention will be obtained by reference to the following detailed description that sets forth illustrative embodiments, in which the principles of the invention are utilized, and the accompanying drawings of which:

FIGS. 9A-9F illustrate isolated fetal cells confirmed by the reliable presence of male Y chromosome.

FIG. 12 illustrates a table with STR loci that can be used for fetal detection.

FIG. 13 illustrates a table with exemplary external primers for STR loci.

FIG. 14 illustrates a table with exemplary internal primers for STR loci.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

The present invention provides systems, apparatuses, and methods to detect the presence and condition (e.g. aneuploidy) of fetal cells in a mixed cell population, e.g. a sample wherein fetal cells consist of <50%, 45%, 40%, 35%, 30%, 25%, 20%, 15%, 10%, 5%, 1%, or 0.5% of all cells in a mixed sample.

Figure 1:
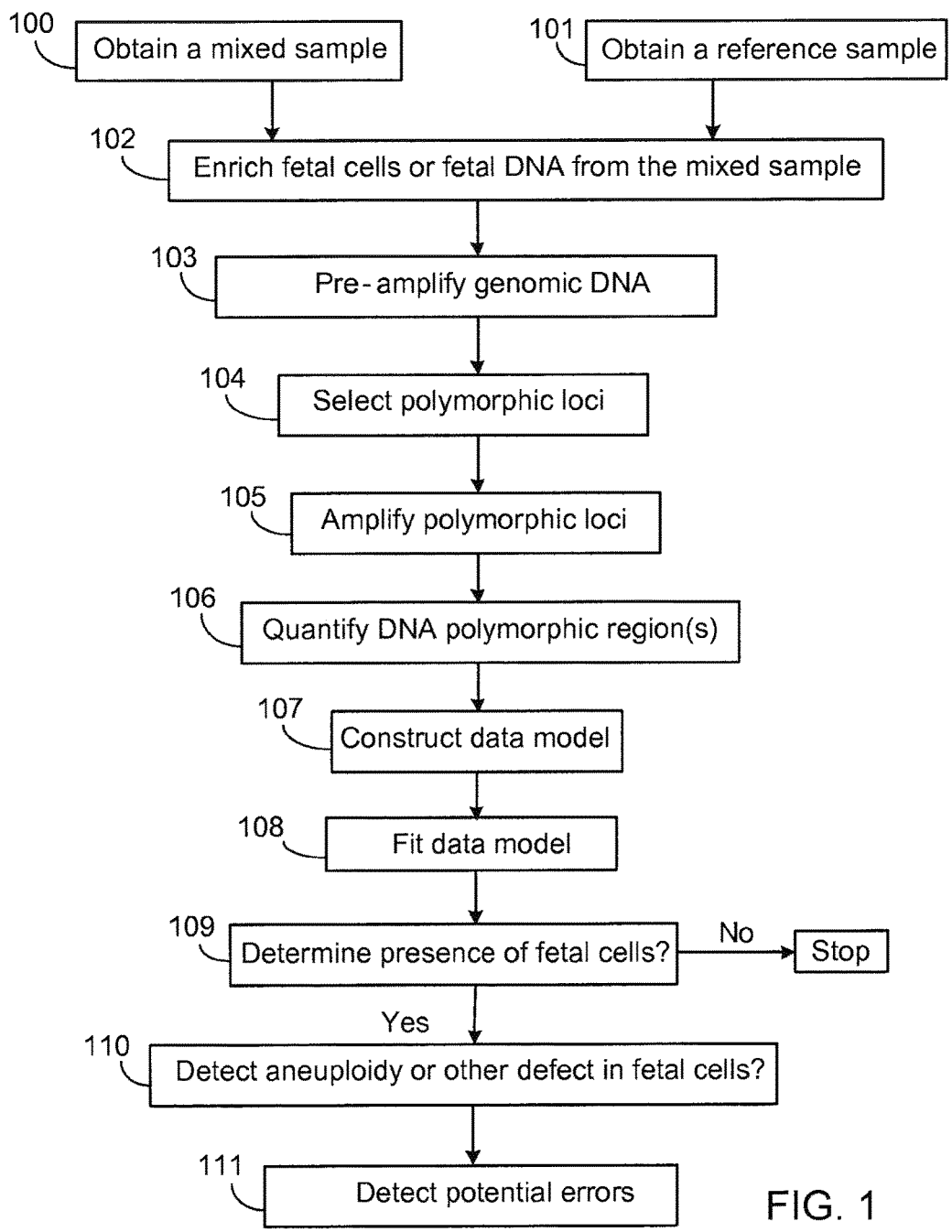
FIG. 1 illustrates a flow chart of one embodiment of the present invention.
Figure 2A:
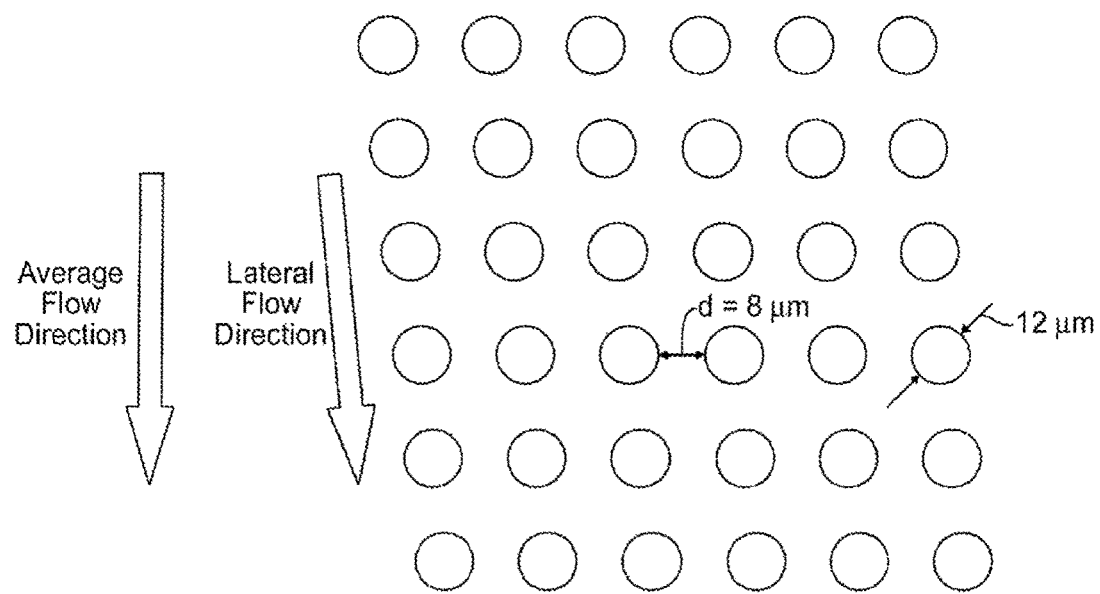
FIGS. 2A-2D illustrate one embodiment of a size-based separation module.
Figure 2B:
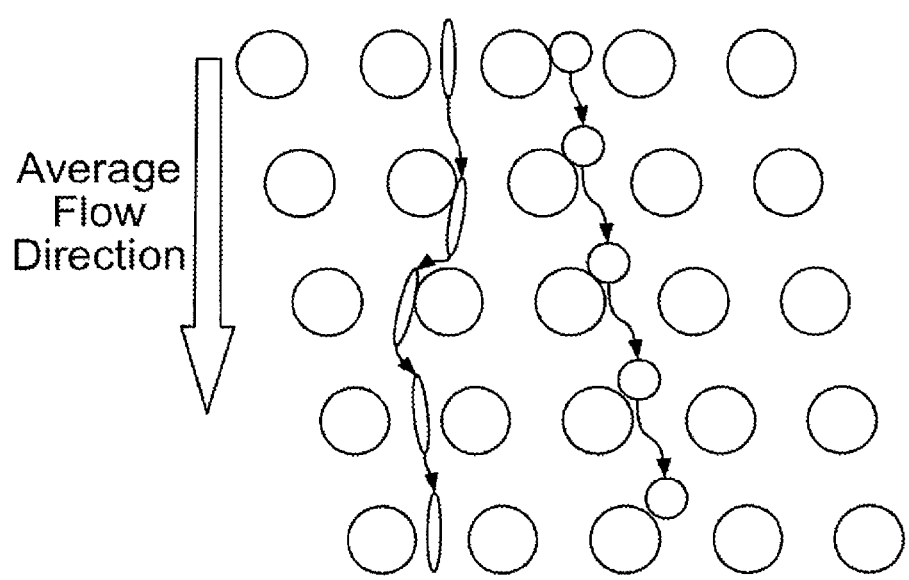
Figure 2C:
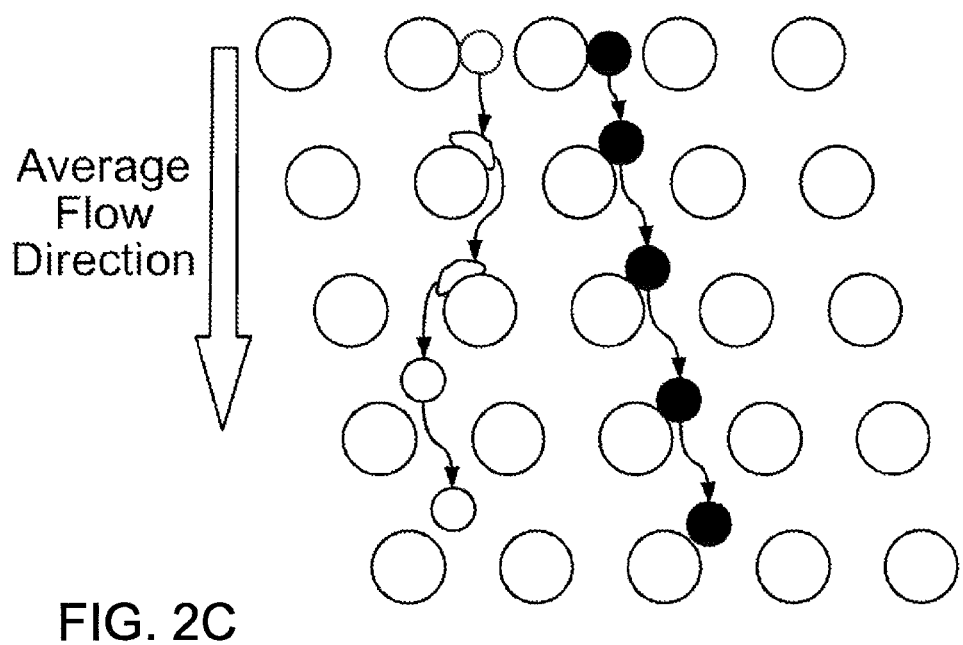
Figure 2D:
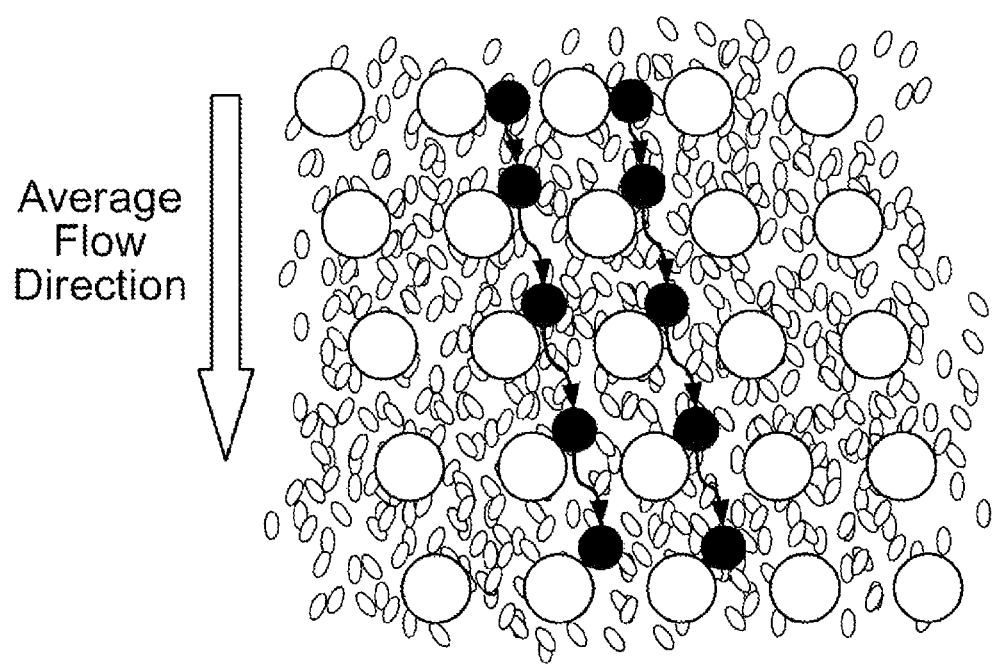

FIG. 1 illustrates an overview of one embodiment of the present invention.

In step 100, a sample containing (or suspected of containing) 1 or more fetal cells is obtained. Samples can be obtained from an animal suspected of being pregnant, pregnant, or that has been pregnant to detect the presence of a fetus or fetal abnormality. Such animal can be a human or a domesticated animal such as a cow, chicken, pig, horse, rabbit, dog, cat, or goat. Samples derived from an animal or human can include, e.g., whole blood, sweat, tears, ear flow, sputum, lymph, bone marrow suspension, lymph, urine, saliva, semen, vaginal flow, cerebrospinal fluid, brain fluid, ascites, milk, secretions of the respiratory, intestinal or genitourinary tracts fluid.

To obtain a blood sample, any technique known in the art may be used, e.g. a syringe or other vacuum suction device. A blood sample can be optionally pre-treated or processed prior to enrichment. Examples of pre-treatment steps include the addition of a reagent such as a stabilizer, a preservative, a fixant, a lysing reagent, a diluent, an anti-apoptotic reagent, an anti-coagulation reagent, an anti-thrombotic reagent, magnetic property regulating reagent, a buffering reagent, an osmolality regulating reagent, a pH regulating reagent, and/or a cross-linking reagent.

When a blood sample is obtained, a preservative such an anti-coagulation agent and/or a stabilizer can be added to the sample prior to enrichment. This allows for extended time for analysis/detection. Thus, a sample, such as a blood sample, can be enriched and/or analyzed under any of the methods and systems herein within 1 week, 6 days, 5 days, 4 days, 3 days, 2 days, 1 day, 12 hrs, 6 hrs, 3 hrs, 2 hrs, or 1 hr from the time the sample is obtained.

In some embodiments, a blood sample can be combined with an agent that selectively lyses one or more cells or components in a blood sample. For example, fetal cells can be selectively lysed releasing their nuclei when a blood sample including fetal cells is combined with deionized water. Such selective lysis allows for the subsequent enrichment of fetal nuclei using, e.g., size or affinity based separation. In another example, platelets and/or enucleated red blood cells are selectively lysed to generate a sample enriched in nucleated cells, such as fetal nucleated red blood cells (fnRBC) and maternal nucleated blood cells (mnBC). The fnRBC's can subsequently be separated from the mnBC's using, e.g., affinity to antigen-i or magnetism differences in fetal and adult hemoglobin.

When obtaining a sample from an animal (e.g., blood sample), the amount can vary depending upon animal size, its gestation period, and/or the condition being screened. In some embodiments, up to 50, 40, 30, 20, 10, 9, 8, 7, 6, 5, 4, 3, 2, or 1 mL of a sample is obtained. In some embodiments, 1-50, 2-40, 3-30, or 4-20 mL of sample is obtained. In some embodiments, more than 5, 10, 15, 20, 25, 30, 35, 40, 45, 50, 55, 60, 65, 70, 75, 80, 85, 90, 95 or 100 mL of a sample is obtained.

To detect fetal abnormality, a blood sample can be obtained from a pregnant animal or human within 36, 24, 22, 20, 18, 16, 14, 12, 10, 8, 6 or 4 weeks of gestation.

In step 101, a reference sample is obtained. The reference sample consists of substantially all or all maternal cells. In some embodiments, a reference sample is a maternal blood sample enriched for white blood cells (WBC's) such that it consists of substantially all or all maternal WBC's. In some embodiments, a reference sample is a diluted mixed sample wherein the dilution results in a sample free of fetal cells. For example, a maternal blood sample of 10-50 ML can be diluted by at least 2, 5, 10, 20, 50, or 100 fold to reduce the likelihood that it will include fetal cells.

In step 102, when the sample to be tested or analyzed is a mixed sample (e.g. maternal blood sample), it is enriched for rare cells or rare DNA (e.g. fetal cells, fetal DNA or fetal nuclei) using one or more methods known in the art or disclosed herein. Such enrichment increases the ratio of fetal cells to non-fetal cells; the concentration of fetal DNA to non-fetal DNA; or the concentration of fetal cells in volume per total volume of the mixed sample.

In some embodiments, enrichment occurs by selective lysis as described above. For example, enucleated cells may be selectively lysed prior to subsequent enrichment steps or fetal nucleated cells may be selectively lysed prior to separation of the fetal nuclei from other cells and components in the sample.

In some embodiments, enrichment of fetal cells or fetal nuclei occurs using one or more size-based separation modules. Size-based separation modules include filtration modules, sieves, matrixes, etc., including those disclosed in International Publication Nos. WO 2004/113877, WO 2004/0144651, and US Application Publication No. 2004/011956.

In some embodiments, a size-based separation module includes one or more arrays of obstacles that form a network of gaps. The obstacles are configured to direct particles (e.g.

cells or nuclei) as they flow through the array/network of gaps into different directions or outlets based on the particle's hydrodynamic size. For example, as a blood sample flows through an array of obstacles, nucleated cells or cells having a hydrodynamic size larger than a critical size, e.g., 8 microns, are directed to a first outlet located on the opposite side of the array of obstacles from the fluid flow inlet, while the enucleated cells or cells having a hydrodynamic size smaller than a critical size, e.g., 8 microns, are directed to a second outlet also located on the opposite side of the array of obstacles from the fluid flow inlet.

An array can be configured to separate cells smaller than a critical size from those larger than the critical size by adjusting the size of the gaps, obstacles, and offset in the period between each successive row of obstacles. For example, in some embodiments, obstacles and/or gaps between obstacles can be up to 10, 20, 50, 70, 100, 120, 150, 170, or 200 microns in length or about 2, 4, 6, 8 or 10 microns in length. In some embodiments, an array for size-based separation includes more than 100, 500, 1,000, 5,000, 10,000, 50,000 or 100,000 obstacles that are arranged into more than 10, 20, 50, 100, 200, 500, or 1000 rows. Preferably, obstacles in a first row of obstacles are offset from a previous (upstream) row of obstacles by up to 50% of the period of the previous row of obstacles. In some embodiments, obstacles in a first row of obstacles are offset from a previous row of obstacles by up to 45, 40, 35, 30, 25, 20, 15 or 10% the period of the previous row of obstacles. Furthermore, the distance between a first row of obstacles and a second row of obstacles can be up to 10, 20, 50, 70, 100, 120, 150, 170 or 200 microns. A particular offset can be continuous (repeating for multiple rows) or non-continuous. In some embodiments, a separation module includes multiple discrete arrays of obstacles fluidly coupled such that they are in series with one another. Each array of obstacles has a continuous offset. But each subsequent (downstream) array of obstacles has an offset that is different from the previous (upstream) offset. Preferably, each subsequent array of obstacles has a smaller offset that the previous array of obstacles. This allows for a refinement in the separation process as cells migrate through the array of obstacles. Thus, a plurality of arrays can be fluidly coupled in series or in parallel, (e.g., more than 2, 4, 6, 8, 10, 20, 30, 40, 50). Fluidly coupling separation modules (e.g., arrays) in parallel allows for high-throughput analysis of the sample, such that at least 1, 2, 5, 10, 20, 50, 100, 200, or 500 mL per hour flows through the enrichment modules or at least 1, 5, 10, or 50 million cells per hour are sorted or flow through the device.

FIGS. 2A-2D illustrate one example of a size-based separation module. Obstacles (which may be of any shape) are coupled to a flat substrate to form an array of gaps. A transparent cover or lid may be used to cover the array. The obstacles form a two-dimensional array with each successive row shifted horizontally with respect to the previous row of obstacles, where the array of obstacles directs components having a hydrodynamic size smaller than a critical size in a first direction and components having a hydrodynamic size larger that a critical size in a second direction. See FIGS. 2B-2D. The flow of sample into the array of obstacles can be aligned at a small angle (flow angle) with respect to a line-of-sight of the array (lateral flow angle). Optionally, the array is coupled to an infusion pump to perfuse the sample through the obstacles. The flow conditions of the size-based separation module described herein are such that cells are sorted by the array with minimal damage. This allows for downstream analysis of intact cells and intact nuclei to be more efficient and reliable.

In one embodiment, a size-based separation module comprises an array of obstacles configured to direct rare cells larger than a critical size to migrate along a line-of-sight within the array towards a first outlet or bypass channel leading to a first outlet, while directing cells and analytes smaller than a critical size through the array of obstacles in a different direction towards a second outlet.

A variety of enrichment protocols may be utilized although gentle handling of the cells is preferred to reduce any mechanical damage to the cells or their DNA. This gentle handling also preserves the small number of fetal cells in the sample. Integrity of the nucleic acid being evaluated is an important feature in some embodiments to permit the distinction between the genomic material from the fetal cells and other cells in the sample. In particular, the enrichment and separation of the fetal cells using the arrays of obstacles produces gentle treatment which minimizes cellular damage and maximizes nucleic acid integrity permitting exceptional levels of separation and the ability to subsequently utilize various formats to very accurately analyze the genome of the cells which are present in the sample in extremely low numbers.

In some embodiments, enrichment of fetal cells occurs using one or more capture modules that selectively inhibit the mobility of one or more cells of interest. Preferably a capture module is fluidly coupled downstream to a size-based separation module. Capture modules can include a substrate having multiple obstacles that restrict the movement of cells or analytes greater than a critical size. Examples of capture modules that inhibit the migration of cells based on size are disclosed in U.S. Pat. Nos. 5,837,115 and 6,692,952.

In some embodiments, a capture module includes a two dimensional array of obstacles that selectively filters or captures cells or analytes having a hydrodynamic size greater than a particular gap size, e.g., critical sized. Arrays of obstacles adapted for separation by capture can include obstacles having one or more shapes and can be arranged in a uniform or non-uniform order. In some embodiments, a two-dimensional array of obstacles is staggered such that each subsequent row of obstacles is offset from the previous row of obstacles to increase the number of interactions between the analytes being sorted (separated) and the obstacles.

Another example of a capture module is an affinity-based separation module. An affinity-based separation module capture analytes or cells of interest based on their affinity to a structure or particle as oppose to their size. One example of an affinity-based separation module is an array of obstacles that are adapted for complete sample flow through, but for the fact that the obstacles are covered with binding moieties that selectively bind one or more analytes (e.g., cell population) of interest (e.g., red blood cells, fetal cells, or nucleated cells) or analytes not-of-interest (e.g., white blood cells). Binding moieties can include e.g., proteins (e.g., ligands/receptors), nucleic acids having complementary counterparts in retained analytes, antibodies, etc. In some embodiments, an affinity-based separation module comprises a two-dimensional array of obstacles covered with one or more antibodies selected from the group consisting of: anti-CD71, anti-CD235a, anti-CD36, anti-carbohydrates, anti-selectin, anti-CD45, anti-GPA, and anti-antigen-i.

Figure 3A:
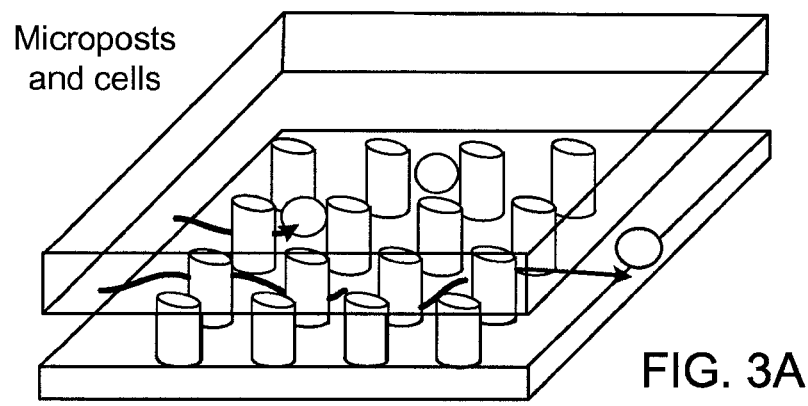
FIGS. 3A-3C illustrate one embodiment of an affinity separation module.
Figure 3B:
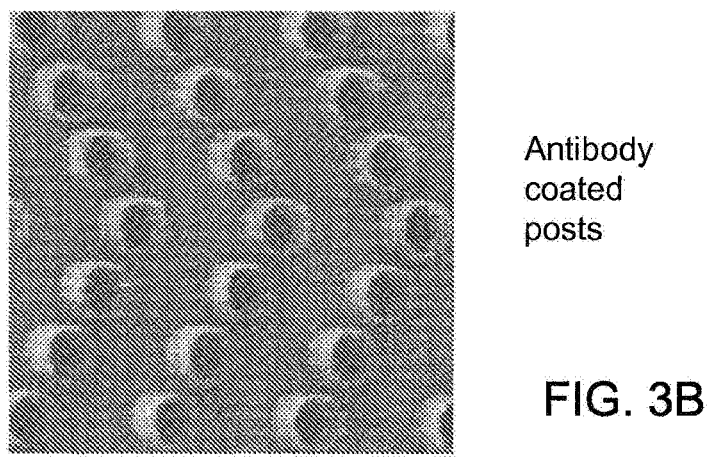
Figure 3C:
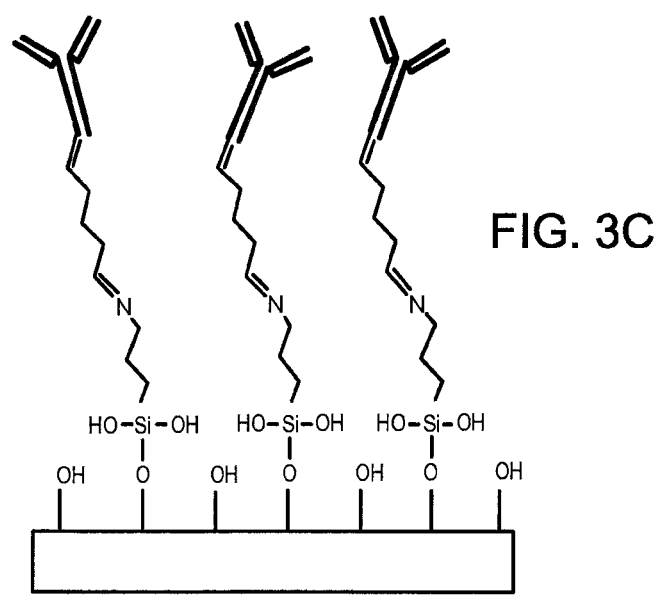

FIG. 3A illustrates a path of a first analyte through an array of posts wherein an analyte that does not specifically bind to a post continues to migrate through the array, while an analyte that does bind a post is captured by the array. FIG. 3B is a picture of antibody coated posts. FIG. 3C illustrates one method of coupling of antibodies to a substrate (e.g., obstacles, side walls, etc.) as contemplated by the present invention. Examples of such affinity-based separation modules are described in International Publication No. WO 2004/029221 and U.S. application Ser. No. 10/529,453, both of which are incorporated by reference.

In some embodiments, a capture module utilizes a magnetic field to separate and/or enrich one or more analytes (cells) that has a magnetic property or magnetic potential. For example, red blood cells which are slightly diamagnetic (repelled by magnetic field) in physiological conditions can be made paramagnetic (attributed by magnetic field) by deoxygenation of the hemoglobin into methemoglobin. This magnetic property can be achieved through physical or chemical treatment of the red blood cells. Thus, a sample containing one or more red blood cells and one or more non-red blood cells can be enriched for the red blood cells by first inducing a magnetic property and then separating the above red blood cells from other analytes using a magnetic field (uniform or non-uniform). For example, a maternal blood sample can flow first through a size-based separation module to remove enucleated cells and cellular components (e.g., analytes having a hydrodynamic size less than 6 μms) based on size. Subsequently, the enriched nucleated cells (e.g., analytes having a hydrodynamic size greater than 6 μms) white blood cells and nucleated red blood cells are treated with a reagent, such as $CO_2$, $N_2$ or $NaNO_2$, that changes the magnetic property of the red blood cells' hemoglobin. The treated sample then flows through a magnetic field (e.g., a column coupled to an external magnet), such that the paramagnetic analytes (e.g., red blood cells) will be captured by the magnetic field while the white blood cells and any other non-red blood cells will flow through the device to result in a sample enriched in nucleated red blood cells (including fnRBC's). Additional examples of magnetic separation modules are described in U.S. application Ser. No. 11/323,971, filed Dec. 29, 2005 entitled "Devices and Methods for Magnetic Enrichment of Cells and Other Particles" and U.S. application Ser. No. 11/227,904, filed Sep. 15, 2005, entitled "Devices and Methods for Enrichment and Alteration of Cells and Other Particles".

Subsequent enrichment steps can be used to separate the rare cells (e.g. fnRBC's) from the non-rare maternal nucleated red blood cells (non-RBC's). In some embodiments, a sample enriched by size-based separation followed by affinity/magnetic separation is further enriched for rare cells using fluorescence activated cell sorting (FACS) or selective lysis of a subset of the cells (e.g. fetal cells). In some embodiments, fetal cells are selectively bound to an anti-antigen i binding moiety (e.g. an antibody) to separate them from the mnRBC's. In some embodiments, the antibody binds to a fetal cell ligand. In some related embodiments the fetal cells are stimulated so as to induce expression of ligands which are targeted by an antibody. In some embodiments the fetal cells are lysed and the nuclei of the fetal cells are separated from other cellular components by binding them with an antibody. In some embodiments, fetal cells are selectively bound to receptors which target fetal cell ligands. In some embodiments, fetal cells are selectively bound to a lectin. In some embodiments, fetal cells or fetal DNA is distinguished from non-fetal cells or non-fetal DNA by forcing the rare cells (fetal cells) to become apoptotic, thus condensing their nuclei and optionally ejecting their nuclei. Rare cells such as fetal cells can be forced into apoptosis using various means including subjecting the cells to hyperbaric pressure (e.g. 4% $CO_2$). The condensed nuclei can be detected and/or isolated for further analysis using any technique known in the art including DNA gel electrophoresis, in situ labeling of DNA nicks (terminal deoxynucleotidyl transferase (TdT))-mediated dUTP in situ nick labeling (also known as TUNEL) (Gavrieli, Y., et al. J. Cell Biol 119:493-501 (1992)) and ligation of DNA strand breaks having one or two-base 3' overhangs (Taq polymerase-based in situ ligation). (Didenko V., et al. J. Cell Biol. 135:1369-76 (1996)).

In some embodiments, when the analyte desired to be separated (e.g., red blood cells or white blood cells) is not ferromagnetic or does not have a magnetic property, a magnetic particle (e.g., a bead) or compound (e.g., $Fe^{3+}$) can be coupled to the analyte to give it a magnetic property. In some embodiments, a bead coupled to an antibody that selectively binds to an analyte of interest can be decorated with an antibody elected from the group of anti CD71 or CD75. In some embodiments a magnetic compound, such as $Fe^{3+}$, can be couple to an antibody such as those described above. The magnetic particles or magnetic antibodies herein may be coupled to any one or more of the devices herein prior to contact with a sample or may be mixed with the sample prior to delivery of the sample to the device(s).

Magnetic field used to separate analytes/cells in any of the embodiments herein can uniform or non-uniform as well as external or internal to the device(s) herein. An external magnetic field is one whose source is outside a device herein (e.g., container, channel, obstacles). An internal magnetic field is one whose source is within a device contemplated herein. An example of an internal magnetic field is one where magnetic particles may be attached to obstacles present in the device (or manipulated to create obstacles) to increase surface area for analytes to interact with to increase the likelihood of binding. Analytes captured by a magnetic field can be released by demagnetizing the magnetic regions retaining the magnetic particles. For selective release of analytes from regions, the demagnetization can be limited to selected obstacles or regions. For example, the magnetic field can be designed to be electromagnetic, enabling turn-on and turn-off off the magnetic fields for each individual region or obstacle at will.

Figure 4:
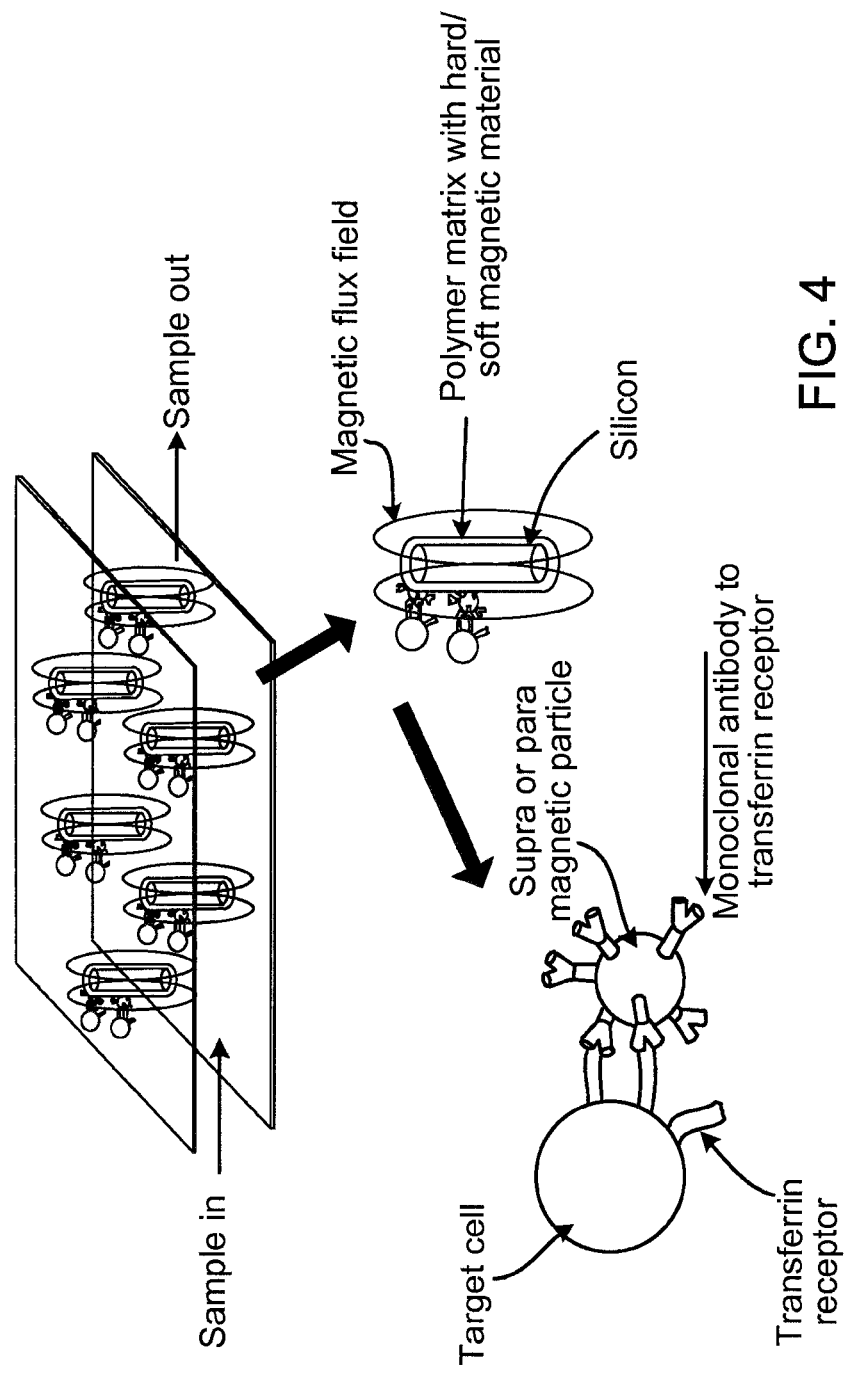
FIG. 4 illustrates one embodiment of a magnetic separation module.

FIG. 4 illustrates an embodiment of a device configured for capture and isolation of cells expressing the transferrin receptor from a complex mixture. Monoclonal antibodies to CD71 receptor are readily available off-the-shelf and can be covalently coupled to magnetic materials comprising any conventional ferroparticles, such as, but not limited to ferrous doped polystyrene and ferroparticles or ferro-colloids (e.g., from Miltenyi or Dynal). The anti CD71 bound to magnetic particles is flowed into the device. The antibody coated particles are drawn to the obstacles (e.g., posts), floor, and walls and are retained by the strength of the magnetic field interaction between the particles and the magnetic field. The particles between the obstacles and those loosely retained with the sphere of influence of the local magnetic fields away from the obstacles are removed by a rinse.

One or more of the enrichment modules herein (e.g., size-based separation module(s) and capture module(s)) may be fluidly coupled in series or in parallel with one another. For example a first outlet from a separation module can be fluidly coupled to a capture module. In some embodiments, the separation module and capture module are integrated such that a plurality of obstacles acts both to deflect certain analytes according to size and direct them in a path different than the direction of analyte(s) of interest, and also as a capture module to capture, retain, or bind certain analytes based on size, affinity, magnetism or other physical property.

In any of the embodiments herein, the enrichment steps performed have a specificity and/or sensitivity ≥50, 60, 70, 80, 90, 95, 96, 97, 98, 99, 99.1, 99.2, 99.3, 99.4, 99.5, 99.6, 99.7, 99.8, 99.9 or 99.95% The retention rate of the enrichment module(s) herein is such that ≥50, 60, 70, 80, 90, 91, 92, 93, 94, 95, 96, 97, 98, 99, or 99.9% of the analytes or cells of interest (e.g., nucleated cells or nucleated red blood cells or nucleated from red blood cells) are retained. Simultaneously, the enrichment modules are configured to remove ≥50, 60, 70, 80, 85, 90, 91, 92, 93, 94, 95, 96, 97, 98, 99, or 99.9% of all unwanted analytes (e.g., red blood-platelet enriched cells) from a sample.

Any or all of the enrichment steps can occur with minimal dilution of the sample. For example, in some embodiments the analytes of interest are retained in an enriched solution that is less than 50, 40, 30, 20, 10, 9.0, 8.0, 7.0, 6.0, 5.0, 4.5, 4.0, 3.5, 3.0, 2.5, 2.0, 1.5, 1.0, or 0.5 fold diluted from the original sample. In some embodiments, any or all of the enrichment steps increase the concentration of the analyte of interest (fetal cell), for example, by transferring them from the fluid sample to an enriched fluid sample (sometimes in a new fluid medium, such as a buffer). The new concentration of the analyte of interest may be at least 2, 4, 6, 8, 10, 20, 50, 100, 200, 500, 1,000, 2,000, 5,000, 10,000, 20,000, 50,000, 100,000, 200,000, 500,000, 1,000,000, 2,000,000, 5,000,000, 10,000,000, 20,000,000, 50,000,000, 100,000,000, 200,000,000, 500,000,000, 1,000,000,000, 2,000,000,000, or 5,000,000,000 fold more concentrated than in the original sample. For example, a 10 times concentration increase of a first cell type out of a blood sample means that the ratio of first cell type/all cells in a sample is 10 times greater after the sample was applied to the apparatus herein. Such concentration can take a fluid sample (e.g., a blood sample) of greater than 10, 15, 20, 50, or 100 mL total volume comprising rare components of interest, and it can concentrate such rare component of interest into a concentrated solution of less than 0.5, 1, 2, 3, 5, or 10 mL total volume.

The final concentration of fetal cells in relation to non-fetal cells after enrichment can be about $1/10,0001^{-1}1/10$, or $1/1,000–1/1,000$. In some embodiments, the concentration of fetal cells to maternal cells may be up to 1/1,000, 1/100, or 1/10 or as low as 1/100, 1/1,000 or 1/10,000.

Thus, detection and analysis of the fetal cells can occur even if the non-fetal (e.g. maternal) cells are >50%, 60%, 70%, 80%, 90%, 95%, or 99% of all cells in a sample. In some embodiments, fetal cells are at a concentration of less than 1:2, 1:4, 1:10, 1:50, 1:100, 1:1000, 1:10,000, 1:100,000, 1,000,000, 1:10,000,000 or 1:100,000,000 of all cells in a mixed sample to be analyzed or at a concentration of less than $1\times10^{-3}$, $1\times10^{-4}$, $1\times10^{-5}$, $1\times10^{-6}$, or $1\times10^{-6}$ cells/µL of the mixed sample. Over all, the number of fetal cells in a mixed sample, (e.g. enriched sample) has up to 1, 2, 3, 4, 5, 6, 7, 8, 9, 10, 15, 20, 30, 40, 50, 100 total fetal cells.

Figure 24:
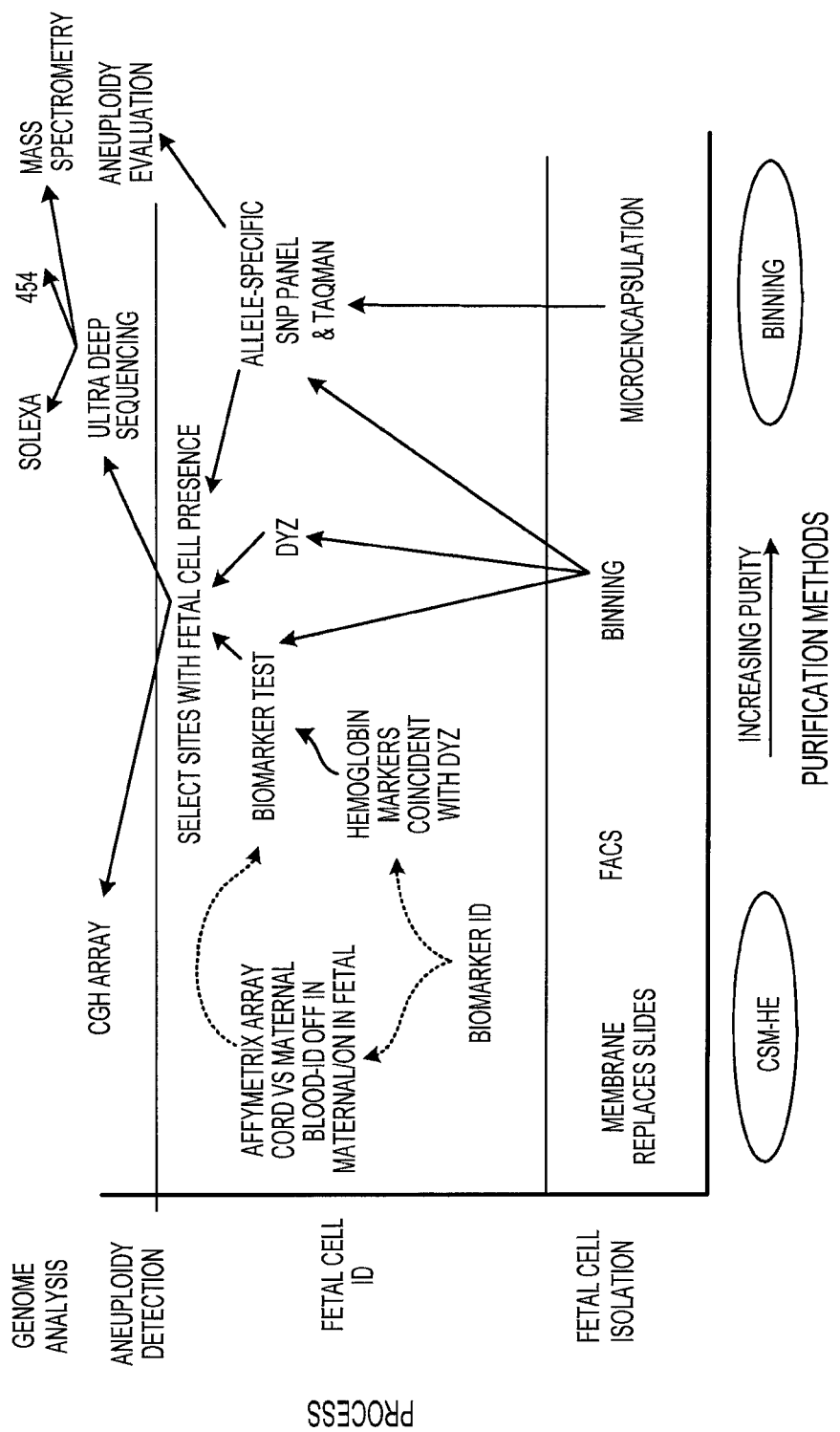
FIG. 24 illustrates methods of fetal diagnostic assays. Fetal cells are isolated by CSM-HE enrichment of target cells from blood. The designation of the fetal cells may be confirmed using techniques comprising FISH staining (using slides or membranes and optionally an automated detector), FACS, and/or binning. Binning may comprise distribution of enriched cells across wells in a plate (such as a 96 or 384 well plate), microencapsulation of cells in droplets that are separated in an emulsion, or by introduction of cells into microarrays of nanofluidic bins. Fetal cells are then identified using methods that may comprise the use of biomarkers (such as fetal (gamma) hemoglobin), allele-specific SNP panels that could detect fetal genome DNA, detection of differentially expressed maternal and fetal transcripts (such as Affymetrix chips), or primers and probes directed to fetal specific loci (such as the multi-repeat DYZ locus on the Y-chromosome). Binning sites that contain fetal cells are then be analyzed for aneuploidy and/or other genetic defects using a technique such as CGH array detection, ultra deep sequencing (such as Solexa, 454 or mass spectrometry), STR analysis, or SNP detection.
Figure 25:
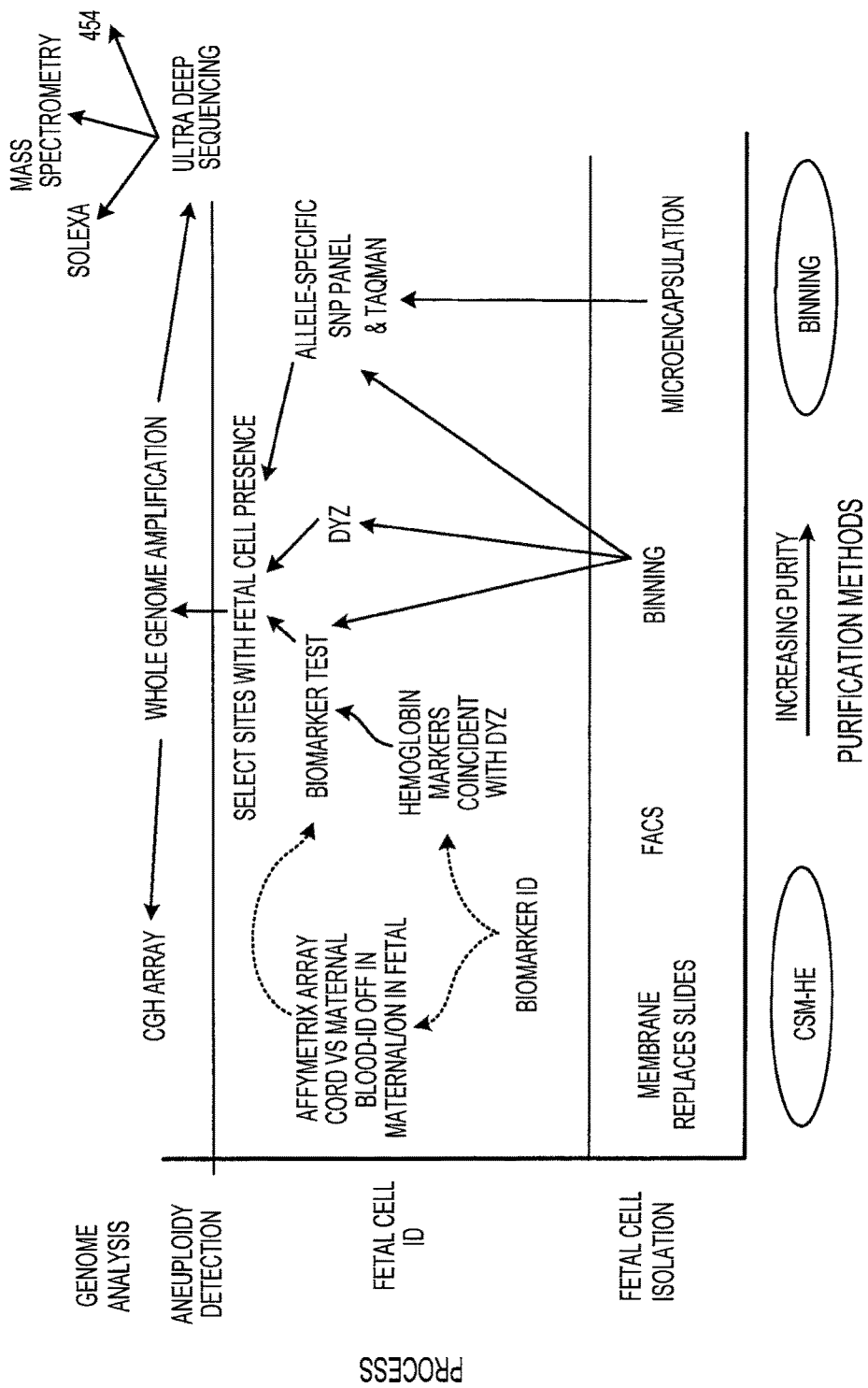
FIG. 25 illustrates methods of fetal diagnostic assays, further comprising the step of whole genome amplification prior to analysis of aneuploidy and/or other genetic defects.

Enriched target cells (e.g., fnRBC) may be "binned" prior to further analysis of the enriched cells (FIGS. 24 and 25). Binning is any process which results in the reduction of complexity and/or total cell number of the enriched cell output. Binning may be performed by any method known in the art or described herein. One method of binning is by serial dilution. Such dilution may be carried out using any appropriate platform (e.g., PCR wells, microtiter plates) and appropriate buffers. Other methods include nanofluidic systems which can separate samples into droplets (e.g., BioTrove, Raindance, Fluidigm). Such nanofluidic systems may result in the presence of a single cell present in a nanodroplet.

Binning may be preceded by positive selection for target cells including, but not limited to, affinity binding (e.g. using anti-CD71 antibodies). Alternately, negative selection of non-target cells may precede binning. For example, output from a size-based separation module may be passed through a magnetic hemoglobin enrichment module (MHEM) which selectively removes WBCs from the enriched sample by attracting magnetized hemoglobin-containing cells.

For example, the possible cellular content of output from enriched maternal blood which has been passed through a size-based separation module (with or without further enrichment by passing the enriched sample through a MHEM) may consist of: 1) approximately 20 fnRBC; 2) 1,500 mnRBC; 3) 4,000-40,000 WBC; 4) $15\times10^6$ RBC. If this sample is separated into 100 bins (PCR wells or other acceptable binning platform), each bin would be expected to contain: 1) 80 negative bins and 20 bins positive for one fnRBC; 2) 150 mnRBC; 3) 400-4,000 WBC; 4) $15\times10^4$ RBC. If separated into 10,000 bins, each bin would be expected to contain: 1) 9,980 negative bins and 20 bins positive for one fnRBC; 2) 8,500 negative bins and 1,500 bins positive for one mnRBC; 3) <1-4 WBC; 4) $15\times10^2$ RBC. One of skill in the art will recognize that the number of bins may be increased or decreased depending on experimental design and/or the platform used for binning. Reduced complexity of the binned cell populations may facilitate further genetic and/or cellular analysis of the target cells by reducing the number of non-target cells in an individual bin.

Analysis may be performed on individual bins to confirm the presence of target cells (e.g. fnRBC) in the individual bin. Such analysis may consist of any method known in the art including, but not limited to, FISH, PCR, STR detection, SNP analysis, biomarker detection, and sequence analysis (FIGS. 24 and 25).

Fetal Biomarkers

In some embodiments fetal biomarkers may be used to detect and/or isolate fetal cells, after enrichment or after detection of fetal abnormality or lack thereof. For example, this may be performed by distinguishing between fetal and maternal nRBCs based on relative expression of a gene (e.g., DYS1, DYZ, CD-71, ε- and ζ-globin) that is differentially expressed during fetal development. In preferred embodiments, biomarker genes are differentially expressed in the first and/or second trimester. "Differentially expressed," as applied to nucleotide sequences or polypeptide sequences in a cell or cell nuclei, refers to differences in over/under-expression of that sequence when compared to the level of expression of the same sequence in another sample, a control or a reference sample. In some embodiments, expression differences can be temporal and/or cell-specific. For example, for cell-specific expression of biomarkers, differential expression of one or more biomarkers in the cell(s) of interest can be higher or lower relative to background cell populations. Detection of such difference in expression of the biomarker may indicate the presence of a rare cell (e.g., fnRBC) versus other cells in a mixed sample (e.g., background cell populations). In other embodiments, a ratio of two or more such biomarkers that are differentially expressed can be measured and used to detect rare cells.

In one embodiment, fetal biomarkers comprise differentially expressed hemoglobins. Erythroblasts (nRBCs) are very abundant in the early fetal circulation, virtually absent in normal adult blood and by having a short finite lifespan, there is no risk of obtaining fnRBC which may persist from a previous pregnancy. Furthermore, unlike trophoblast cells, fetal erythroblasts are not prone to mosaic characteristics.

Yolk sac erythroblasts synthesize ε-, ζ-, γ- and α-globins, these combine to form the embryonic hemoglobins. Between six and eight weeks, the primary site of erythropoiesis shifts from the yolk sac to the liver, the three embryonic hemoglobins are replaced by fetal hemoglobin (HbF) as the predominant oxygen transport system, and ε- and ζ-globin production gives way to γ-, α-, and β-globin production within definitive erythrocytes (Peschle et al., 1985). HbF remains the principal hemoglobin until birth, when the second globin switch occurs and β-globin production accelerates.

Hemoglobin (Hb) is a heterodimer composed of two identical α globin chains and two copies of a second globin. Due to differential gene expression during fetal development, the composition of the second chain changes from ε globin during early embryonic development (1 to 4 weeks of gestation) to γ globin during fetal development (6 to 8 weeks of gestation) to β globin in neonates and adults as illustrated in (Table 1).

TABLE 1

Relative expression of ε, γ and β in maternal and fetal RBCs.

|  |  | ε | γ | B |
|---|---|---|---|---|
| 1$^{st}$ trimester | Fetal | ++ | ++ | − |
|  | Maternal | − | +/− | ++ |
| 2$^{nd}$ trimester | Fetal | − | ++ | +/− |
|  | Maternal | − | +/− | ++ |

In the late-first trimester, the earliest time that fetal cells may be sampled by CVS, fnRBCs contain, in addition to α globin, primarily ε and γ globin. In the early to mid second trimester, when amniocentesis is typically performed, fnRBCs contain primarily γ globin with some adult β globin. Maternal cells contain almost exclusively α and β globin, with traces of γ detectable in some samples. Therefore, by measuring the relative expression of the ε, γ and β genes in RBCs purified from maternal blood samples, the presence of fetal cells in the sample can be determined. Furthermore, positive controls can be utilized to assess failure of the FISH analysis itself.

In various embodiments, fetal cells are distinguished from maternal cells based on the differential expression of hemoglobins β2, γ or ε. Expression levels or RNA levels can be determined in the cytoplasm or in the nucleus of cells. Thus in some embodiments, the methods herein involve determining levels of messenger RNA (mRNA), ribosomal RNA (rRNA), or nuclear RNA (nRNA).

In some embodiments, identification of fnRBCs can be achieved by measuring the levels of at least two hemoglobins in the cytoplasm or nucleus of a cell. In various embodiments, identification and assay is from 1, 2, 3, 4, 5, 6, 7, 8, 9, 10, 15 or 20 fetal nuclei. Furthermore, total nuclei arrayed on one or more slides can number from about 100, 200, 300, 400, 500, 700, 800, 5000, 10,000, 100,000, 1,000,000, 2,000,000 to about 3,000,000. In some embodiments, a ratio for γ/β or ε/β is used to determine the presence of fetal cells, where a number less than one indicates that a fnRBC(s) is not present. In some embodiments, the relative expression of γ/β or ε/β provides a fnRBC index ("FNI"), as measured by γ or ε relative to β. In some embodiments, a FNI for γ/β greater than 5, 10, 15, 20, 25, 30, 35, 40, 45, 90, 180, 360, 720, 975, 1020, 1024, 1250 to about 1250, indicate that a fnRBC(s) is present. In yet other embodiments, a FNI for γ/β of less than about 1 indicates that a fnRBC(s) is not present. Preferably, the above FNI is determined from a sample obtained during a first trimester. However, similar ratios can be used during second trimester and third trimester.

In some embodiments, the expression levels are determined by measuring nuclear RNA transcripts including, nascent or unprocessed transcripts. In another embodiment, expression levels are determined by measuring mRNA, including ribosomal RNA. There are many methods known in the art for imaging (e.g., measuring) nucleic acids or RNA including, but not limited to, using expression arrays from Affymetrix, Inc. or Illumina, Inc.

RT-PCR primers can be designed by targeting the globin variable regions, selecting the amplicon size, and adjusting the primers annealing temperature to achieve equal PCR amplification efficiency. Thus TaqMan probes can be designed for each of the amplicons with well-separated fluorescent dyes, Alexa Fluor®-355 for ε, Alexa Fluor®-488 for γ, and Alexa Fluor-555 for β. The specificity of these primers can be first verified using ε, γ, and β cDNA as templates. The primer sets that give the best specificity can be selected for further assay development. As an alternative, the primers can be selected from two exons spanning an intron sequence to amplify only the mRNA to eliminate the genomic DNA contamination.

The primers selected can be tested first in a duplex format to verify their specificity, limit of detection, and amplification efficiency using target cDNA templates. The best combinations of primers can be further tested in a triplex format for its amplification efficiency, detection dynamic range, and limit of detection.

Various commercially available reagents are available for RT-PCR, such as One-step RT-PCR reagents, including Qiagen One-Step RT-PCR Kit and Applied Biosytems TaqMan One-Step RT-PCR Master Mix Reagents kit. Such reagents can be used to establish the expression ratio of ε, γ, and β using purified RNA from enriched samples. Forward primers can be labeled for each of the targets, using Alexa fluor-355 for ε, Alexa fluor-488 for γ, and Alexa fluor-555 for β. Enriched cells can be deposited by cytospinning onto glass slides. Additionally, cytospinning the enriched cells can be performed after in situ RT-PCR. Thereafter, the presence of the fluorescent-labeled amplicons can be visualized by fluorescence microscopy. The reverse transcription time and PCR cycles can be optimized to maximize the amplicon signal:background ratio to have maximal separation of fetal over maternal signature. Preferably, signal:background ratio is greater than 5, 10, 50 or 100 and the overall cell loss during the process is less than 50, 10 or 5%.

Fetal Cell Analysis

The detection and analysis steps may involve quantifying genomic DNA regions from cells in a sample or enriched sample. In some embodiments, the quantified genomic DNA regions are polymorphic sites such as short tandem repeats (STRs) or variable number of tandem repeats (VNTRs).

In step 103, polymorphic genomic DNA region(s) or whole genome(s) from the mixed sample and optionally reference sample are pre-amplified to increase the overall abundance of DNA used for quantification and analysis. Pre-amplification can be preformed using multiple displacement amplification (MDA) (Gonzalez et al. Envircon Microbiol; 7(7); 1024-8 (2005)) or amplification with outer primers in a nested PCR approach. This permits detection and analysis of fetal DNA even if the total amount of fetal DNA in the mixed (e.g. enriched) sample is only up to 1 μg, 500 ng, 200 ng, 100 ng, 50 ng, 40 ng, 30 ng, 20 ng, 10 ng, 5 ng, 1 ng, 500 pg, 200 pg, 100 pg, 50 pg, 40 pg, 30 pg, 20 p, 10 pg, 5 pg, or 1 pg or between 1-5 µg, 5-10 µg, or 10-50 µg. Pre-amplification allows the products to be split into multiple reactions at the next step.

In step 104, polymorphic DNA region(s) such as short tandem repeats (STRs) or variable number of tandem repeats (VNTRs) are selected on suspected trisomic chromosome(s) (e.g., 13, 18, 21, X or Y) or chromosome(s) associated with a condition to be detected and optionally on control (non-trisomic) chromosomes. In some embodiments, 1 or more than 1, 2, 3, 4, 5, 6, 7, 8, 9, 10, 15, 20 DNA polymorphic loci are selected per target chromosome. Multiple polymorphic regions can be analyzed independently or at the same time in the same reaction. The polymorphic DNA regions, e.g. STRs loci, are selected for high heterozygosity (variety of alleles) so that the paternal allele of the fetal cells is more likely to be distinct in length from the maternal alleles. This results in an improved power to detect the presence of fetal cells in the mixed sample and potential fetal abnormalities in such cells. When the polymorphic regions selected are STR loci, di-, tri-, tetra- or penta-nucleotide repeat loci can be used for detection and analysis of fetal cells. Examples of STR loci that may be selected include: D21S1414, D21S1411, D21S1412, D21S11 MBP, D13S634, D13S631, D18S535, AmgXY, XHPRT, as well as those listed in FIG. 12. In some embodiment, the methods of the invention allow for the determination of maternal or paternal trisomy.

In step 105, the polymorphic loci selected are amplified. This can be used to detect non-maternal fetal alleles in the mixed sample and to determine the copy number of such alleles. When amplifying more than one polymorphic loci or DNA regions, primers are selected to be multiplexable (fairly uniform melting temperature, absence of cross-priming on the human genome, and absence of primer-primer interaction based on sequence analysis) with other primer pairs. Primers and loci are chosen so that the amplicon lengths from a given locus do not overlap with those from another locus.

In some embodiments, multiple dyes and multi-color fluorescence readout may be used to increase the multiplexing capacity, e.g. of a single CGE. This ensures that the loci are kept distinct in the readout (e.g. CGE readout). In such a case, PCR primer pairs can be grouped and the same end-labeling is applied to the members of a group.

Examples of primers known in the art that correspond to specific STR loci that can be used in the present invention are described in FIG. 13 and FIG. 14.

Examples of PCR techniques that can be used to amplify the DNA regions herein include, but are not limited, to quantitative PCR, quantitative fluorescent PCR (QF-PCR), multiplex fluorescent PCR (MF-PCR), real time PCR (RT-PCR), single cell PCR, restriction fragment length polymorphism PCR (PCR-RFLP), PCR-RFLP/RT-PCR-RFLP, hot start PCR, nested PCR, in situ polonony PCR, in situ rolling circle amplification (RCA), bridge PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that may be used to amplify specific polymorphic loci include those described in, U.S. Pat. Nos. 5,242, 794, 5,494,810, 4,988,617 and 6,582,938.

In step 106, the amplified DNA polymorphic regions (e.g. STR loci) from both mixed and reference samples are characterized and quantified using any method known in the art. Examples of such methods include, but are not limited to, gas chromatography, supercritical fluid chromatography, liquid chromatography, including partition chromatography, adsorption chromatography, ion exchange chromatography, size-exclusion chromatography, thin-layer chromatography, and affinity chromatography, electrophoresis, including capillary electrophoresis, capillary zone electrophoresis, capillary isoelectric focusing, capillary electrochromatography, micellar electrokinetic capillary chromatography, isotachophoresis, transient isotachophoresis and capillary gel electrophoresis, comparative genomic hybridization (CGH), microarrays, bead arrays, high-throughput genotyping technology, such as molecular inversion probe (MIP), and Genescan.

In one embodiment, capillary gel electrophoresis (CGE) is used to quantify STRs in both the mixed and reference samples. This can be used to detect non-maternal fetal alleles in the mixed sample and to determine the copy number of such alleles. The mixed sample and the reference sample can be analyzed in separate reactions, e.g. separate CGE lanes. Alternatively, the mixed and the reference sample can be run in the same reaction, e.g. same CGE lane, by using two different dye labels, e.g. differently labeled PCR primers. When a reference sample is run through the PCR/CGE process, the alleles show up as peaks in the CGE. It is desirable, but not essential, to associate these peaks with known alleles in the population at each locus. When performing PCR/CGE it may be very useful to reduce the non-linearities in the response of PCR to input DNA copies (i.e. to effect more quantitative PCR) so that the data can be more easily related to models of aneuploidy. This 'linearization' can be accomplished by the following procedure:

(a) The PCR reaction is initiated.
(b) The PCR reaction is interrupted after N cycles (N=5 to 10) and ~one third of the reaction products are removed and run on CGE. PCR cycling is re-initiated. Repeat until 40 PCR cycles or saturation is achieved.
(c) CGE peak masses are determined and normalized to correct for the depletion of the reaction products at each iteration of (b).
(d) A saturation (splining) curve is fit to the normalized data for each allele peak, and quantitative starting concentrations are inferred as in customary qPCR.

The above procedure tends to accomplish quantitative PCR while enabling a high degree of multiplexing. Because each CGE run has a slightly different relation between DNA fragment size (and sequence) and mobility, each trace typically will need to undergo a length transformation, such as a low-order (cubic or quartic) polynomial transformation, in order to map to the data from the trace corresponding to the previous amplification point. This mapping can be determined by adjusting the transformation parameters to achieve the best fit of the one data trace to the other, with both normalized to the same total sum of squares or summed peak heights.

The maternal peaks at each locus provide an estimate of the secondary 'stutter' structure at each locus due to PCR errors. The locations of these small secondary peaks can be used to blank out length regions that are contaminated by this stutter when looking for and using the non-maternal allele peaks (as described herein for example). Alternatively, more sophisticated 'deconvolution' algorithms can be applied to remove the stutter Stoughton, et al., *Electrophoresis*, 18(1): 1-S (1997).

The sample containing an unknown mixture of fetal and maternal cells is analyzed as in Step (b). This could be done in a separate CGE lane, or in the same CGE lane as the maternal sample by using two different dye labels on the PCR primers. Because each CGE trace has a slightly different relation between DNA fragment size (and sequence) and mobility, these data typically will need to undergo a length transformation, such as a low-order (cubic or quartic) polynomial transformation in order to map one trace onto the other to facilitate peak identification and model fitting. This mapping can be determined by adjusting the transformation parameters to achieve the best fit of the peak locations in one data trace to the other. This mapping will be well determined in the assumed situation where the maternal cells are more numerous than the fetal cells, because the maternal signature will dominate and will be shared in the two data sets.

Figure 5:
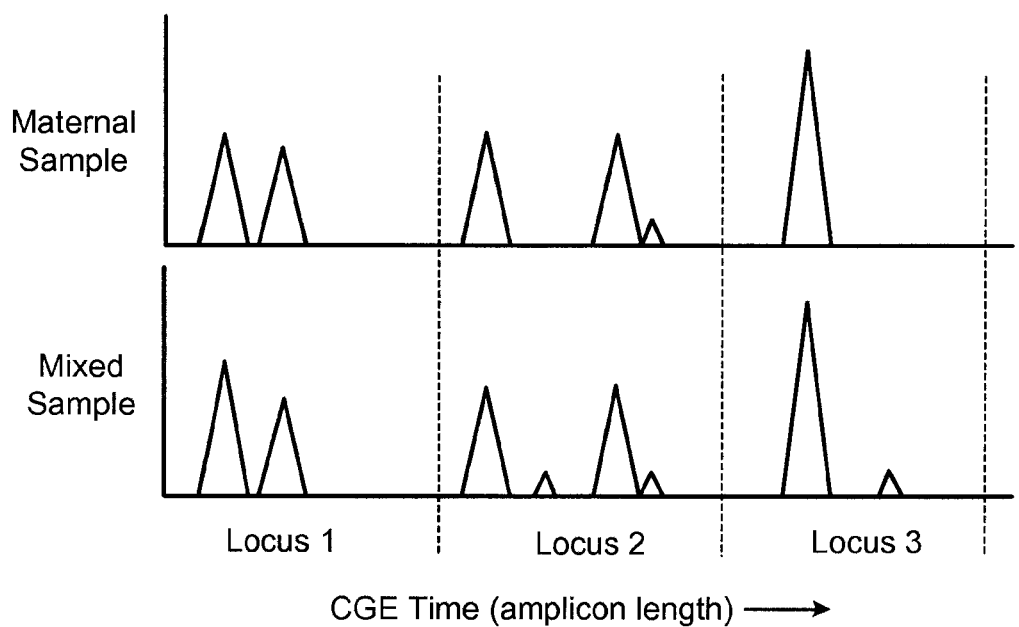
FIG. 5 illustrates typical locus patterns arising from a normal (diploid) fetus and mother.

FIG. 5 illustrates typical locus patterns arising from a normal (diploid) fetus and mother. At Locus 1, the paternal allele is the same as the left hand maternal allele, and adds to its apparent height. At Locus 2, the paternal allele has a length between the lengths of the maternal alleles. In addition, there is a secondary 'stutter' peak on the shoulder of the right hand maternal peak. In Locus 3, the maternal sample is homozygous leading to only one main peak, and the paternal allele is distinct from this allele.

Figure 6:
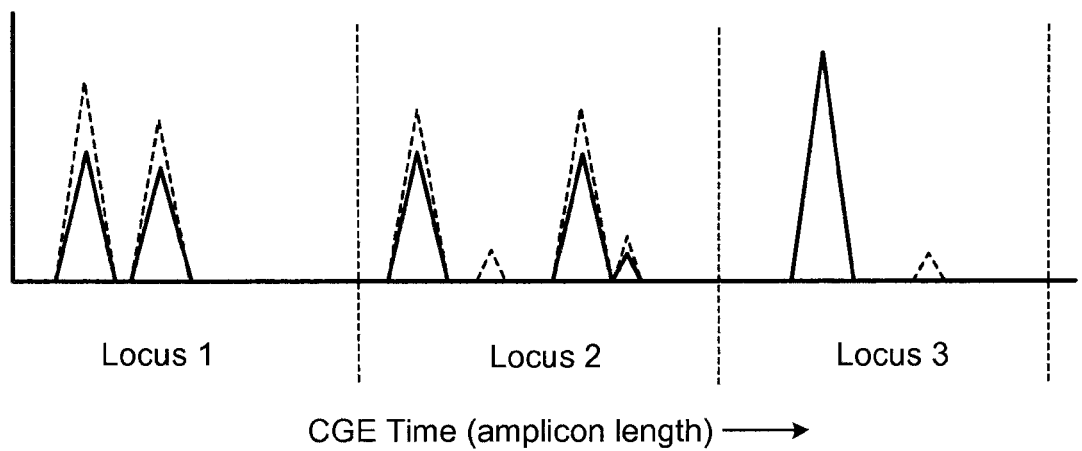
FIG. 6 illustrates typical locus patterns arising from trisomic fetal cells.
Figure 7A:
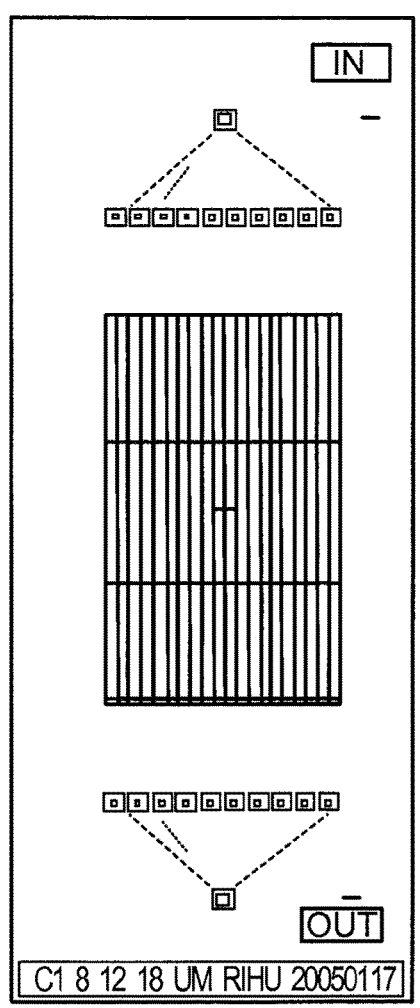
FIGS. 7A-7D illustrate various embodiments of a size-based separation module.
Figure 7B:
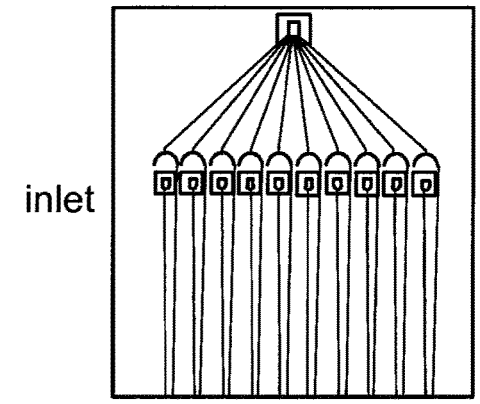
Figure 7C:
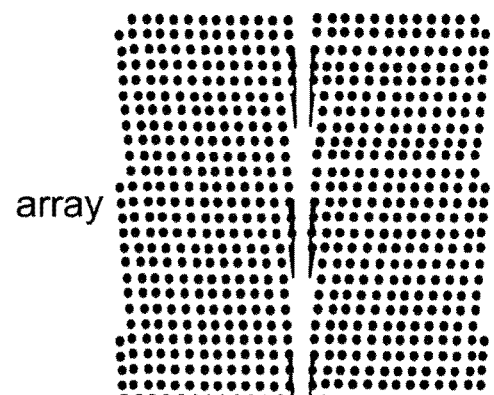
Figure 7D:
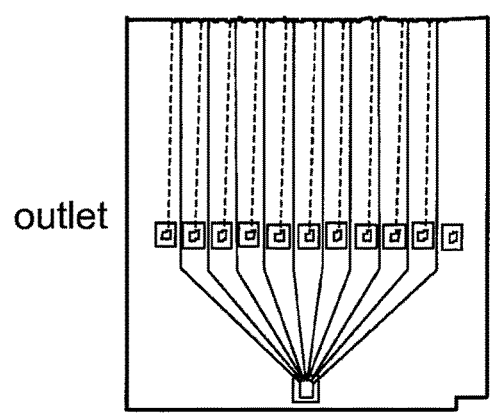

FIG. 6 illustrates locus patterns arising from trisomic fetal cells. The dashed trace represents mixed sample containing trisomic fetal cells, superposed on maternal sample trace (solid black). Trisomy causes excess amplitude in maternal alleles at loci contained within the aneuploid region (here assumed to contain Loci 1 and 2 but not Locus 3). The left hand maternal peak at Locus 1 contains contributions from the trisomy and from a paternal allele.

In step 107, data models are constructed. From the data obtained from the quantifying step different data models can be constructed depending upon different assumptions.

For example, a data model for the CGE patterns in FIGS. 5 and 6 can be as follows:

Let m1 denote the CGE signal obtained from one of the maternal alleles at a given locus and m2 the signal obtained from the other maternal allele, which might be the same allele. Let p denote the CGE signal obtained from the paternal allele at a given locus. Let p1 and p2 denote the CGE signals obtained from the paternal alleles at a given locus when a paternally derived trisomy occurs. Let □ α and β denote the relative number of maternal and fetal cells, respectively. Then in the case of a chromosome with maternal non-dysjunction trisomy, the data will have the form $$x = \alpha(\square m1 + m2) + \beta(m1 + m2 + p). \quad (1)$$

A normal (diploid) chromosome will give $$x = \alpha(m1 + m2) + \beta([m1 \text{ or } m2] + p), \quad (2)$$

and a paternally derived trisomy will give $$x = \alpha(m1 + m2) + \beta([m1 \text{ or } m2] + p1 + p2). \quad (3)$$

In some embodiments, data and data model is represented as discrete peak masses (or heights) and peak locations or as vectors of values representing the actual peak profiles. In the case of representation by peak characteristics, the 'addition' operation in Equations 1-3 denotes summation of peak height or mass at the discrete allele location. In the case where the full peak profiles are represented, summation denotes summation of signals bin by bin over the CGE trace, and in this case it may be helpful to zero the data except in the immediate vicinity of actual peaks. Representation via peak characteristics is preferable when using the PCR linearization technique described above.

To determine aneuploidy, the differences between the structure of the β-term that appears in the first and second equations above is determined. In the first case, there is an additional contribution to both maternal alleles along with the paternal allele, and in the second case there is an additional contribution only to one of the maternal alleles along with the paternal allele. The essence of the presence/absence declaration for fetal cells lies in the evidence for being greater than zero.

In step 108, the best overall fit of model to data is selected from among all the model sets. This modeling approach optimally uses information contained in the increase of chromosome copy number with aneuploidy and its association with the strength of non-maternal alleles.

In some embodiments, CGE signals representing m1 and m2 at each locus are obtained by profiling the maternal-only sample and mapping the peak locations to the corresponding ones of the mixed sample. The heights of m1 and m2 may be unequal, and this helps correct for PCR amplification biases associated with particular alleles. The values of p, p1, p2, α, and are determined from the mixed sample data by fitting Equations 1-3 to the data, optionally by using the least squares, or the maximum likelihood methods.

The three models need to be fit to each chromosome with suspected trisomy, e.g. chromosomes 13, 18, 21, X and/or Y. If there are only 3 suspected chromosomes, this results in 27 model variants (3×3×3=27). In Equations 2 and 3, there is also the ambiguity between using m1 or m2 in the β-term, so there are 5 model variants for each chromosome, with 5×5×5=125 total variants over three suspected trisomy chromosomes.

Segmental aneuploidies also could be tested by hypothesizing that different contiguous subsets of loci are contained within the aneuploid region. With each model variant, α and β have to be determined and the parameters describing the paternal alleles have to be determined at each locus for each model variant. The paternal allele peak height and shape can be assumed to be an average of the known maternal ones at that locus, while the paternal allele location needs to be fit to the data. The possible locations for the paternal allele will be the location of m1, the location of m2, and 'elsewhere in the locus window' where this latter possibility involves a search over discrete shifts smaller than a typical peak half-width at half maximum. Prior probabilities on the choices of p, taken from population allele frequency data, can be used, if their product lengths can be predicted.

In some cases, because of the number of parameters being fit, suboptimal searches can be used for computational efficiency. For example, one possible approach involves iterative methods, such as the following, which would be applied to each data model variant:

(i) Set β to 0 and solve for α.
(ii) Set β to a value where β/α is the smallest fetal maternal cell ratio for which fetal cells are likely to be detectable.
(iii) Solve for paternal allele location(s) at each locus, one locus at a time that minimize data-model residuals.
(iv) Fix the paternal allele parameters and adjust β to minimize residuals over all the data.
(v) Now vary only α to minimize residuals.
(vi) Repeat iv and v until convergence.
(vii) Repeat iii through v until convergence.

In step 109, the presence or absence of fetal DNA is determined using the models described above. The best overall fit for such models yields the values of $\beta$, $\alpha$ that can be called $\beta_{max}\square$, $\alpha_{max}$. The likelihood of observing the data given $\beta_{max}$ can be compared to the likelihood given $\beta=0$. The ratio is a measure of the amount of evidence for fetal DNA. A threshold for declaring fetal DNA is the likelihood ratio of approximately 1000 or more. The likelihood calculation can be approximated by a Chi-squared calculation involving the sum of squared residuals between the data and the model, where each residual is normalized by the expected rms error.

If it is determined that fetal DNA is not present in the mixed sample as calculated above, then the test is declared to be non-informative. On the other hand, if it is decided that fetal DNA is present in the mixed sample, then the likelihoods of the data given the different data model types can be compared to declare trisomy or another condition.

In step 110, the likelihood ratios of trisomy models (Equations 1 and 3) to the normal model (Equation 2) are calculated and these ratios are compared to a predefined threshold. This threshold can be set so that in controlled tests all the trisomic cases are declared aneuploid, and so that it is expected that the vast majority (>99.9%) of all truly trisomic cases are declared aneuploid by the test. In one embodiment, to accomplish a detection rate of >90% or 95% or approximately 99.9%, the likelihood ratio threshold is increased beyond what is necessary to declare all the known trisomic cases in the validation set by a factor of 1000/N, where N is the number of trisomy cases in the validation set.

In step 111, errors that may arise from the experimental procedure used to obtain the data can be taken into account in the model calculation(s). For instance, in the example described above, CGE data contain small additive errors associated with CGE readout, and larger multiplicative errors associated with PCR amplification efficiencies being different from locus to locus and from allele to allele within a locus. By using the maternal-only data to define m1 and m2 peak characteristics at each locus, the effects of PCR amplification biases associated with different primers and different amplicons from the same primers have been mostly controlled. Nevertheless, small variations in the process from day to day and the statistics of small numbers of starting genome copies will cause some random errors to remain. These tend to be multiplicative errors in the resulting CGE peak heights; e.g. two peaks may be 20% different in height although the starting concentrations of the alleles were identical. In one embodiment, it may be assumed that errors are random from peak to peak, and have relatively small additive errors, and larger Poisson and multiplicative error components. The magnitudes of these error components can be estimated from repeated PCR/CGE processing of identical samples. The Chi-square residuals calculation for any data-model fit then can be supported with these modeled squared errors for any peak height or data bin.

In another aspect of the present invention, the presence of fetal cells in a mixed sample and fetal abnormalities in said cells is determined without trying to integrate them in a data-model fitting procedure described above. For example, steps 100-107 can be performed as described above. Then, analysis using Equations 1 and 2 focuses on two indications. First, aneuploidy results in an excess of DNA for the trisomic chromosome, and this is indicated by the difference in mean strengths of the alleles on the trisomic chromosome compared to control chromosomes. A t-test can be applied to the two distributions of m1 and m2 peak heights. These peak heights are normalized to (e.g., divided peak-by-peak by) the corresponding peaks in the maternal-only sample to reduce PCR amplification biases. Second, Equations 1 and 2 show that aneuploidy is associated with less inequality in the heights of m1 and m2 at a given locus, particularly for loci where the paternal allele is distinct from the maternal alleles. Loci are selected where a third (paternal) allele is visibly distinct from two maternal alleles, and the distribution of the inequalities (measured in %) between the m1 and m2 peaks are compared between suspected trisomy chromosomes and control chromosomes. Again, peak heights first are normalized by the maternal-only sample. These two lines of evidence are combined to create an overall likelihood, such as by multiplying the probability values from the two lines of evidence. The presence/absence call is done in a simplified way by looking for loci where a third allele is clearly visible, and comparing the distribution of these peak heights between the maternal and mixed samples. Again, a t-test between these distributions gives the probability of fetal DNA being present.

In another aspect of the invention, the methods herein only determine presence or absence of fetal DNA, and aneuploidy information is known from another sources (e.g. fluorescence in situ hybridization (FISH) assay). For example, it may be desirable only to verify the presence or absence of fetal cells to ensure that a diploid test result is truly due to a normal fetus and not to failure of an assay (e.g. FISH). In this case, the process may be simplified by focusing on detecting the presence of non-maternal alleles without regard to associating them with increases in the maternal allele strengths at the same locus. Thus a process similar to the one outlined above may be used but it is not as necessary to arrange the PCR product lengths so that the products from different loci have distinct length windows in the CGE readout. The alleles from the different loci can be allowed to fall essentially anywhere in the effective measurement length window of the CGE. It also is not necessary to 'lineate' the PCR result(s) via multiple CGE readouts at different stages in the PCR cycling as is suggested in step 107.

Therefore, maternal-only and mixed samples are run and mapped to each other to align maternal allele peak locations, as described above. PCR is run to saturation, or nearly to saturation, to be sure to detect the low abundance fetal sequences. The evidence for fetal DNA then arises from extra peaks in the mixed-sample data with respect to the maternal-sample data. Based on typical heterozygosities of approximately 0.7 for highly polymorphic STRs, the chance of not seeing a distinct paternal allele (distinct from both maternal alleles) when fetal DNA is in fact present decreases approximately as $(0.7^2)^N$, where N is the number of loci included. Thus approximately ten STR loci will provide ~99.9% probability of detection. In addition, the present invention provides methods to determine when there are insufficient fetal cells for a determination and report a non-informative case. The present invention involves quantifying regions of genomic DNA from a mixed sample. More particularly the invention involves quantifying DNA polymorphisms from the mixed sample. In some embodiments, one or more than 1, 2, 3, 4, 5, 6, 7, 8, 9, 10, 15, 20 DNA polymorphism loci (particularly STRs) per target chromosome are analyzed to verify presence of fetal cells.

Any of the steps above can be performed by a computer program product that comprises a computer executable logic that is recorded on a computer readable medium. For example, the computer program can execute some or all of the following functions: (i) controlling enrichment of fetal cells or DNA from mixed sample and reference sample, (ii) pre-amplifying DNA from both samples, (iii) amplifying specific polymorphic DNA regions from both samples, (iv) identifying and quantifying maternal alleles in the reference sample, (v) identifying maternal and non-maternal alleles in the mixed sample, (vi) fitting data on alleles detected from mixed and/or reference samples into data models, (vii) determining the presence or absence of fetal cells in the mixed sample, (viii) declaring normal or abnormal phenotype for a fetus based on data models or declaring non-informative results, and (ix) declaring a specific fetal abnormality based on the above results. In particular, the computer executable logic can fit data on the quantity of DNA polymorphism(s) (e.g. STR's) into one or more data models. One example of a data model provides a determination of a fetal abnormality from given data signals obtained by molecular analysis e.g. CGE. The computer executable logic provides for a determination of the presence or absence of a trisomy, and distinguish whether the trisomy is paternally derived or if it originates from a maternal non-disjunction event. For example, given the following data signals that can be obtained by molecular analysis (e.g. CGE)

m1, which represents a signal obtained from one of the maternal alleles (m1) at a given locus, m2, which represents a signal obtained from the other maternal allele, which might be the same allele, p, which is a signal that is obtained from the paternal allele at a given locus, and p1 and p2, which are signals obtained from the paternal alleles at one given locus when a paternally derived trisomy occurs, and letting α and β, which denote the relative number of maternal and fetal cells, respectively, the following determinations can be made. In the case of a chromosome with maternal non-disjunction trisomy, the data will have the form $$x = \alpha(\square m1 + m2) + \beta(m1 + m2 + p). \quad (1)$$

A normal (diploid) chromosome will give $$x = \alpha(m1 + m2) + \beta([m1 \text{ or } m2] + p), \quad (2)$$

and a paternally derived trisomy will give $$x = \alpha(m1 + m2) + \beta([m1 \text{ or } m2] + p1 + p2). \quad (3)$$

The computer executable logic can work in any computer that may be any of a variety of types of general-purpose computers such as a personal computer, network server, workstation, or other computer platform now or later developed. In some embodiments, a computer program product is described comprising a computer usable medium having the computer executable logic (computer software program, including program code) stored therein. The computer executable logic can be executed by a processor, causing the processor to perform functions described herein. In other embodiments, some functions are implemented primarily in hardware using, for example, a hardware state machine. Implementation of the hardware state machine so as to perform the functions described herein will be apparent to those skilled in the relevant arts.

The program can provide a method of evaluating the presence or absence of trisomy in a mixed cell sample by accessing data that reflects the level of polymorphism(s) at two alleles at two or more given loci in a mixed sample (maternal and fetal cells) and in a sample enriched in fetal cells, relating the levels of polymorphism(s) to the number of maternal and fetal cells (a and in equations 1-3), and determining the presence or absence of trisomy in the samples.

In one embodiment, the computer executing the computer logic of the invention may also include a digital input device such as a scanner. The digital input device can provide information on the polymorphism levels/quantity. For example, a scanner of this invention can provide an image of the DNA polymorphism (particularly STRs) according to method herein. For instance, a scanner can provide an image by detecting fluorescent, radioactive, or other emission; by detecting transmitted, reflected, or scattered radiation; by detecting electromagnetic properties or other characteristics; or by other techniques. The data detected is typically stored in a memory device in the form of a data file. In one embodiment, a scanner may identify one or more labeled targets. For instance, a first DNA polymorphism may be labeled with a first dye that fluoresces at a particular characteristic frequency, or narrow band of frequencies, in response to an excitation source of a particular frequency. A second DNA polymorphism may be labeled with a second dye that fluoresces at a different characteristic frequency. The excitation sources for the second dye may, but need not, have a different excitation frequency than the source that excites the first dye, e.g., the excitation sources could be the same, or different, lasers.

Another aspect of the invention includes kits containing the devices and reagents for performing the enrichment and genetic analysis. Such kits may include the materials for any individual step disclosed, any combination of devices and reagents or the devices and reagents for performing all of the steps. For example, a kit may include the arrays for size-based enrichment, the device for magnetic separation of the cells and reagents for performing PCR or CGE. Also included may be the reagents for performing multiple displacement amplification. This is an exemplary kit and the kits can be constructed using any combination of disclosed materials and devices. The use of the size-based enrichment provides gentle handling that is particularly advantageous for permitting subsequent genetic analysis.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1

Separation of Fetal Cord Blood

FIGS. 7A-7D illustrates a schematic of the device used to separate nucleated cells from fetal cord blood.

Dimensions: 100 mm×28 mm×1 mm

Array design: 3 stages, gap size=18, 12 and 8 µm for the first, second and third stage, respectively.

Device fabrication: The arrays and channels were fabricated in silicon using standard photolithography and deep silicon reactive etching techniques. The etch depth is 140 µm. Through holes for fluid access are made using KOH wet etching. The silicon substrate was sealed on the etched face to form enclosed fluidic channels using a blood compatible pressure sensitive adhesive (9795, 3M, St Paul, Minn.).

Device packaging: The device was mechanically mated to a plastic manifold with external fluidic reservoirs to deliver blood and buffer to the device and extract the generated fractions.

Device operation: An external pressure source was used to apply a pressure of 2.0 PSI to the buffer and blood reservoirs to modulate fluidic delivery and extraction from the packaged device.

Experimental conditions: Human fetal cord blood was drawn into phosphate buffered saline containing Acid Citrate Dextrose anticoagulants. 1 mL of blood was processed at 3 mL/hr using the device described above at room temperature and within 48 hrs of draw. Nucleated cells from the blood were separated from enucleated cells (red blood cells and platelets), and plasma delivered into a buffer stream of calcium and magnesium-free Dulbecco's Phosphate Buffered Saline (14190-144, Invitrogen, Carlsbad, Calif.) containing 1% Bovine Serum Albumin (BSA) (A8412-100 ML, Sigma-Aldrich, St Louis, Mo.) and 2 mM EDTA (15575-020, Invitrogen, Carlsbad, Calif.).

Figure 8A:
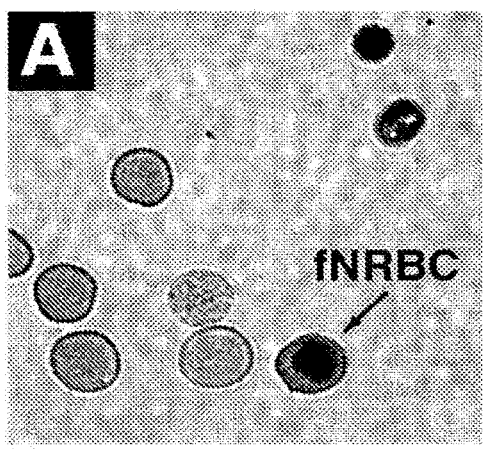
FIGS. 8A-8B illustrate cell smears of the product and waste fractions.

Measurement techniques: Cell smears of the product and waste fractions (FIG. 8A-8B) were prepared and stained with modified Wright-Giemsa (WG16, Sigma Aldrich, St. Louis, Mo.).

Figure 8B:
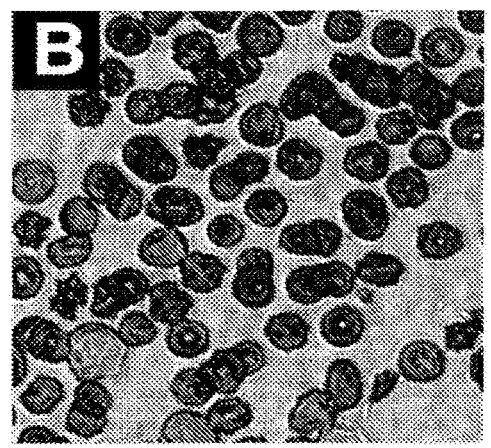

Performance: Fetal nucleated red blood cells were observed in the product fraction (FIG. 8A) and absent from the waste fraction (FIG. 8B).

Example 2

Isolation of Fetal Cells from Maternal Blood

The device and process described in detail in Example 1 were used in combination with immunomagnetic affinity enrichment techniques to demonstrate the feasibility of isolating fetal cells from maternal blood.

Experimental conditions: blood from consenting maternal donors carrying male fetuses was collected into K₂EDTA vacutainers (366643, Becton Dickinson, Franklin Lakes, N.J.) immediately following elective termination of pregnancy. The undiluted blood was processed using the device described in Example 1 at room temperature and within 9 hrs of draw. Nucleated cells from the blood were separated from enucleated cells (red blood cells and platelets), and plasma delivered into a buffer stream of calcium and magnesium-free Dulbecco's Phosphate Buffered Saline (14190-144, Invitrogen, Carlsbad, Calif.) containing 1% Bovine Serum Albumin (BSA) (A8412-100 ML, Sigma-Aldrich, St Louis, Mo.). Subsequently, the nucleated cell fraction was labeled with anti-CD71 microbeads (130-046-201, Miltenyi Biotech Inc., Auburn, Calif.) and enriched using the MiniMACS™ MS column (130-042-201, Miltenyi Biotech Inc., Auburn, Calif.) according to the manufacturer's specifications. Finally, the CD71-positive fraction was spotted onto glass slides.

Measurement techniques: Spotted slides were stained using fluorescence in situ hybridization (FISH) techniques according to the manufacturer's specifications using Vysis probes (Abbott Laboratories, Downer's Grove, Ill.). Samples were stained from the presence of X and Y chromosomes. In one case, a sample prepared from a known Trisomy 21 pregnancy was also stained for chromosome 21.

Figure 10:
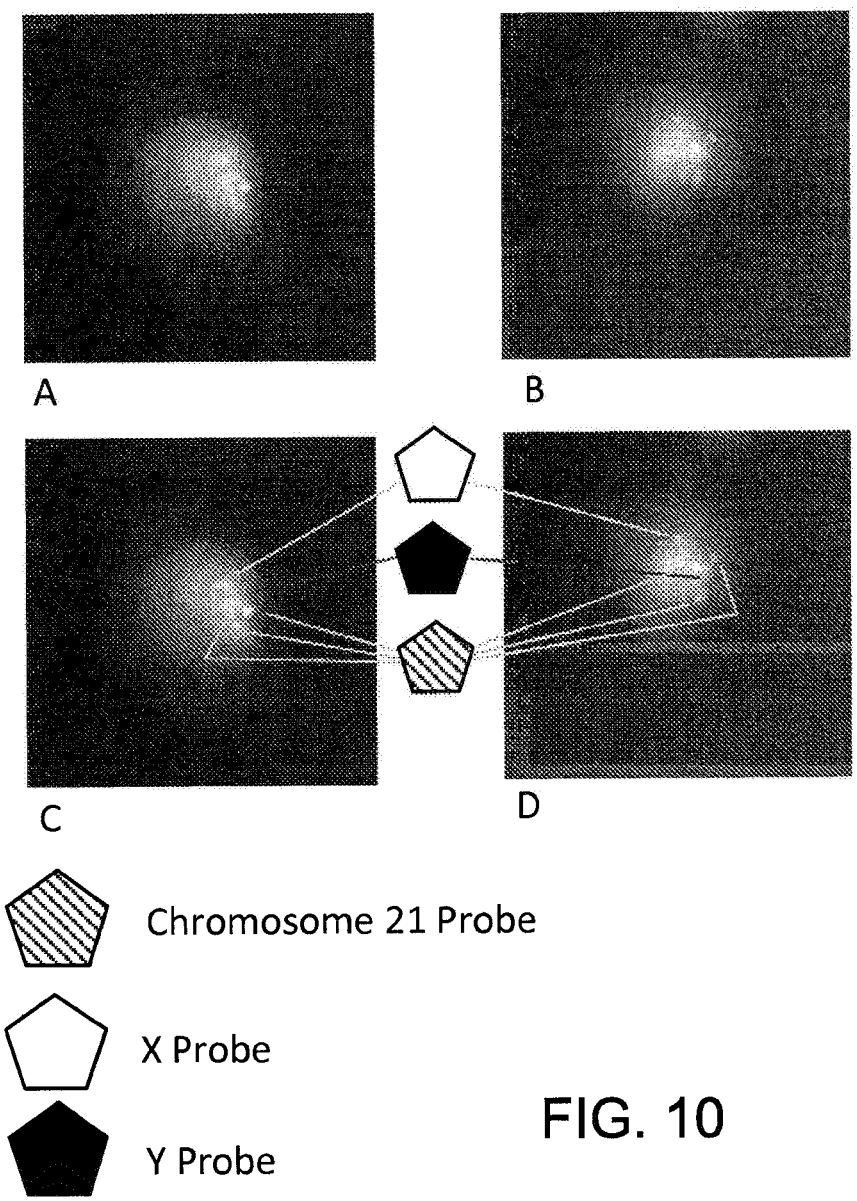
FIG. 10 illustrates trisomy 21 pathology in an isolated fetal nucleated red blood cell.

Performance: Isolation of fetal cells was confirmed by the reliable presence of male cells in the CD71-positive population prepared from the nucleated cell fractions (FIG. 9). In the single abnormal case tested, the trisomy 21 pathology was also identified (FIG. 10).

Example 3

Confirmation of the Presence of Male Fetal Cells in Enriched Samples

Confirmation of the presence of a male fetal cell in an enriched sample is performed using qPCR with primers specific for DYZ, a marker repeated in high copy number on the Y chromosome. After enrichment of fnRBC by any of the methods described herein, the resulting enriched fnRBC are binned by dividing the sample into 100 PCR wells. Prior to binning, enriched samples may be screened by FISH to determine the presence of any fnRBC containing an aneuploidy of interest. Because of the low number of fnRBC in maternal blood, only a portion of the wells will contain a single fnRBC (the other wells are expected to be negative for fnRBC). The cells are fixed in 2% Paraformaldehyde and stored at 4° C. Cells in each bin are pelleted and resuspended in 5 µl PBS plus 1 µl 20 mg/ml Proteinase K (Sigma #P-2308). Cells are lysed by incubation at 65° C. for 60 minutes followed by inactivation of the Proteinase K by incubation for 15 minutes at 95° C. For each reaction, primer sets (DYZ forward primer TCGAGTGCATTCCATTCCG; DYZ reverse primer ATGGAATGGCATCAAACGGAA; and DYZ Taqman Probe 6FAM-TGGCTGTCCATTCCA-MGBNFQ), TaqMan Universal PCR master mix, No AmpErase and water are added. The samples are run and analysis is performed on an ABI 7300: 2 minutes at 50° C., 10 minutes 95° C. followed by 40 cycles of 95° C. (15 seconds) and 60° C. (1 minute). Following confirmation of the presence of male fetal cells, further analysis of bins containing fnRBC is performed. Positive bins may be pooled prior to further analysis.

Figure 20:
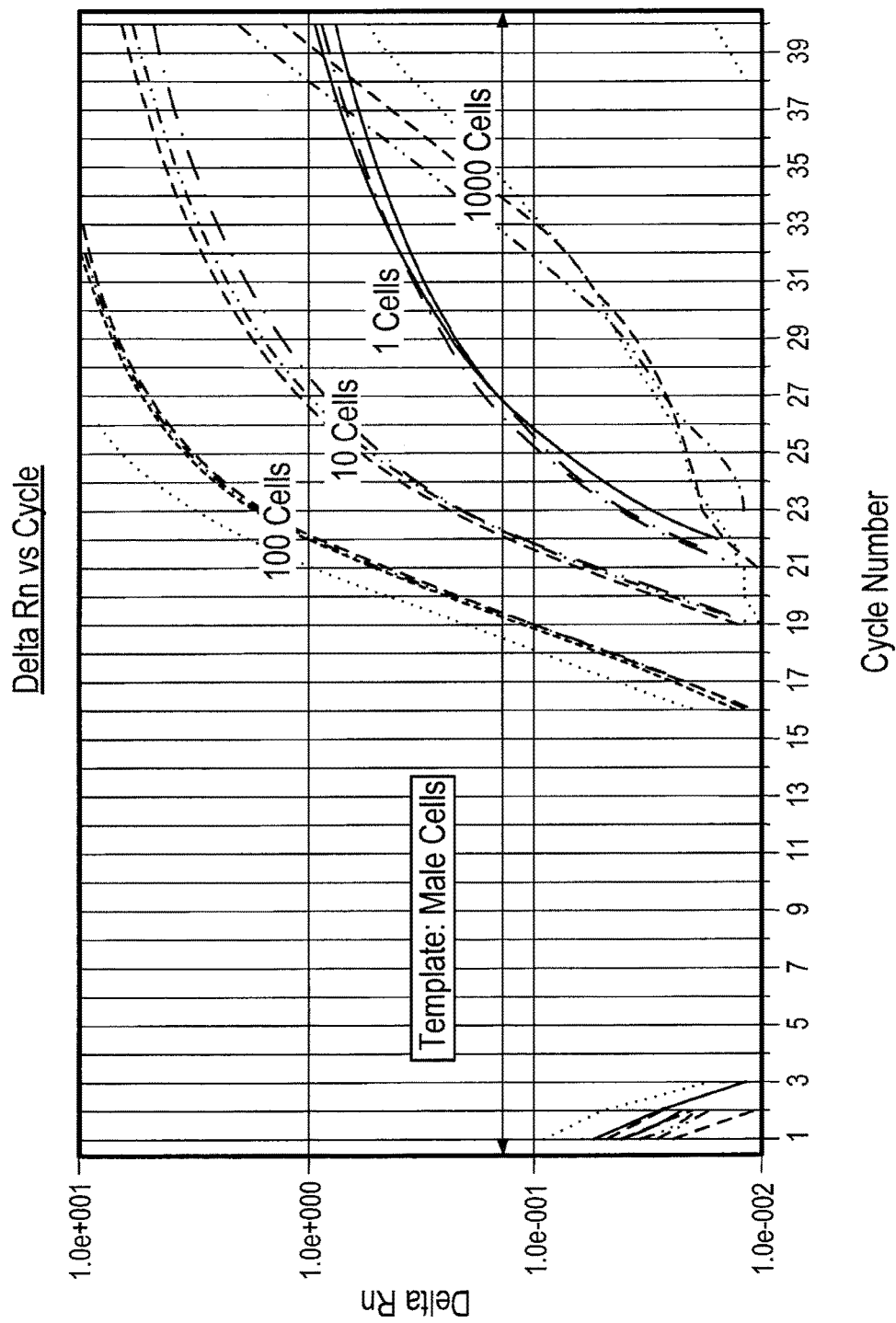
FIG. 20 illustrates the detection of single copies of a fetal cell genome by qPCR.
Figure 21:
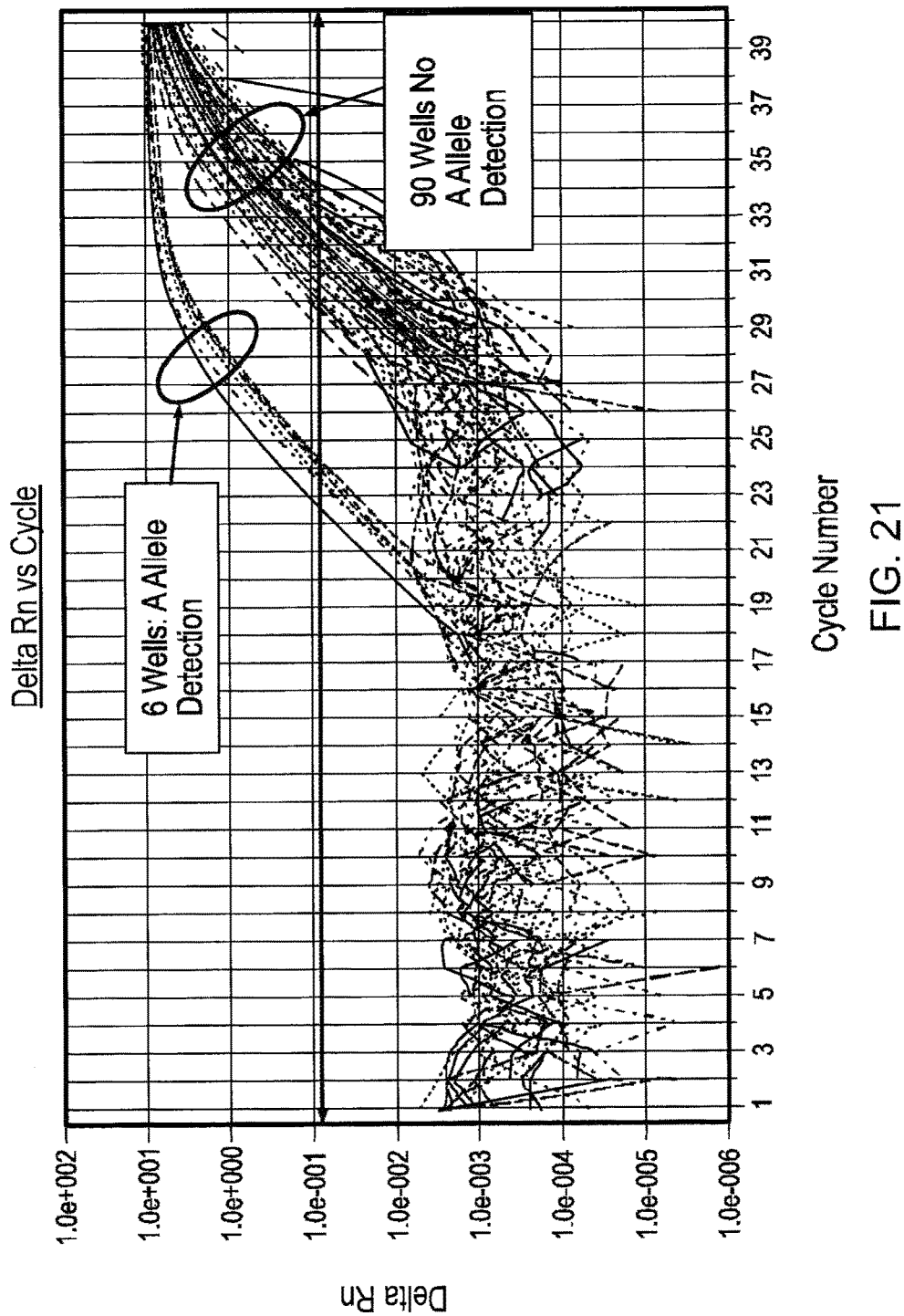
FIG. 21 illustrates detection of single fetal cells in binned samples by SNP analysis.
Figure 22:
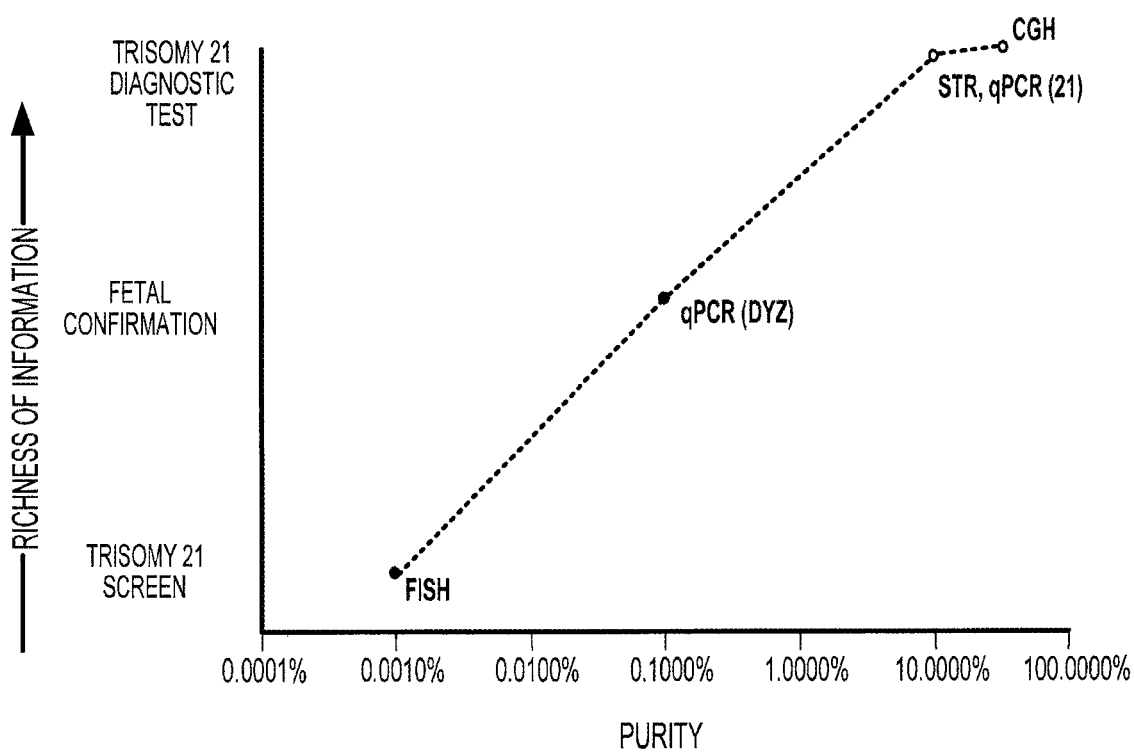
FIG. 22 illustrates a method of trisomy testing. The trisomy 21 screen is based on scoring of target cells obtained from maternal blood. Blood is processed using a cell separation module for hemoglobin enrichment (CSM-HE). Enriched cells are transferred to slides that are first stained and subsequently probed by FISH. Images are acquired, such as from bright field or fluorescent microscopy, and scored. The proportion of trisomic cells of certain classes serves as a classifier for risk of fetal trisomy 21. Fetal genome identification can performed using assays such as: (1) STR markers; (2) qPCR using primers and probes directed to loci, such as the multi-repeat DYZ locus on the Y-chromosome; (3) SNP detection; and (4) CGH (comparative genome hybridization) array detection.
Figure 23:
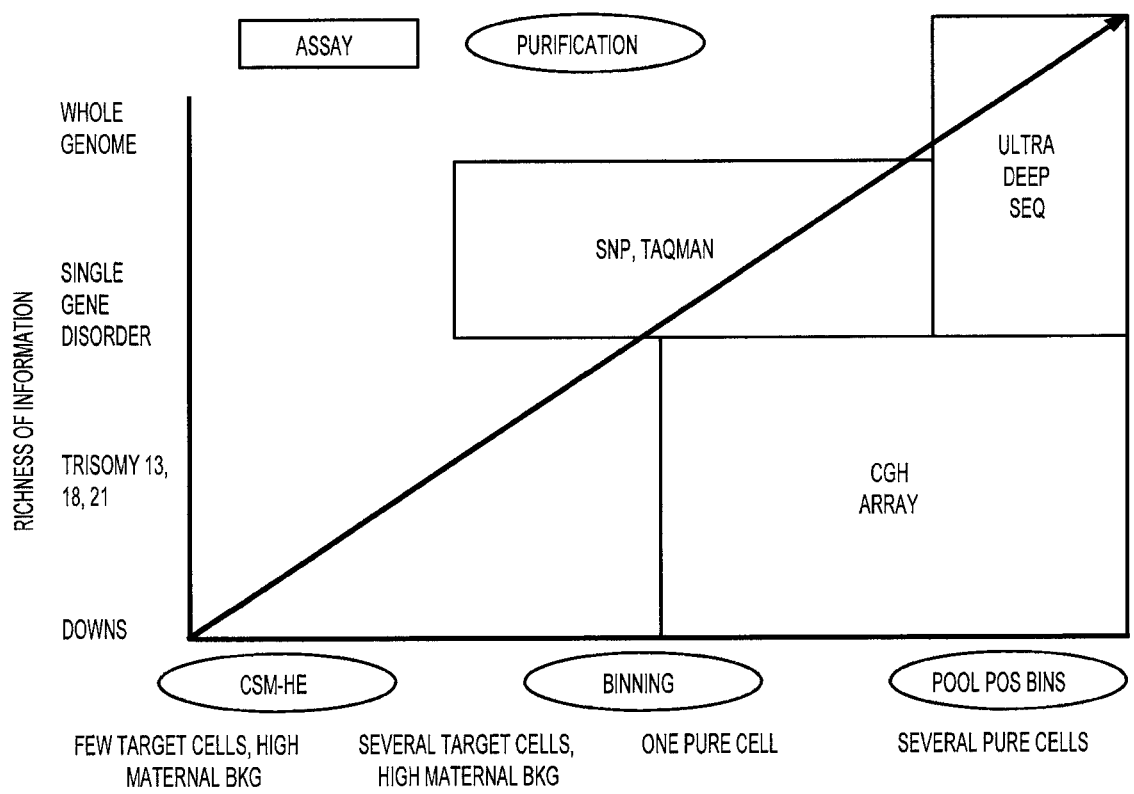
FIG. 23 illustrates assays that can produce information on the presence of aneuploidy and other genetic disorders in target cells. Information on anueploidy and other genetic disorders in target cells may be acquired using technologies such as: (1) a CGH array established for chromosome counting, which can be used for aneuploidy determination and/or detection of intra-chromosomal deletions; (2) SNP/taqman assays, which can be used for detection of single nucleotide polymorphisms; and (3) ultra-deep sequencing, which can be used to produce partial or complete genome sequences for analysis.

FIG. 20 shows the results expected from such an experiment. The data in FIG. 20 was collected by the following protocol. Nucleated red blood cells were enriched from cord cell blood of a male fetus by sucrose gradient two Heme Extractions (HE). The cells were fixed in 2% paraformaldehyde and stored at 4° C. Approximately 10×1000 cells were pelleted and resuspended each in 5 µl PBS plus 1 µl 20 mg/ml Proteinase K (Sigma #P-2308). Cells were lysed by incubation at 65° C. for 60 minutes followed by a inactivation of the Proteinase K by 15 minute at 95° C. Cells were combined and serially diluted 10-fold in PBS for 100, 10 and 1 cell per 6 µl final concentration were obtained. Six µl of each dilution was assayed in quadruplicate in 96 well format. For each reaction, primer sets (DYZ forward primer TCGAGTGCATTCCATTCCG; 0.9 µM DYZ reverse primer ATGGAATGGCATCAAACGGAA; and 0.5 µM DYZ TaqMan Probe 6FAM-TGGCTGTCCATTCCA-MGBNFQ), TaqMan Universal PCR master mix, No AmpErase and water were added to a final volume of 25 µl per reaction. Plates were run and analyzed on an ABI 7300: 2 minutes at 50° C., 10 minutes 95° C. followed by 40 cycles of 95° C. (15 seconds) and 60° C. (1 minute). These results show that detection of a single fnRBC in a bin is possible using this method.

Example 4

Confirmation of the Presence of Fetal Cells in Enriched Samples by STR Analysis

Maternal blood is processed through a size-based separation module, with or without subsequent MHEM enhancement of fnRBCs. The enhanced sample is then subjected to FISH analysis using probes specific to the aneuploidy of interest (e.g., triploidy 13, triploidy 18, and XYY). Individual positive cells are isolated by "plucking" individual positive cells from the enhanced sample using standard micromanipulation techniques. Using a nested PCR protocol, STR marker sets are amplified and analyzed to confirm that the FISH-positive aneuploid cell(s) are of fetal origin. For this analysis, comparison to the maternal genotype is typical. An example of a potential resulting data set is shown in Table 2. Non-maternal alleles may be proven to be paternal alleles by paternal genotyping or genotyping of known fetal tissue samples. As can be seen, the presence of paternal alleles in the resulting cells, demonstrates that the cell is of fetal origin (cells #1, 2, 9, and 10). Positive cells may be pooled for further analysis to diagnose aneuploidy of the fetus, or may be further analyzed individually.

TABLE 2

STR locus alleles in maternal and fetal cells

| DNA Source | STR locus D14S | STR locus D16S | STR locus D8S | STR locus F13B | STR locus vWA |
|---|---|---|---|---|---|
| Maternal alleles | 14, 17 | 11, 12 | 12, 14 | 9, 9 | 16, 17 |
| Cell #1 alleles |  | 8 |  |  | 19 |
| Cell #2 alleles | 17 |  | 15 |  |  |
| Cell #3 alleles |  |  | 14 |  |  |
| Cell #4 alleles |  |  |  |  |  |
| Cell #5 alleles | 17 | 12 |  | 9 |  |
| Cell #6 alleles |  |  |  |  |  |
| Cell #7 alleles |  |  |  |  | 19 |
| Cell #8 alleles |  |  |  |  |  |
| Cell #9 alleles | 17 |  | 14 | 7, 9 | 17, 19 |
| Cell #10 alleles |  |  | 15 |  |  |

Example 5

Confirmation of the Presence of Fetal Cells in Enriched Samples by SNP Analysis

Maternal blood is processed through a size-based separation module, with or without subsequent MHEM enhancement of fnRBCs. The enhanced sample is then subjected to FISH analysis using probes specific to the aneuploidy of interest (e.g., triploidy 13, triploidy 18, and XYY). Samples testing positive with FISH analysis are then binned into 96 microtiter wells, each well containing 15 µl of the enhanced sample. Of the 96 wells, 5-10 are expected to contain a single fnRBC and each well should contain approximately 1000 nucleated maternal cells (both WBC and mnRBC). Cells are pelleted and resuspended in 5 µl PBS plus 1 µl 20 mg/ml Proteinase K (Sigma #P-2308). Cells are lysed by incubation at 65° C. for 60 minutes followed by a inactivation of the Proteinase K by 15 minute at 95° C.

In this example, the maternal genotype (BB) and fetal genotype (AB) for a particular set of SNPs is known. The genotypes A and B encompass all three SNPs and differ from each other at all three SNPs. The following sequence from chromosome 7 contains these three SNPs (rs57795605, rs7795611 and rs7795233 indicated in brackets, respectively)

(ATGCAGCAAGGCACAGACTAA[G/A]CAAGGAGA[G/C]GCAAAATTTT
C[A/G]TAGGGGAGAGAAATGGGTCATT).

In the first round of PCR, genomic DNA from binned enriched cells is amplified using primers specific to the outer portion of the fetal-specific allele A and which flank the interior SNP (forward primer ATGCAGCAAGGCACA-GACTACG; reverse primer AGAGGG-GAGAGAAATGGGTCATT). In the second round of PCR, amplification using real time SYBR Green PCR is performed with primers specific to the inner portion of allele A and which encompass the interior SNP (forward primer

CAAGGCACAGACTAAGCAAGGAGAG;

reverse primer

GGCAAAATTTTCATAGGGGAGAGAAATGGGTCATT).

Expected results are shown in FIG. 31. Here, six of the 96 wells test positive for allele A, confirming the presence of cells of fetal origin, because the maternal genotype (BB) is known and cannot be positive for allele A. DNA from positive wells may be pooled for further analysis or analyzed individually.

Example 6

Analysis of STR's

Figure 11:
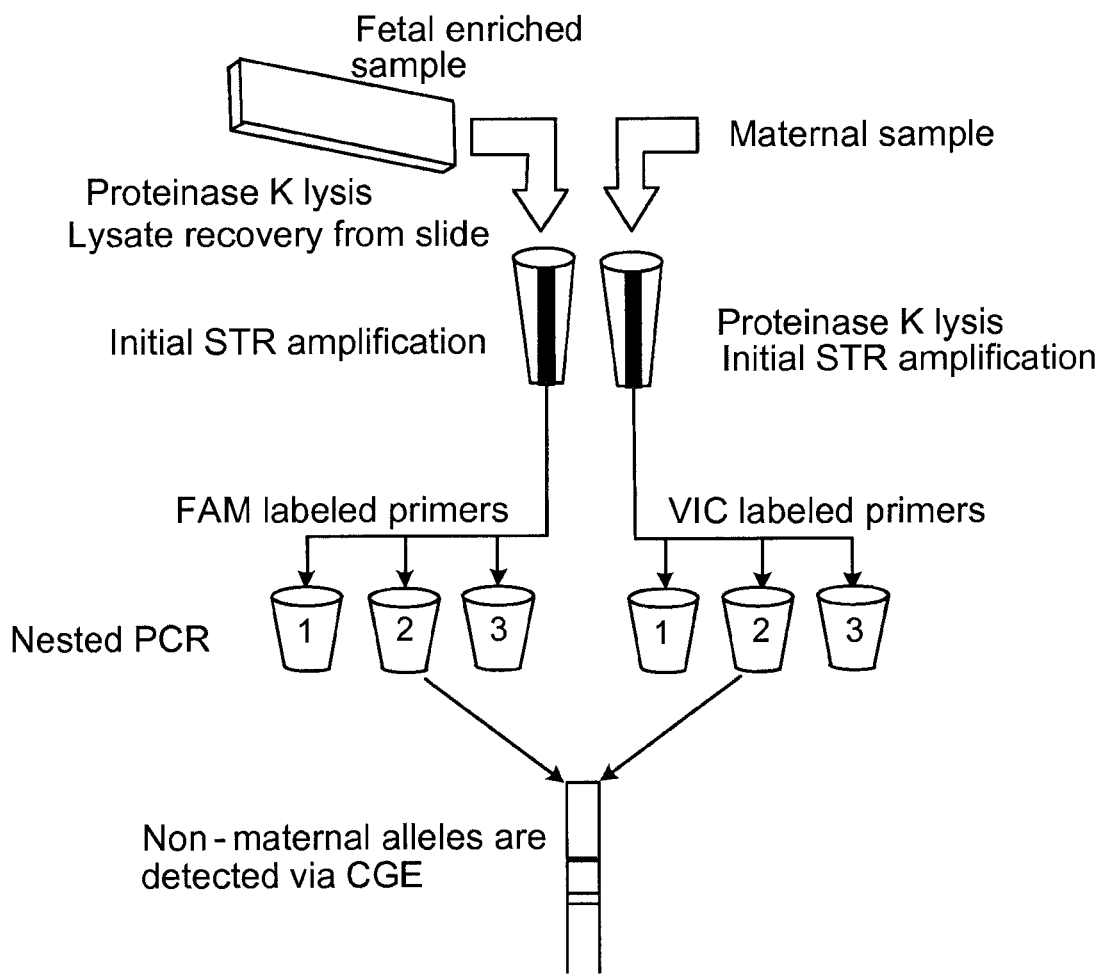
FIG. 11 depicts a flow chart depicting the major steps involved in detecting paternal alleles in a fetal enriched sample using fluorescently labeled primers.

FIG. 11 illustrates a diagram of the planned protocol for clinical practice where a reference sample (maternal blood) and a fetal enriched sample will be processed in parallel. Twelve polymorphic STRs are chosen (See FIG. 12) and associated nested PCR primers were designed (FIG. 13-14).

Cell Lysis: Cells are lysed in a proteinase K solution by heating samples for 60 minutes at 65° C., followed by a heating step of 15 minutes at 95° C.

Pt round of PCR: A polymerase mix that includes 12 specialized STR primer pairs is added to the crude lysate. A master PCR mix is generated according to the number of samples as per the recipe below. For the reference sample 44 µL of the master mix are added directly to the cell lysate. For the sample recovered from the slide the volume of the reaction is adjusted as necessary. (e.g. 32 µL crude lysate in a 100 µL total reaction volume). A no template or negative control is generated to test for contamination.

| Master mix outer 12-plex | |
|---|---|
|  | 1 rxn |
| 2X Qiagen Mix | 25.0 |
| titanium | 1.0 |
| Qiagen Q factor | 5.0 |
| water | 10.0 |
| 4.2 uM 12 plex primers | 3.0 |
| Cell lysate | 6.0 |
|  | 50.0 |

-continued

Multiplex PCR cylce

| Step | Temp (C.) | Time (mins) |
|---|---|---|
| 1.0 | 95 | 0.5 |
| 2.0 | 94 | 0.5 |
| 3.0 | 68 | 1.5 |
| 4.0 | 72 | 1.5 |
| 5.0 | cycle to step 2, 44 times | |
| 6.0 | 72 | 10 |

Nested PCR: After PCR, optionally, diluted products are added to a second nested primer PCR reaction. Two ul aliquot of each 12-plex PCR reaction is diluted 40 fold (to 80 ul total) with nuclease free water from the PCR kit. The diluted fetal enriched 12-plex reaction could be used as template for a master mix for 8 nested PCR reactions with FAM labeled primers. A second master mix can be generated using the dilution from the maternal reference for 8 nested PCR reactions with VIC labeled primers. The following primer pairs are suggested. A no template or negative control is generated to test for contamination Nested STR primer facts

| rxn# | Reaction temp | STR primers | Fragment size ranges |
|---|---|---|---|
| 1 | 68 | CSF1P0 THO1 | 295-327, 171-215 |
| 2 | 68 | TPOX CYARO4 | 220-256, 172-205 |
| 3 | 68 | F13A | 179-235 |
| 4 | 68 | FIBRA | 158-286 |
| 5 | 63 | VWAD21S11 | 122-182 202-265 |
| 6 | 63 | CD4 | 86-141 |
| 7 | 63 | D14S1434 | 70-102 |
| 8 | 63 | D22S1045 | 76-109 |

Master mix for nested primers

| | 1 rxn | 9 rxns |
|---|---|---|
| 2X Q Mix | 12.5 | |
| | 112.5 | |
| titanium | 0.5 | 4.5 |
| Q | 2.5 | |
| | 22.5 | |
| water | 3.3 | |
| | 29.3 | |
| 5 uM primers | 1.3 | |
| 40X diluted template | 5.0 | |
| | 45.0 | |
| | 25.0 | |
| | 213.8 | |

Nested PCR cycle

| Step | Temp (C.) | Time (mins) |
|---|---|---|
| 1.0 | 95 | 0.5 |
| 2.0 | 94 | 0.5 |
| 3.0 | X | 1.5 |
| 4.0 | 72 | 1.5 |
| 5.0 | cycle to step 2, 44 times | |
| 6.0 | 72 | 10 |

The amplification with the nested PCR primers is run with an annealing temperature of 63° C. or 68° C. depending on the primer pair being amplified as indicated in FIG. 13 and FIG. 14.

Detection on ABI 310 Instrument: PCR products are detected on an Agilent Bioanalyzer. The maternal reference VIC labeled PCR reaction products is diluted 10 fold in nano-pure water (17.8 uOhms). Another 10 fold dilution of the fetal enriched FAM-PCR products is generated. The ABI loading buffer is prepared by adding 0.5 µL LIZ 500 size standard to 12 µL Hi Di Formamide (scale as appropriate to the number of samples, include enough buffer for the negative control to test for contamination). 1 µL diluted PCR product is added to 12 ul loading buffer. The sample is heated to 95° C. for 2 minutes and then placed on ice. The samples are loaded onto the ABI 310 as per the manufacturer's instructions.

Analysis: For analysis the ABI fragments output are examined for the expected peak sizes as per the nested STR primer facts table (FIG. 13 and FIG. 14). For each STR locus is determined whether there are 1 or 2 alleles (homozygous or heterozygous) for the fetal enriched (FAM labeled sample) or the maternal reference (VIC labeled sample). Alleles generated from the fetal enriched (FAM labeled sample) that are not present in the maternal reference (VIC labeled sample) are unique to the fetus and verify the presence of fetal cells in the sample. If the number of fetal cells is particularly low (<5 cells), not all loci or alleles will always amplify. Allele drop out can generate a false negative. A false positive is most likely generated from contamination and has not been observed in tests to date. If the purity of fetal cells is particularly low (<10% in tests executed on the bioanalyzer) signal intensity of paternal alleles can be very weak. This can also generate a false negative result. In clinical practice the amplicons will have different fluorescent labels incorporated into them marking them as the maternal reference or the fetal enriched samples. The labels allow the samples to be loaded simultaneously into an ABI 310 capillary and differentiated. Paternal alleles are identified as those unique to the fetal enriched sample in comparison to the maternal reference. The efficiency of the overall process is determined after sufficient samples have been analyzed on the ABI 310 to establish the input cell purity and minimum number of fetal cells necessary to achieve 99% detection at 0.1% false positive rate.

Example 7

Cord Blood Experiment

Figure 15:
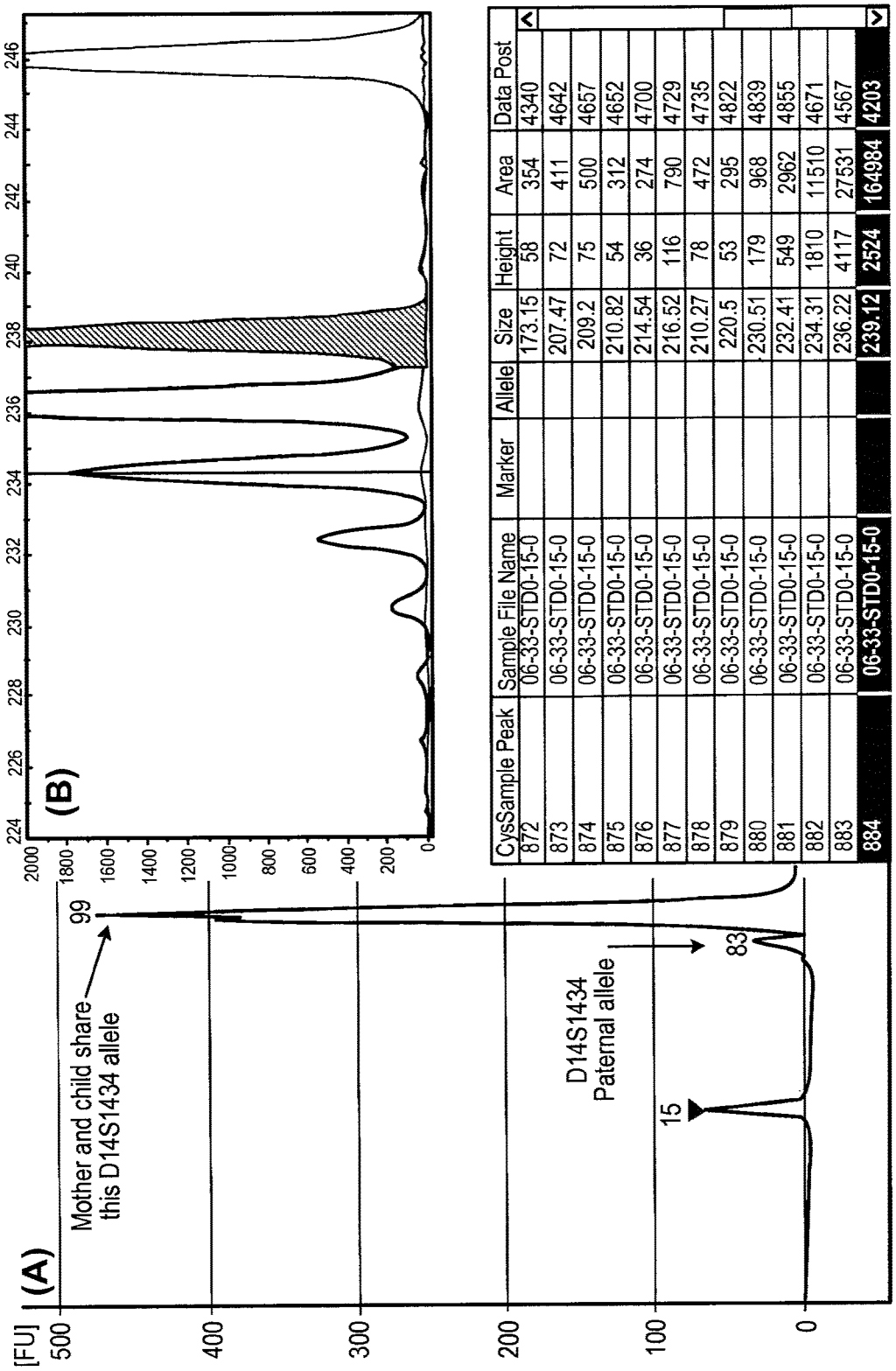
FIG. 15 illustrates the resolution for the ABI 310 bioanalyzer.
Figure 16:
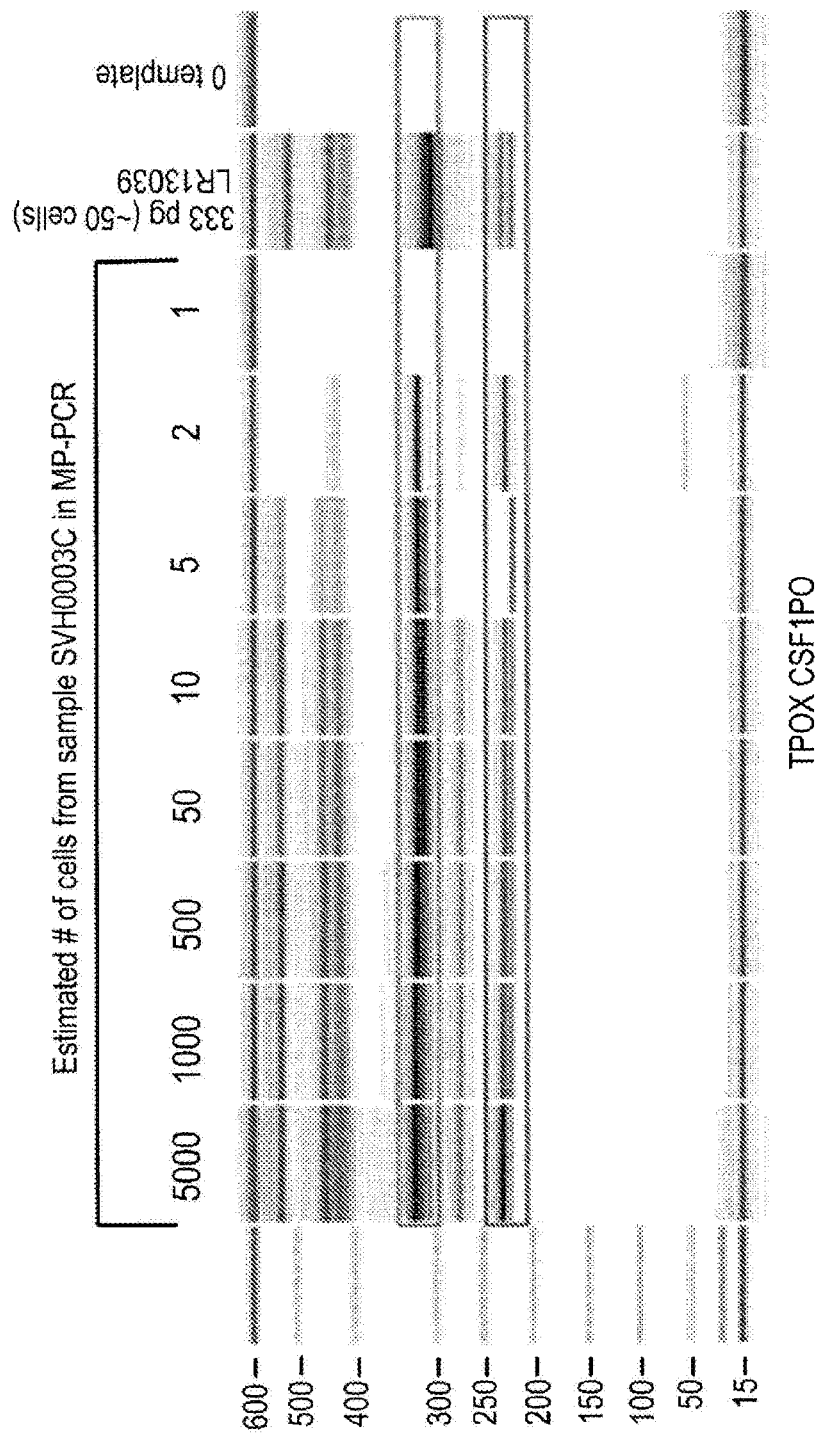
FIG. 16 illustrates the detection limit on fixed cord blood.

The protocol detection limit was determined using fixed cells from cord blood. Cord blood from clinical sample SVH0003C was subjected to erythrocyte lysis and the remaining leukocytes were fixed in a solution of PBS and 2% para-formaldehyde. Cell numbers were estimated from hemocytometer counts and dilutions made into a Tris protienase K (PK) solution. After cell lysis and PK inactivation a PCR cocktail including primers for STR loci TPDX and CSF1P0 was added directly to the crude lysate and amplified as described in Example 6. The products were analyzed on an Agilent bioanalyzer. FIGS. 15A-15B shows representative results. TPDX and CSF1P0 amplification products are underline in boxes. Detection for the PCR protocol from fixed cord blood can occur with less than 10 cells as shown by the result in FIG. 16.

Example 8

Detection of 10 Fetal Cells at 10% Purity without Nested PCR

Figure 17:
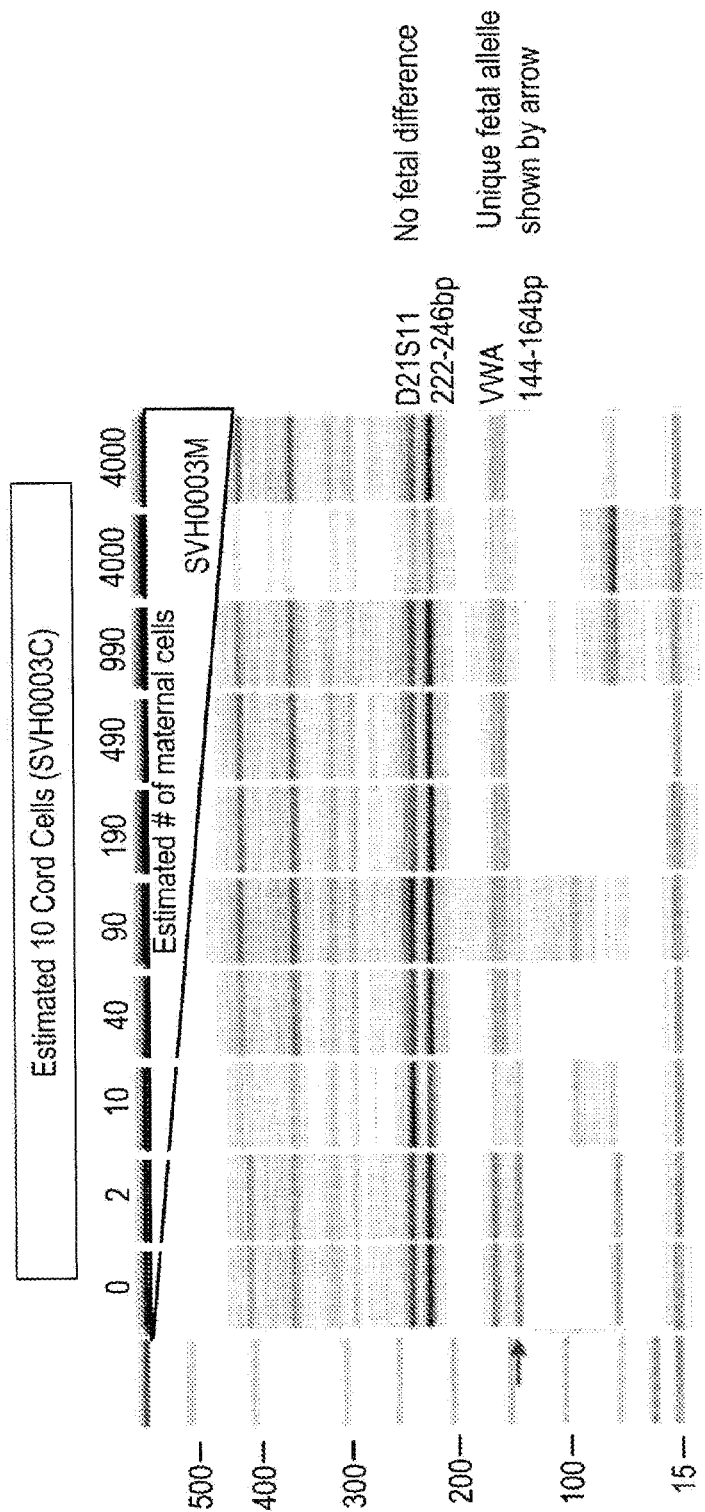
FIG. 17 illustrates the detection of 10 fetal cells at 10% purity without nested PCR.

An estimated 10 fetal cells were mixed with increasing amounts of maternal cells (approximately 0-4000 cells as measured by hemocytometer counts). After proteinase K lysis, only a $1^{st}$ round of PCR with primers to STR loci D21S11 and VWA was executed as described in Example 6. FIG. 17 shows representative results. The mother and fetus are identical at the D21S11 locus but the child has a unique (paternal) allele at the VWA locus. FIG. 17 shows that detection of the paternal VWA allele is lost when the fetal purity drops below 10%.

Example 9

Generation of STR Markers

Figure 18:
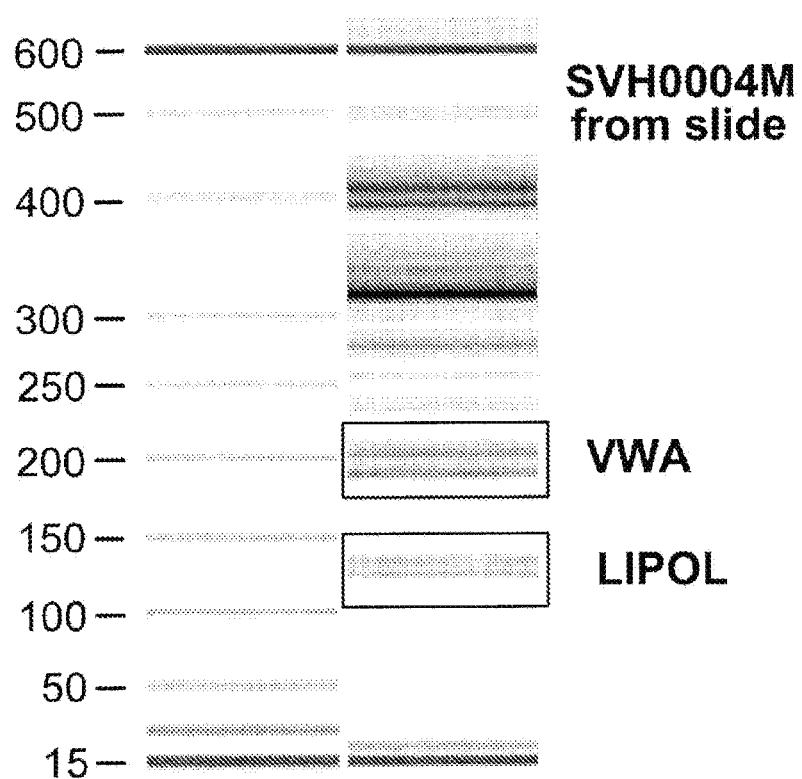
FIG. 18 illustrates the generation of STR markers on fixed cells recovered from a slide.

Approximately 100 cells were spotted onto a poly-L-lysine slide and heat dried. Cells were fixed in a MeOH acetic acid solution and rinsed in MeOH. After air drying the slide was treated with 2% para-formaldehyde for 10 minutes then washed in 1X PBS. The slide was dehydrated in passes of EtOH for 1 min each in 70%, 80%, 90%, and finally 100%. A dam was applied around the cells and 30 ul of proteinase K was added on top of the cells and a cover slip adhered over the dam. The slide was incubated on a heat block at 65° C. for 60 minutes and 95° C. for 15 minutes. The lysate solution was then transferred directly to a 100 ul PCR reaction with VWA and LIPOL primer. PCR protocol and analysis were performed as described in Example 6. FIG. 18 shows representative results. VWA and LIPOL amplicons are underlined by boxes in the figure. These results show that STRs markers can be generated from fixed cells recovered from a slide.

Example 10

Figure 19:
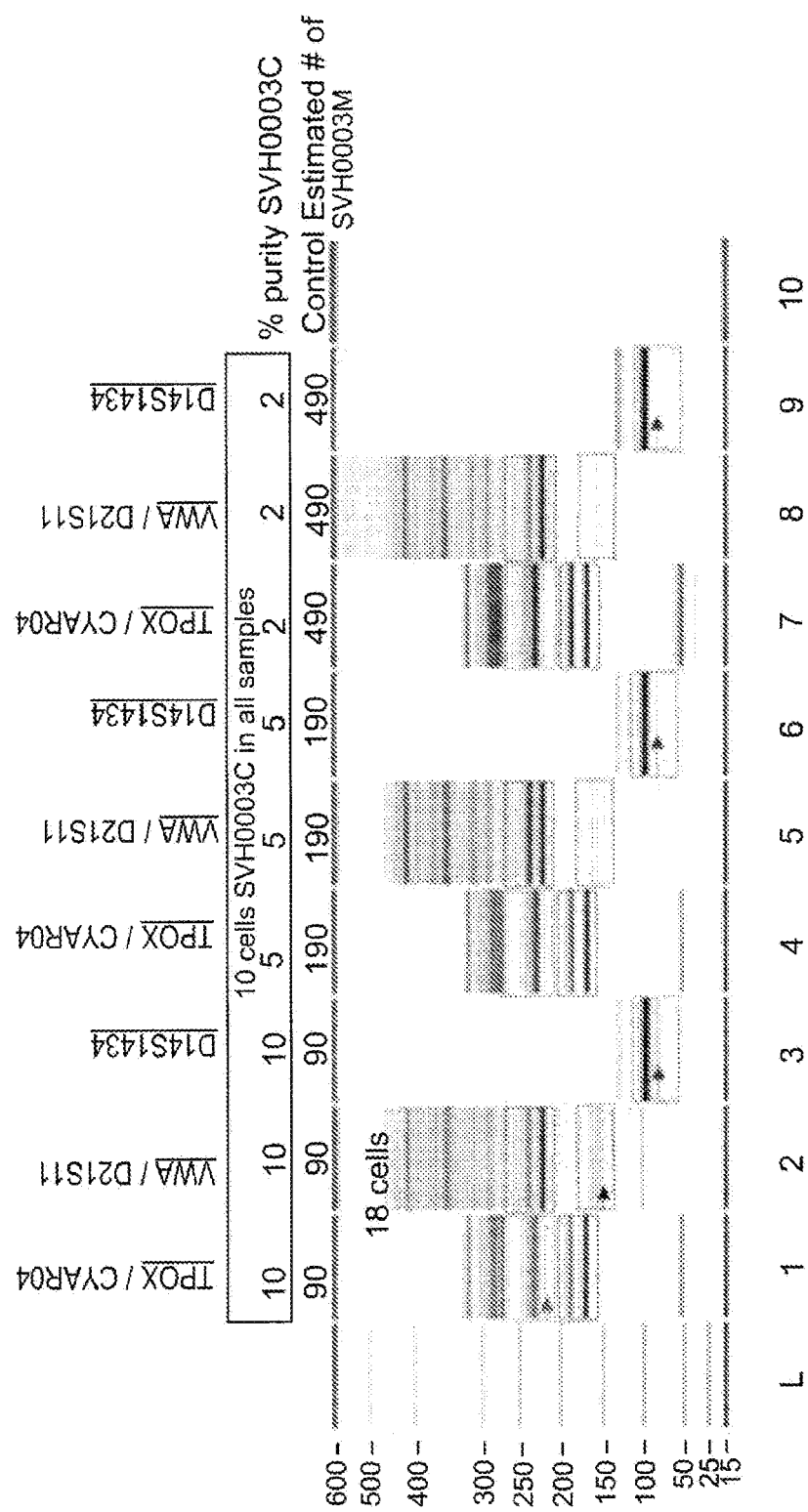
FIG. 19 illustrates detection of fetal alleles at less than 10% purity after nested PCR amplification of STRs.

Detection of Fetal Alleles at Less than 10% Purity after Nested PCR Amplification of STRs Mutliplex PCR reactions from samples with 10 fetal cells in a background of maternal cells generating at 10%, 5% and 2% fetal cells purity concentration were performed as described in Example 6. A dilution of the three multiplex PCR reactions was used as template in nested PCR reactions for STRs TPDX/CYAR04, VWA/D21S11, and D14S1434 as described in Example 6. FIG. 19 shows representative results. The underlined loci are known to have unique fetal alleles which are designated by arrows when visible in the gel. The three loci were visible when fetal cells constituted 10% of the sample. D14S1434 loci was visible when fetal cells constituted 5% and 2% of the sample.

Example 11

Resolution of the Bioanalyzer

FIG. 15A shows that the Bioanalyzer can resolve a 16 base pair difference between the 99 base pair D14S1434 maternal allele and the 83 base pair paternal allele in a mixed fetal sample at 5% purity (also shown in FIG. 11, lane 6). FIG. 15B shows that the output of fragments calibration standards. The output of an ABI310 fragment calibration standard is shown in blue or FAM label. Fragments of 232, 234, 236 and 238 are easily resolved from one another. For a resolution comparison note that the orange, VIC labeled, 246 size standard peak is 8 bases away from the FAM labeled 238 peak, half the distance as the maternal and paternal alleles in the Bioanalyzer trace.

Example 12

Analysis of STR's Using Quantitative Fluorescence

Genomic DNA from enriched fetal cells and a maternal control sample will be genotyped for specific STR loci in order to assess the presence of chromosomal abnormalities, such as trisomy. Due to the small number of fetal cells typically isolated from maternal blood it is advantageous to perform a pre-amplification step prior to analysis, using a protocol such as improved primer extension pre-amplification (IPEP) PCR. Cell lysis is carried out in 10 ul High Fidelity buffer (50 mM Tris-HCL, 22 mM $(NH_4)_2SO_4$ 2.5 mM $MgCl_2$, pH 8.9) which also contained 4 mg/ml proteinase K and 0.5 vol % Tween 20 (Merck) for 12 hours at 48° C. The enzyme is then inactivated for 15 minutes at 94° C. Lysis is performed in parallel batches in 5 ul, 200 mM KOH, 50 mM dithiothreitol for 10 minutes at 65.degree. The batches are then neutralized with 5 ul 900 mM TrisHCl pH 8.3, 300 mM KCl. Preamplication is then carried out for each sample using completely randomized 15-mer primers (16 uM) and dNTP (100 uM) with 5 units of a mixture of Taq polymerase (Boehringer Mannheim) and Pwo polymerase (Boehringer Mannheim) in a ratio of 10:1 under standard PCR buffer conditions (50 mM Tris-HCL, 22 mM $(NH_{0.4})_2$ $SO_4$, 2.5 mM $Mg_2$, pH 8.9, also containing 5% by vol. of DMSO) in a total volume of 60 ul with the following 50 thermal cycles: Step Temperature Time (1) 92° C. 1 Min 30 Sec; (2) 92° C. 40 Min (3) 37° C. 2 Min; (4) ramp: 0.1° C./sec to 55° C. (5) 55° C. 4 Min (6)68° C. 30 Sec (7) go to step 2, 49 times (8) 8° C. 15 ' Min.

Dye labeled primers will then be selected from Table 3 based on STR loci on a chromosomes of interest, such as 13,18, 21 or X. The primers are designed so that one primer of each pair contains a fluorescent dye, such as ROX, HEX, JOE, NED, FAM, TAMARA or LIZ. The primers are placed into multiplex mixes based on expected product size, fluorescent tag compatibility and melting temperature. This allows multiple STR loci to be assayed at once and yet still conserves the amount of initial starting material required. All primers are initially diluted to a working dilution of 10 pM. The primers are then combined in a cocktail that has a final volume of 40 ul. Final primer concentration is determined by reaction optimization Additional PCR grade water is added if the primer mix is below 40 ul. A reaction mix containing 6 ul of Sigma PCR grade water, 1.25 ul of Perkin Elmer Goldamp PCR buffer, 0.5 ul of dNTPs, 8 ul of the primer cocktail, 0.12 ul of Perkin Elmer Taq Gold Polymerase and 1.25 ul of Mg (25 mM) is mixed for each sample. To this a 1 ul sample containing preamplified DNA from enriched fetal cells or maternal control genomic DNA is added.

The reaction mix is amplified in a DNA thermocyler, (PTC-200; MJ Research) using an amplification cycle optimized for the melting temperature of the primers and the amount of sample DNA.

The amplification product will then analyzed using an automated DNA sequencer system, such as the ABI 310, 377, 3100, 3130, 3700 or 3730, or the Li-Cor 4000, 4100, 4200 or 4300. For example when the amplification products are prepared for analysis on a ABI 377 sequencer, 6 ul of products will be removed and combined with 1.6 ul of loading buffer mix. The master loading buffer mix contains 90 ul deionized formamide combined with 25 ul Perkin Elmer loading dye and 10 ul of a size standard, such as the ROX 350 size standard Various other standards can be used interchangeably depending on the sizes of the labeled PCR products. The loading buffer and sample are then heat denatured at 95° C. for 3 minutes followed by flash cooling on ice. 2 ul of the product/buffer mix is then electrophoresed on a 12 inch 6% (19:1) polyacrylamide gel on an ABI 377 sequencer.

The results will then be analyzed using ABI Genotyper software. The incorporation of a fluorochrome during amplification allows product quantification for each chromosome specific STR, with 2 fluorescent peaks observed in a normal heterozygous individual with an approximate ratio of 1:1. By comparison in trisomic samples, either 3 fluorescent peaks with a ratio of 1:1:1 (trialleleic) or 2 peaks with a ratio of around 2:1 (diallelic) are observed. Using this method screening may be carried out for common trisomies and sex chromosome aneuploidy in a single reaction.

TABLE 3

Primer Sets for STRs on Chromsomes 13, 18, 21 and X

| Ch. | STR Marker | Primer 1 | Primer 2 |
| --- | --- | --- | --- |
| 13 | D13S317 | 5ACAGAAGTCTGGGATGTGGA (SEQ ID NO 1) | GCCCAAAAAGACAGACAGAA (SEQ ID NO 2) |
|  | D13S1493 | ACCTGTTGTATGGCAGCAGT (SEQ ID NO 3) | AGTTGACTCTTTCCCCAACTA (SEQ ID NO 4) |
|  | D13S1807 | TTTGGTAAGAAAAACATCTCCC (SEQ ID NO 5) | GGCTGCAGTTAGCTGTCATT (SEQ ID NO 6) |
|  | D13S256 | CCTGGGCAACAAGAGCAAA (SEQ ID NO 7) | AGCAGAGAGACATAATTGTG (SEQ ID NO 8) |
|  | D13S258- | ACCTGCCAAATTTTACCAGG (SEQ ID NO 9) | GACAGAGAGAGGGAATAAACC (SEQ ID NO 10) |
|  | D13S285 | ATATATGCACATCCATCCATG (SEQ ID NO 11) | GGCCAAAGATAGATAGCAAGGTA (SEQ ID NO 12) |
|  | D13S303 | ACATCGCTCCTTACCCCATC (SEQ ID NO 13) | TGTACCCATTAACCATCCCA (SEQ ID NO 14) |
|  | D13S317 | ACAGAAGTCTGGGATGTGGA (SEQ ID NO 15) | GCCCAAAAAGACAGACAGAA (SEQ ID NO 16) |
|  | D13S779 | AGAGTGAGATTCTGTCTCAATTAA (SEQ ID NO 17) | GGGCCTGTGTAGAAGCTGTA (SEQ ID NO 18) |
|  | D13S787 | ATCAGGATTCCAGGAGGAAA (SEQ ID NO 19) | ACCTGGGAGGCGGAGCTC (SEQ ID NO 20) |
|  | D13S793 | GGCATAAAAATAGTACAGCAAGC (SEQ ID NO 21) | ATTTGAACAGGCATGTAC (SEQ ID NO 22) |
|  | D13S796 | CATGGATGCAGAATTCACAG (SEQ ID NO 23) | TCATCTCCCTGTTTGGTAGC (SEQ ID NO 24) |
|  | D13S800 | AGGGATCTTCAGAGAAACAGG (SEQ ID NO 25) | TGACACTATCAGCTCTCTGGC (SEQ ID NO 26) |
|  | D13S894 | GGTGCTTGCTGTAAATATAATTG (SEQ ID NO 27) | CACTACAGCAGATTGCACCA (SEQ ID NO 28) |
| 18 | D18S51 | CAAACCCGACTACCAGCAAC (SEQ ID NO 29) | GAGCCATGTTCATGCCACTG (SEQ ID NO 30) |
|  | D18S1002 | CAAAGAGTGAATGCTGTACAAACAGC (SEQ ID NO 31) | CAAGATGTGAGTGTGCTTTTCAGGAG (SEQ ID NO 32) |
|  | D18S1357 | ATCCCACAGGATGCCTATTT (SEQ ID NO 33) | ACGGGAGCTTTTGAGAAGTT (SEQ ID NO 34) |
|  | D18S1364 | TCAAATTTTTAAGTCTCACCAGG (SEQ ID NO 35) | GCCTGTAGAAAGCAACAACC (SEQ ID NO 36) |
|  | D18S1370 | GGTGACAGAGCAAGACCTTG (SEQ ID NO 37) | GCCTCTTGTCATCCCAAGTA (SEQ ID NO 38) |
|  | D18S1371 | CTCTCTTCATCCACCATTGG (SEQ ID NO 39) | GCTGTAAGAGACCTGTGTTG (SEQ ID NO 40) |
|  | D18S1376 | TGGAACCACTTCATTCTTGG (SEQ ID NO 41) | ATTTCAGACCAAGATAGGC (SEQ ID NO 42) |
|  | D18S1390 | CCTATTTAAGTTTCTGTAAGG (SEQ ID NO 43) | ATGGTGTAGACCCTGTGGAA (SEQ ID NO 44) |
|  | D18S499 | CTGCACAACATAGTGAGACCTG (SEQ ID NO 45) | AGATTACCCAGAAATGAGATCAGC (SEQ ID NO 46) |
|  | D18S535 | TCATGTGACAAAAGCCACAC (SEQ ID NO 47) | AGACAGAAATATAGATGAGAATGCA (SEQ ID NO 48) |
|  | D18S535 | TCATGTGACAAAAGCCACAC (SEQ ID NO 49) | AGACAGAAATATAGATGAGAATGCA (SEQ ID NO 50) |
|  | D18S542 | TTTCCAGTGGAAACCAAACT (SEQ ID NO 51) | TCCAGCAACAACAAGAGACA (SEQ ID NO 52) |
|  | D18S843 | GTCCTCATCCTGTAAAACGGG (SEQ ID NO 53) | CCACTAACTAGTTTGTGACTTTGG (SEQ ID NO 54) |
|  | D18S851 | CTGTCCTCTAGGCTCATTTAGC (SEQ ID NO 55) | TTATGAAGCAGTGATGCCAA (SEQ ID NO 56) |
|  | D18S858 | AGCTGGAGAGGGATAGCATT (SEQ ID NO 57) | TGCATTGCATGAAAGTAGGA (SEQ ID NO 58) |
|  | D18S877 | GATGATAGAGATGGCACATGA (SEQ ID NO 59) | TCTTCATACATGCTTTATCATGC (SEQ ID NO 60) |
| 21 | D21S11 | GTGAGTCAATTCCCCAAG (SEQ ID NO 61) | GTTGTATTAGTCAATGTTCTCC (SEQ ID NO 62) |
|  | D21S1411 | ATGATGAATGCATAGATGGATG (SEQ ID NO 63) | AATGTGTCCTTCCAGGC (SEQ ID NO 64) |
|  | D21S1413 | TTGCAGGGAAACCACAGTT (SEQ ID NO 65) | TCCTTGGAATAAATTCCCGG (SEQ ID NO 66) |
|  | D21S1432 | CTTAGAGGGACAGAACTAATAGGC (SEQ ID NO 67) | AGCCTATTGTGGGTTTGTGA (SEQ ID NO 68) |
|  | D21S1437 | ATGTACATGTGTCTGGGAAGG (SEQ ID NO 69) | TTCTCTACATATTTACTGCCAACA (SEQ ID NO 70) |
|  | D21S1440 | GAGTTTGAAAATAAAGTGTTCTGC (SEQ ID NO 71) | CCCCACCCCTTTTAGTTTTA (SEQ ID NO 72) |
|  | D21S1446 | ATGTACGATACGTAACACTTGACAA (SEQ ID NO 73) | GTCCCAAAGGACCTGCTC (SEQ ID NO 74) |
|  | D21S2052 | GCACCCCTTTATACTTGGGTG (SEQ ID NO 75) | TAGTACTCTACCATCCATCTATCCC (SEQ ID NO 76) |
|  | D21S2055 | AACAGAACCAATAGGCTATCTATC (SEQ ID NO 77) | TACAGTAAATCACTTGGTAGGAGA (SEQ ID NO 78) |
| X | SBMA | TCCGCGAAGTGAAGAAC (SEQ ID NO 79) | CTTGGGGAGAACCATCCTCA (SEQ ID NO 80) |
|  | DXS1047 | CCGGCTACAAGTGATGTCTA (SEQ ID NO 81) | CCTAGGTAACATAGTGAGACCTTG (SEQ ID NO 82) |
|  | DXS1068 | CCTCTAAAGCATAGGGTCCA (SEQ ID NO 83) | CCCATCTGAGAACACGCTG (SEQ ID NO 84) |
|  | DXS1283E | AGTTTAGGAGATTATCAAGCTGG (SEQ ID NO 85) | GTTCCCATAATGATGTATCCAG (SEQ ID NO 86) |
|  | DXS6789 | TTGGTACTTAATAAACCCTCTTTT (SEQ ID NO 87) | CTAGAGGGACAGAACCAATAGG (SEQ ID NO 88) |
|  | DXS6795 | TGTCTGCTAATGAATGATTTGG (SEQ ID NO 89) | CCATCCCCTAAACCTCTCAT (SEQ ID NO 90) |
|  | DXS6800 | GTGGGACCTTGTGATTGTGT (SEQ ID NO 91) | CTGGCTGACACTTAGGGAAA (SEQ ID NO 92) |

TABLE 3-continued

Primer Sets for STRs on Chromsomes 13, 18, 21 and X

| Ch. | STR Marker | Primer 1 | Primer 2 |
|---|---|---|---|
| | DXS6810 | ACAGAAAACCTTTTGGGACC (SEQ ID NO 93) | CCCAGCCCTGAATATTATCA (SEQ ID NO 94) |
| | DXS7127 | TGCACTTAATATCTGGTGATGG (SEQ ID NO 95) | ATTTCTTTCCCTCTGCAACC (SEQ ID NO 96) |
| | DXS7132 | AGCCCATTTTCATAATAAATCC (SEQ ID NO 97) | AATCAGTGCTTTCTGTACTATTGG (SEQ ID NO 98) |
| | DXS8377 | CACTTCATGGCTTACCACAG (SEQ ID NO 99) | GACCTTTGGAAAGCTAGTGT (SEQ ID NO 100) |
| | DXS9893 | TGTCACGTTTACCCTGGAAC (SEQ ID NO 101) | TATTCTTCTATCCAACCAACAGC (SEQ ID NO 102) |
| | DXS9895 | TTGGGTGGGGACACAGAG (SEQ ID NO 103) | CCTGGCTCAAGGAATTACAA (SEQ ID NO 104) |
| | DXS9896 | CCAGCCTGGCTGTTAGAGTA (SEQ ID NO 105) | ATATTCTTATATTCCATATGGCACA (SEQ ID NO 106) |
| | DXS9902 | TGGAGTCTCTGGGTGAAGAG (SEQ ID NO 107) | CAGGAGTATGGGATCACCAG (SEQ ID NO 108) |
| | DXS998 | CAGCAATTTTTCAAAGGC (SEQ ID NO 109) | AGATCATTCATATAACCTCAAAAGA (SEQ ID NO 110) |

What is claimed is:

1. A method of analyzing a fetal cell in a mixed sample obtained from a pregnant human female, the method comprising:
   (a) obtaining the mixed sample comprising fetal and maternal cells;
   (b) enriching the mixed sample for fetal cells to produce an enriched sample comprising fetal cells and maternal cells, wherein the enrichment increases the ratio of fetal cells to maternal cells to about 1/10,000 to about 1/10;
   (c) binning fetal cells and maternal cells from the enriched sample by serial dilution, wherein the binning results in at least one bin containing an individual fetal cell from the enriched sample;
   (d) identifying bins that contain at least one fetal cell using one or more fetal cell biomarkers;
   (e) lysing fetal cells in the identified bins;
   (f) amplifying genomes of the lysed fetal cells in the identified bins to produce amplified nucleic acids; and
   (g) analyzing the amplified nucleic acids in bins that contain at least one fetal cell for aneuploidy using ultra-deep sequencing.

2. The method of claim 1, wherein the analyzing comprises analyzing for fetal aneuploidy, wherein the fetal aneuploidy comprises monosomy, trisomy, tetrasomy, or pentasomy of one or more chromosomes.

3. The method of claim 2, wherein the fetal aneuploidy is a fetal aneuploidy of a chromosome selected from the group consisting of chromosome 13, chromosome 18, chromosome 21, chromosome X, and chromosome Y.

4. The method of claim 2, wherein the fetal aneuploidy comprises trisomy or monosomy.

5. The method of claim 4, wherein the fetal aneuploidy comprises trisomy, and wherein the trisomy comprises trisomy 13, trisomy 18, or trisomy 21.

6. The method of claim 4, wherein the fetal aneuploidy comprises monosomy X and the chromosome suspected of being aneuploid comprises chromosome X.

7. The method of claim 1, wherein the fetal aneuploidy comprises XXX, XXY, or XYY.

8. The method of claim 1, wherein the ultra-deep sequencing produces partial genome sequences for analysis.

9. The method of claim 1, wherein the ultra-deep sequencing produces complete genome sequences for analysis.

10. The method of claim 1, wherein amplifying the genomes of the lysed fetal cells comprises amplifying whole genomes of the lysed fetal cells.

11. The method of claim 1, wherein the binning comprises use of a nanofluidic system.

12. The method of claim 11, wherein the nanofluidic system separates samples into droplets.

13. The method of claim 1, further comprising positive selection for fetal cells prior to binning.

14. The method of claim 1, further comprising negative selection for non-target cells prior to binning.

15. The method of claim 1, wherein the enrichment increases the ratio of fetal cells to maternal cells to about 1/100 to about 1/10.

16. The method of claim 1, wherein the enrichment increases the ratio of fetal cells to maternal cells to about 1/50 to about 1/10.

17. The method of claim 1, wherein the enrichment increases the ratio of fetal cells to maternal cells to about 1/10.

18. The method of claim 1, wherein the mixed sample is obtained from whole blood, bone marrow suspension, or milk.

19. The method of claim 1, wherein the enriching comprises contacting the mixed sample with particles coupled to antibodies that selectively bind to fetal cells.

20. The method of claim 19, wherein the particles are magnetic particles.

* * * * *

UNITED STATES PATENT AND TRADEMARK OFFICE
CERTIFICATE OF CORRECTION

PATENT NO. : 11,378,498 B2
APPLICATION NO. : 16/819992
DATED : July 5, 2022
INVENTOR(S) : Roland Stoughton et al.

It is certified that error appears in the above-identified patent and that said Letters Patent is hereby corrected as shown below:

On the Title Page

Column 1, item (73) Under Assignees:
Delete "GPR" and Insert --GPB--

Column 2, Under Other Publications:
Delete "May 6," and Insert --May 6, 2015--

Signed and Sealed this
Sixth Day of September, 2022

Katherine Kelly Vidal
*Director of the United States Patent and Trademark Office*